US008647629B2

(12) United States Patent
Rammensee et al.

(10) Patent No.: US 8,647,629 B2
(45) Date of Patent: Feb. 11, 2014

(54) POWERFUL MHC-CLASS II PEPTIDES DERIVED FROM SURVIVIN

(75) Inventors: Hans-Georg Rammensee, Tuebingen (DE); Stefan Stevanovic, Tuebingen (DE); Cécile Gouttefanges, Tuebingen (DE); Toni Weinschenk, Aichwald (DE); Peter Lewandrowski, Tubingen-Unterjesingen (DE)

(73) Assignee: Immatics Biotechnologies GmbH, Tuebingen (DE)

( * ) Notice: Subject to any disclaimer, the term of this patent is extended or adjusted under 35 U.S.C. 154(b) by 857 days.

(21) Appl. No.: 12/466,222

(22) Filed: May 14, 2009

(65) Prior Publication Data

US 2010/0029571 A1    Feb. 4, 2010

Related U.S. Application Data

(60) Provisional application No. 61/053,182, filed on May 14, 2008.

(30) Foreign Application Priority Data

May 14, 2008    (EP) .................................... 08008944

(51) Int. Cl.
| | | |
|---|---|---|
| A61K 38/08 | (2006.01) | |
| A61K 38/10 | (2006.01) | |
| A61K 39/00 | (2006.01) | |
| C07K 14/00 | (2006.01) | |
| C12P 21/00 | (2006.01) | |
| A61K 48/00 | (2006.01) | |

(52) U.S. Cl.
USPC .................. 424/185.1; 424/192.1; 424/277.1; 435/70.1; 435/810; 514/1.1; 514/21.4; 514/21.6; 530/326; 530/350

(58) Field of Classification Search
None
See application file for complete search history.

(56) References Cited

U.S. PATENT DOCUMENTS

| | | | |
|---|---|---|---|
| 6,410,240 | B1 | 6/2002 | Hodge et al. |
| 6,750,321 | B1 * | 6/2004 | Chen et al. ..................... 530/317 |
| 7,811,828 | B2 | 10/2010 | Lemmel et al. |
| 8,008,431 | B2 | 8/2011 | Weinschenk et al. |
| 8,318,677 | B2 * | 11/2012 | Weinschenk et al. ........ 514/19.3 |
| 2002/0061543 | A1 | 5/2002 | Ross |
| 2003/0113733 | A1 | 6/2003 | Khan et al. |
| 2004/0176573 | A1 | 9/2004 | Thor et al. |
| 2005/0063967 | A1 | 3/2005 | Young |
| 2005/0222390 | A1 | 10/2005 | Weinschenk et al. |
| 2009/0004214 | A1 | 1/2009 | Wang et al. |
| 2010/0158929 | A1 * | 6/2010 | Lewandrowski et al. .. 424/185.1 |
| 2012/0107337 | A1 * | 5/2012 | Lewandrowski et al. .. 424/185.1 |

FOREIGN PATENT DOCUMENTS

| | | |
|---|---|---|
| DE | 10225144 | 12/2003 |
| WO | 2004/022709 A2 | 3/2004 |
| WO | 2007/039192 A2 | 4/2007 |

OTHER PUBLICATIONS

Evolutionary Concepts (2003, worldwideweb at ncbi.nlm.nih.gov/bookshelf/br.fcgi?book=sef&part=A22).*
Van der Most et al (J. Immunol. 1996, 157: 5543-5554).*
Swiss-Prot O15392 , 2011.*
Mola et al (J. Mol. Biol. 1007, 366: 1055-1063).*
Uniprot Accession # A3E0Z5 (Mar. 20, 2007).*
Geneseq Accession # AAG02311 (Sep. 6, 2000).*
Van der Most et al (Virology 1998, 240: 158-167).*
Strubin et al (EMBO Journal, 1984, 3(4): 869-872).*
Fournier and Schirrmacher (Expert. Rev. Vaccines 8(1); 51-66, 2009).*
Schrieber et al (Seminar. Immunol. 22: 105-112, 2010).*
Klebanoff et al (Immunol. Rev. 2011, 239: 27-44).*
Engelhard et al (Curr. Opin. Immuno. 1994, 6: 13-23).*
Guo et al (Nature, 1992, 360-364-366).*
Rammensee et al (Immunogenetics, 1995, 41: 178-228).*
McKeon et al (Journal of Neuroscience, 1999, 19(24): 10778-10788).*
Schmitz, Marc et al., "Generation of Survivin-specific CD8 T Effector Cells by Dendritic Cells Pulsed with Protein or Selected Peptides," Cancer Research 60, Sep. 1, 2000, pp. 4845-4849.
Piesche, Matthias, "Identification of a Promiscuous HLA DR-Restricted T-Cell Epitope Derived from the Inhibitor of Apoptosis Protein Survivin," Human Immunology 68, 2007, pp. 572-576.
Charalambous, Anna et al., "Dendritic Cell Targeting of Survivin Protein in a Xenogenic Form Elicits Strong CD4 T Cell Immunity to Mouse Survivin," The Journal of Immunology, 2006, pp. 8410-8421.
Casati, Chiara et al., "The Apoptosis Inhibitor Protein Survivin Induces Tumor-Specific CD8 and CD4 T Cells in Colorectal Cancer Patients," Cancer Research 63, Aug. 1, 2003, pp. 457-4515.
Andersen, Mads Hald, et al., "Spontaneous Cytotoxic T-Cell Responses Against Survivin-Derived MHC Class I-Restricted T-Cell Epitopes in Situ as well as ex Vivo in Cancer Patients," Cancer Research 61, Aug. 15, 2001, pp. 5964-5968.
Feyerbend, Susan, et al., "Novel Multi-Peptide Vaccination in Hla-A2 Hormone Sensitive Patients with Biochemical Relapse of Prostate Cancer," The Prostate, 2009, Wiley-Liss, Inc., pp. 1-11.
Andersen, Mads Hald, et al., "Identification of a Cytotoxic T Lymphocyte Response to the Apoptosis Inhibitor Protein Survivin in Cancer Patients," Cancer Research 61, Feb. 1, 2000, pp. 869-872.

(Continued)

*Primary Examiner* — Gerald R Ewoldt
*Assistant Examiner* — Marianne Dibrino
(74) *Attorney, Agent, or Firm* — Miles & Stockbridge, P.C.

(57) ABSTRACT

The present invention relates to peptides, nucleic acids, and cells for use in the immunotherapy of cancer. The present invention furthermore relates to survivin-derived tumor-associated cytotoxic T cell (CTL) peptide epitopes, alone or in combination with other tumor-associated peptides that serve as active pharmaceutical ingredients of vaccine compositions that stimulate anti-tumor immune responses. The present invention specifically relates to three novel peptide sequences and variants thereof derived from HLA class I and class II molecules of human tumor cells that can be used in vaccine compositions for eliciting anti-tumor immune responses.

8 Claims, 16 Drawing Sheets

(56) References Cited

OTHER PUBLICATIONS

Dejgaard et al., "Identification, Molecular Cloning, Expression and Chromosome Mapping of a Family of Transformation Upregulated hnRNP-K Proteins Derived by Alternative Splicing," J. Mol. Biol., 1994, vol. 236, No. 1, pp. 33-48, XP-002963154.

Flad et al., "Direct Identification of Major Histocompatibility Complex Class I-bound Tumor-associated Peptide Antigens of a Renal Carcinoma Cell Line by a Novel Mass Spectrometric Method," Cancer Research, Dec. 15, 1998, vol. 58, No. 24, pp. 5803-5811, XP-001161018.

Furuya et al., "Expression of regulator of G protein signalling protein 5 (RGS5) in the tumour vasculature of human renal cell carcinoma," Journal of Pathology, Feb. 18, 2004, vol. 203, No. 1, pp. 551-558.

Krueger et al., "Lessons to be learned from primary renal cell carcinomas: novel tumor antigens and HLA ligands for immunotherapy," Cancer Immunol. Immunother., Sep. 2005, vol. 54, No. 9, pp. 826-836, XP-002344048.

Melief et al., "Peptide-based cancer vaccines," Current Opinion in Immunology, 1996, vol. 8, No. 5, pp. 651-657, XP-002344045.

Pucell, et al., "Immunoproteomics: Mass Spectrometry-Based Methods to Study the Targets of the Immune Response," Molecular & Cellular Proteomics, Mar. 2004, vol. 3, No. 3, pp. 193-208, XP-002344046.

Schirle, et al., "Identification of tumor-associated MHC class I ligands by a novel T cell-independent approach," Eur. J. Immunol., Aug. 2000, vol. 30, No. 8, pp. 2216-2225, XP-002246625.

Database Geneseq [Online], "Human Brain Expressed Single Exon Probe Encoded Protein Seq. ID No: 25597," Nov. 5, 2001, XP-002521875, EBI Accession No. GSP: AAM53492, Database Accession No. AAM53492.

Database Geneseq [Online], "Propionibacterium Acnes Immunologenic Protein # 19260," Feb. 27, 2002, XP-002521876, EBI Accession No. GSP: AAU58364, Database Accession No. AAU58364.

Piesche, Matthias, "Identifikation und immunologische Charakterisierung von MHC-Klasse-II-Petideptiopen in Humanen Leukamie und Lymphom assoziierten Antigenen", May 2006, pp. 1-156 (English translation of Sections 1.9, 4.1, 4.1.1, 4.3, 4.3.1, 4.3.2, 4.3.3, Discussion, and Summary included at end), abstract& 4.3.1 only. The remainder not in English language.

Denkberg, Galit et al., "Selective Targeting of Melanoma and APCs Using a Recombinant Antibody with TCR-like Specificity Directed Toward a Melanoma Differentiation Antigen," Journal of Immunology, vol. 171, Issue 5, pp. 2197-2207 (American Association of Immunologists, Sep. 1, 2003).

Cohen, Cyril J. et al., "Direct Phenotypic Analysis of Human MHC Class I Antigen Presentation: Visualization, Quantitation, and In situ Detection of Human Viral Epitopes Using Peptide Specific MHC Restricted Recombinant Antibodies", Journal of Immunology, vol. 170, issue 8, pp. 4349-4361 (American Association of Immunologists, Apr. 15, 2003).

Cohen, Cyril J., et al., "Recombinant Antibodies with MHC-restricted, Peptide-Specific, T-Cell Receptor-like Specificity: New Tools to Study Antigen Production and TCR Peptide MHC Interactions", Journal of Molecular Recognition, vol. 16, Issue 5, pp. 324-332 (John Wiley & Sons, Ltd., Sep. 2003).

Hoffmann, S., et al., "Rapid and sensitive identification of major histocompatibility complex class I-associated tumor peptides by nanoLC Maldi MS/MS", Molecular and Cellular Proteomics, vol. 4, pp. 1888-1897 (The American Society for Biochemistry and Molecular Biology, Aug. 19, 2005).

Lemmel et al., "Differential Quantitative Analysis of MHC Ligands by Mass Spectrometry Using Stable Isotope Labeling", Nature Biotechnology, vol. 22, pp. 450-454 (Nature Publishing Group, Mar. 7, 2004).

Pluschke et al., "Molecular Cloning of a human melanoma associated chondroitin sulfate proteoglycan", Proceedings of the National Academy of Sciences of USA, vol. 93, issue 18, pp. 9710-9715 (National Academy of Sciences, Sep. 3, 1996).

Stevanovic et al., "Generating Data for Databases—the peptide repertoire of HLA molecules", Immunoinformatics: Bioinformatic Strategies for Better Understanding of Immune Function: Novartis Foundation Symposium 254, pp. 143-164, 216-222, and 250-252 (John Wiley and Sons, Ltd., 2003).

Rammensee et al. "SYFPEITHI: database for MHC ligands and peptide motifs", Immunogenetics, vol. 50, pp. 213-219 (Springer, Nov. 1999).

European Patent Office, Extended EP Search Report for EP 08008944.4, pp. 1-6 (Jan. 26, 2009).

WIPO, International Search Report from WO 2005/116051, dated Dec. 8, 2005, entire document.

Jochen Kilgus et al., "Analysis of the Permissive Association of A Malaria T Cell Epitope With DR Molecules," The American Association of Immunologists, The Journal of Immunology, Jan. 1, 1991, vol. 146, pp. 307-315, U.S.A.

Deidre O'Sullivan et al., "Truncation Analysis of Several DR Binding Epitopes," The American Association of Immunologists, The Journal of Immunology, Feb. 15, 1991, vol. 146, pp. 1240-1246, U.S.A.

Xiao-Fei Wang et al., "Comprehensive Analysis of HLA-DR- and HLA-DP4-Restricted CD4+ T Cell Response Specific for the Tumor-Shared Antigen Survivin in Healthy Donors and Cancer Patients," The American Association of Immunologists, The Journal of Immunology, 2008, vol. 181, pp. 431-439.

Melanie Widenmeyer et al., "Promiscuous survivin peptide induces robust CD4+ T-cell responses in the majority of vaccinated cancer patients," International Journal of Cancer, 2012, vol. 131, pp. 140-149.

Third Party Observations Concerning EP 09 745 570.3 Immatics Biotechnologies GmbH dated Jul. 4, 2013, issued by the Kraus & Weisert /Thomas-Wimmer-Ring, Munich, Germany.

* cited by examiner

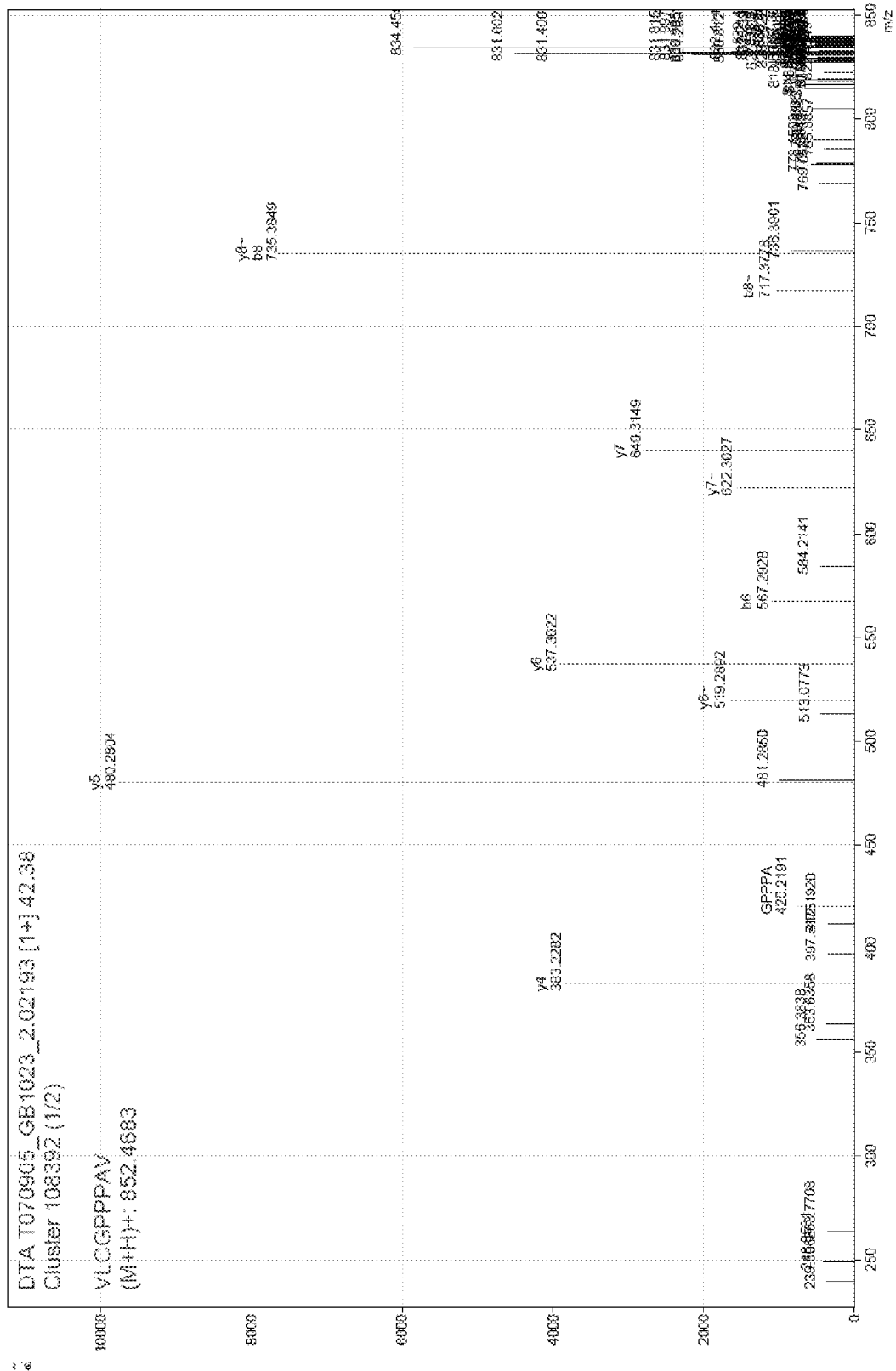
Fig 1: NCAN-001 (GB1023)

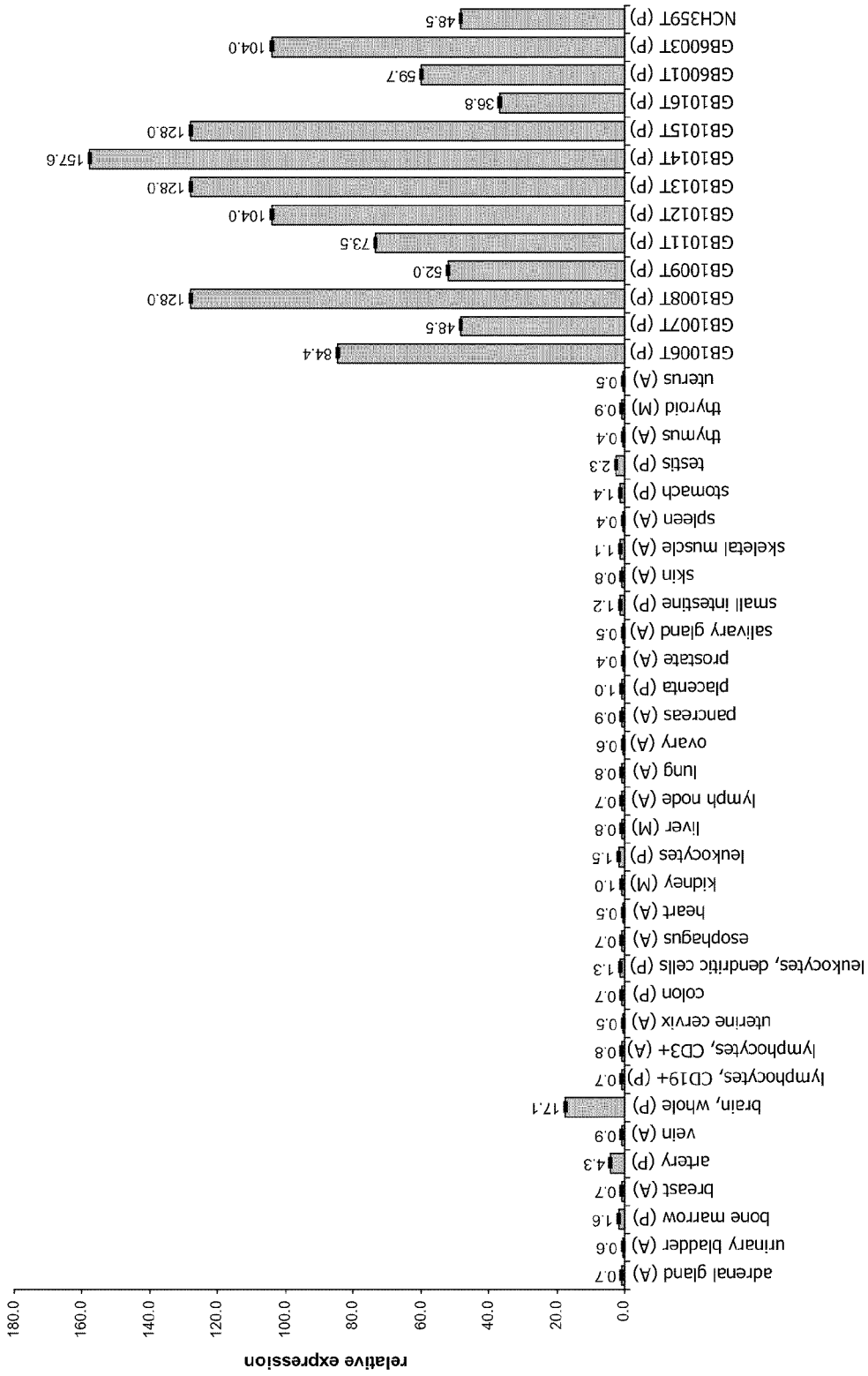
Fig. 2: mRNA Expression profile of NCAN

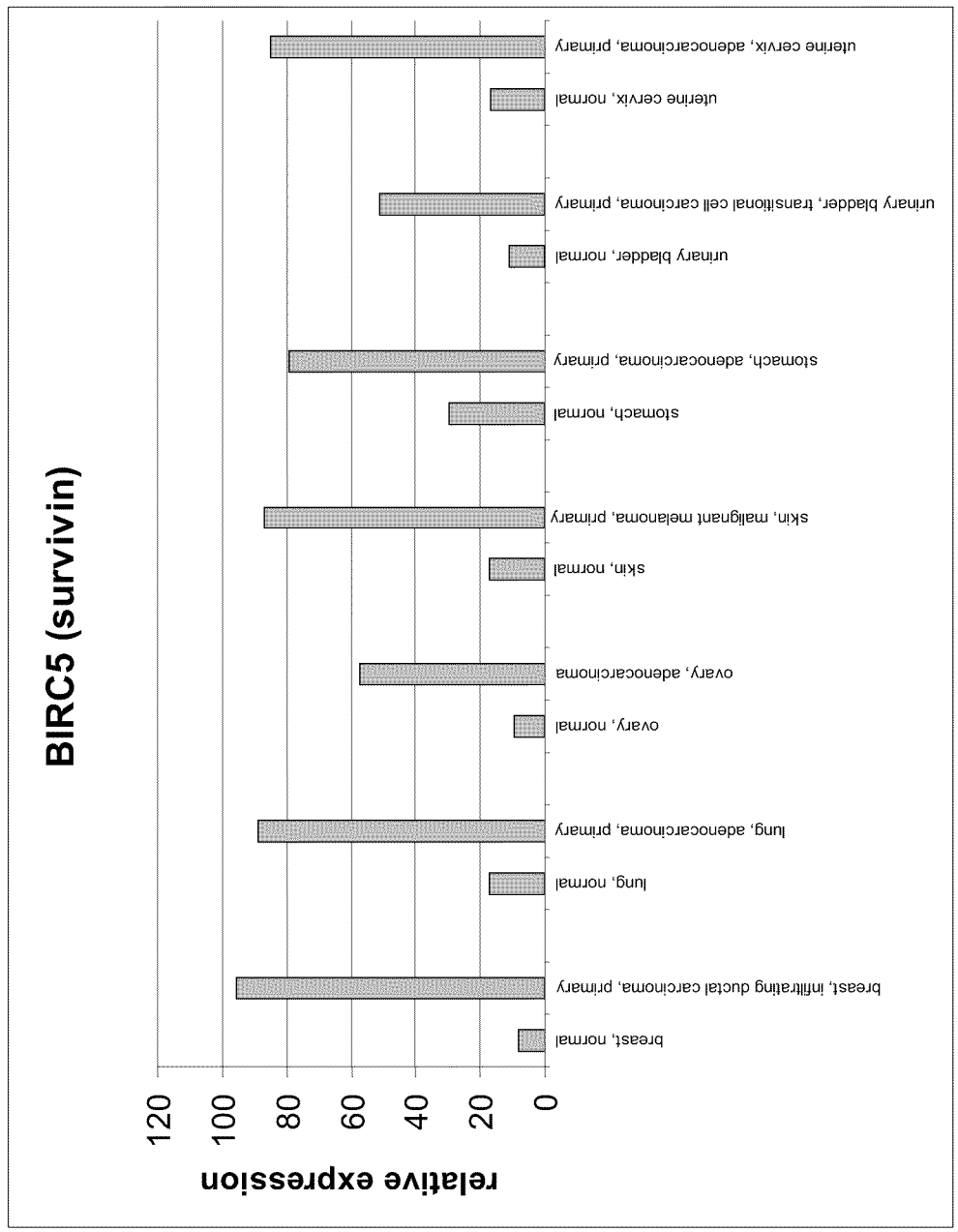
Fig. 3: relative mRNA Expression profile of BIRC5

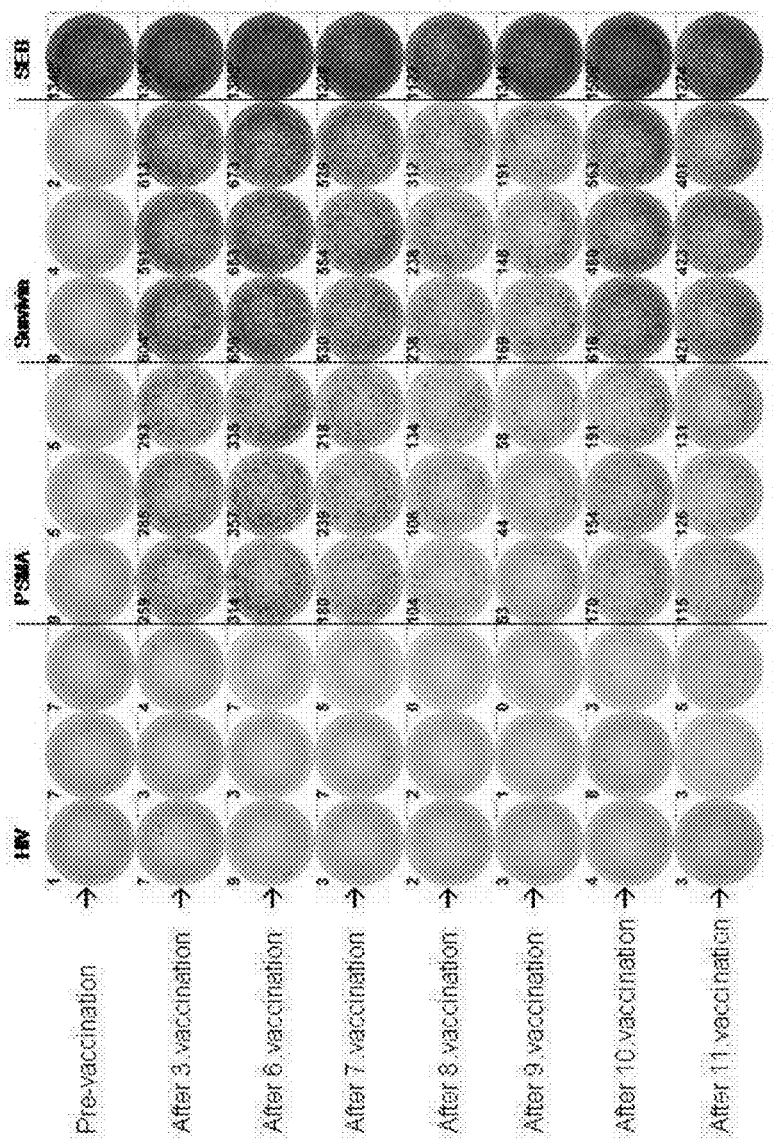
Fig.4a: gamma interferon-ELISpot
The presence of PSMA and Survivin-specific IFNγ-secreting $CD4^+$ T-cells in peripheral blood mononuclear cells (PBMC) from different time points of a vaccinated patient were determined using an IFNγ-EliSpot.

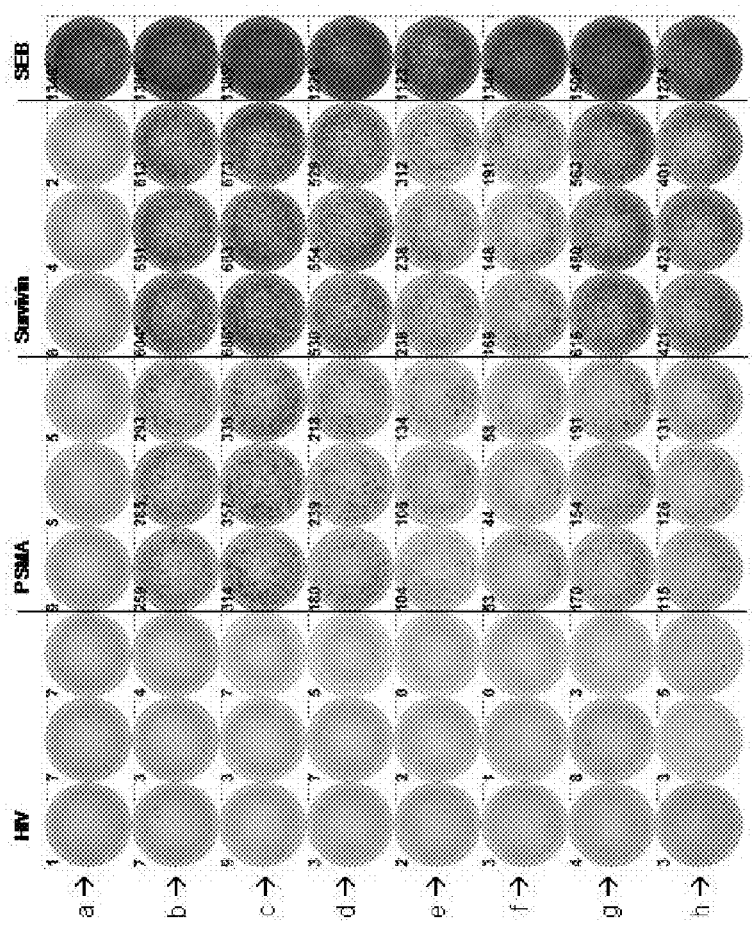
Fig.4b: gamma interferon-ELISpot
The presence of PSMA and Survivin-specific IFNγ-secreting CD4+ T-cells in peripheral blood mononuclear cells (PBMC) from different time points of a vaccinated patient were determined using an IFNγ-EliSpot. Time points: pre-vaccination (a) and after 3.(b), 6.(c), 7.(d), 8.(e), 9.(f). 10.(g), 11.(h) vaccination.

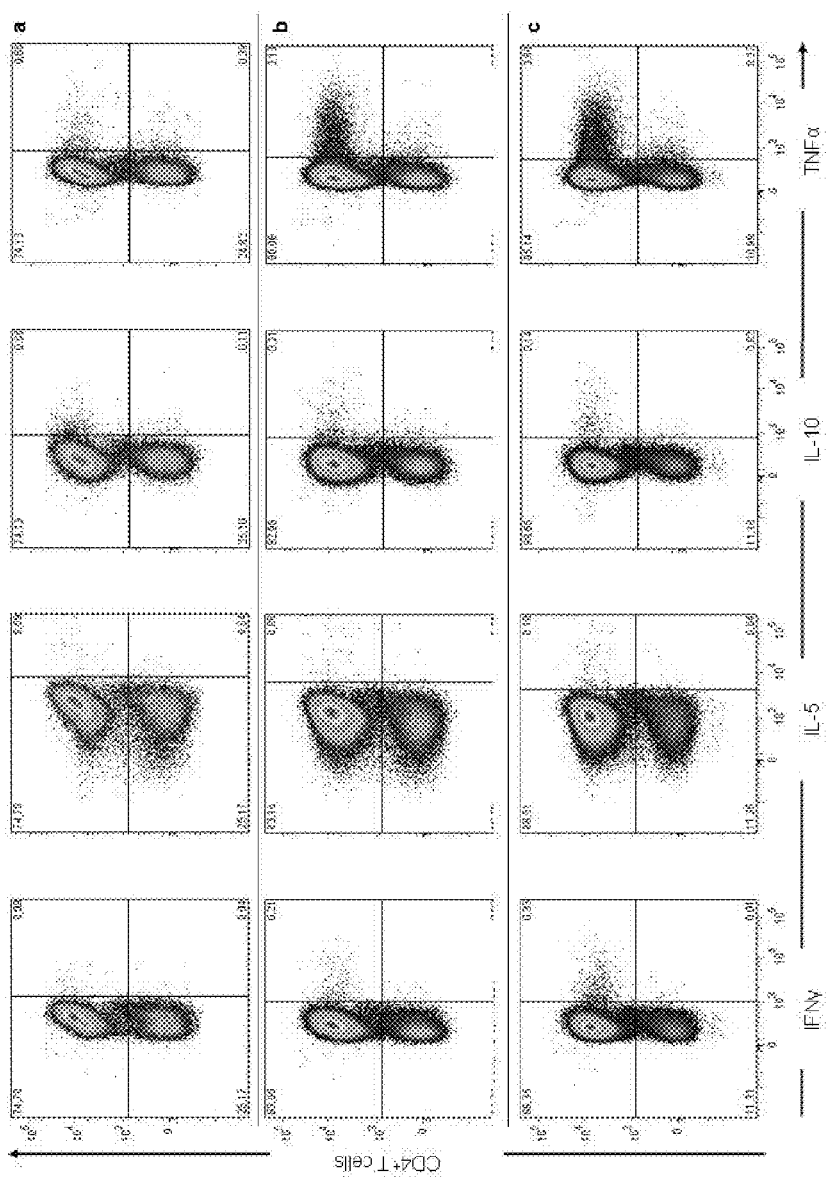
Fig.5: Intracellular staining-Assay (ICS)
The presence of Survivin-specific IFNγ-, IL-5, IL-10, TNFα-secreting CD4+ T-cells in PBMC from three different time points of a vaccinated patient were determined via ICS-Assay. Time points: after 1.(a), 3.(b), 7.(c), vaccination.

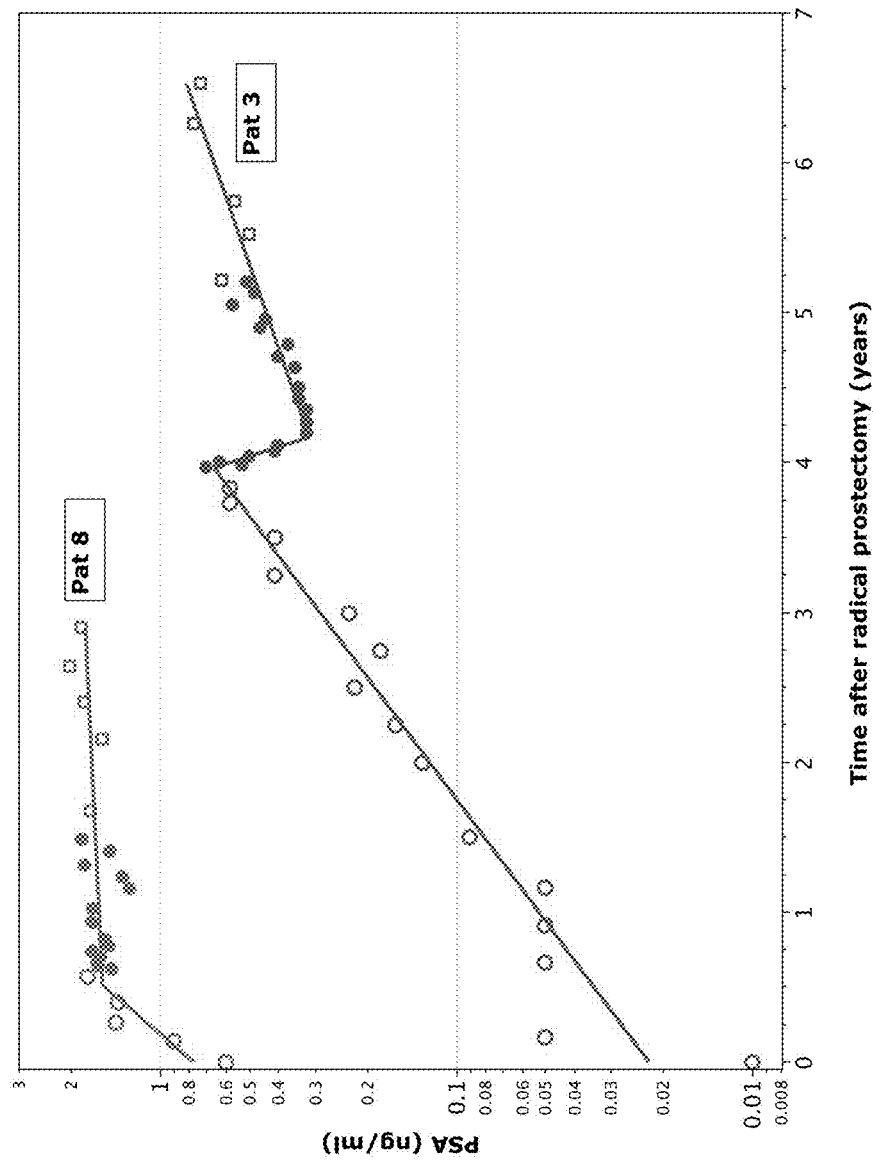
Fig. 6 PSA stability with no rise greater than 10% from baseline PSA

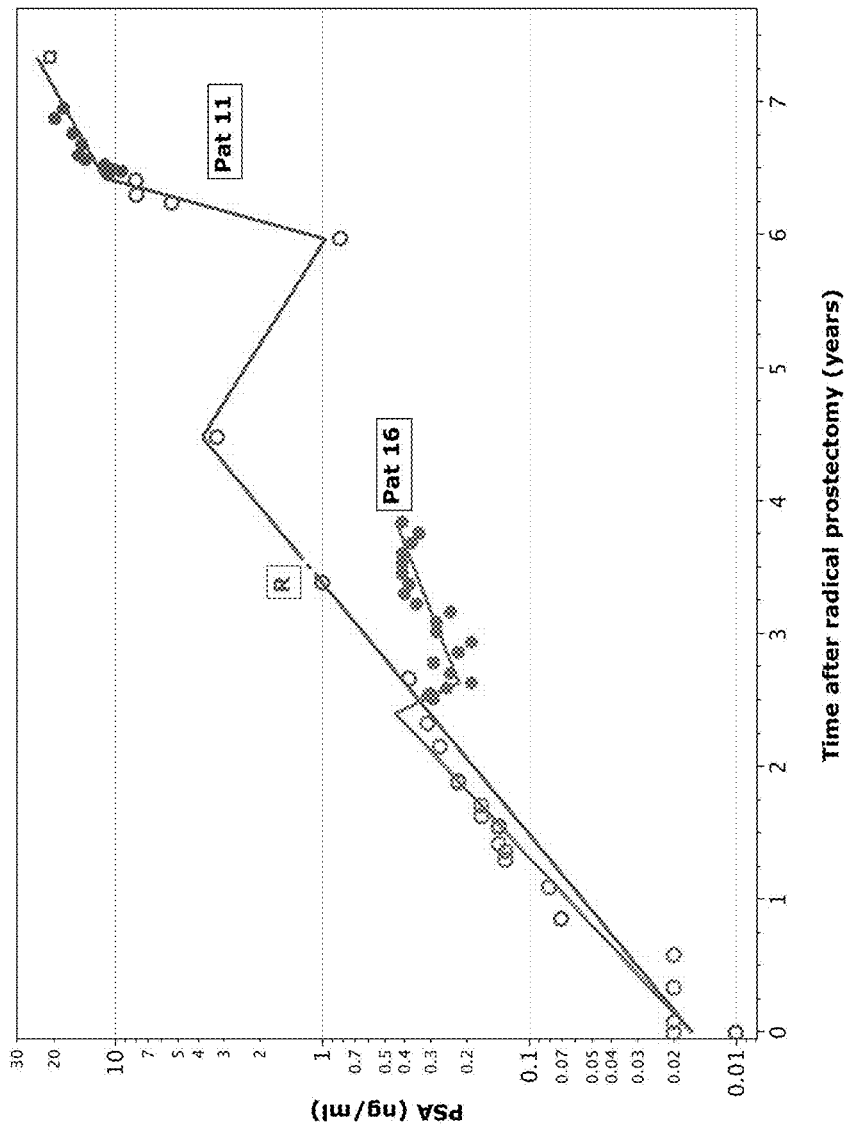
Figure 7. PSA DT increase without PSA stability

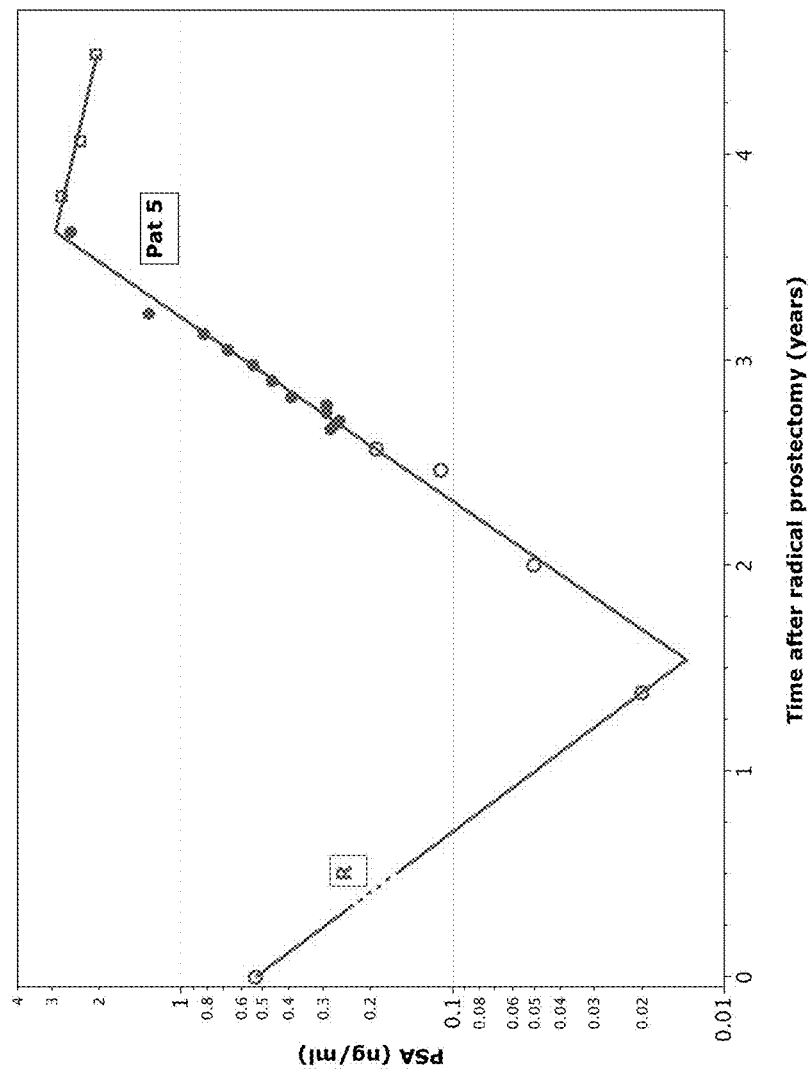
Figure 8. No change of PSA DT in months during vaccination, but decline afterwards

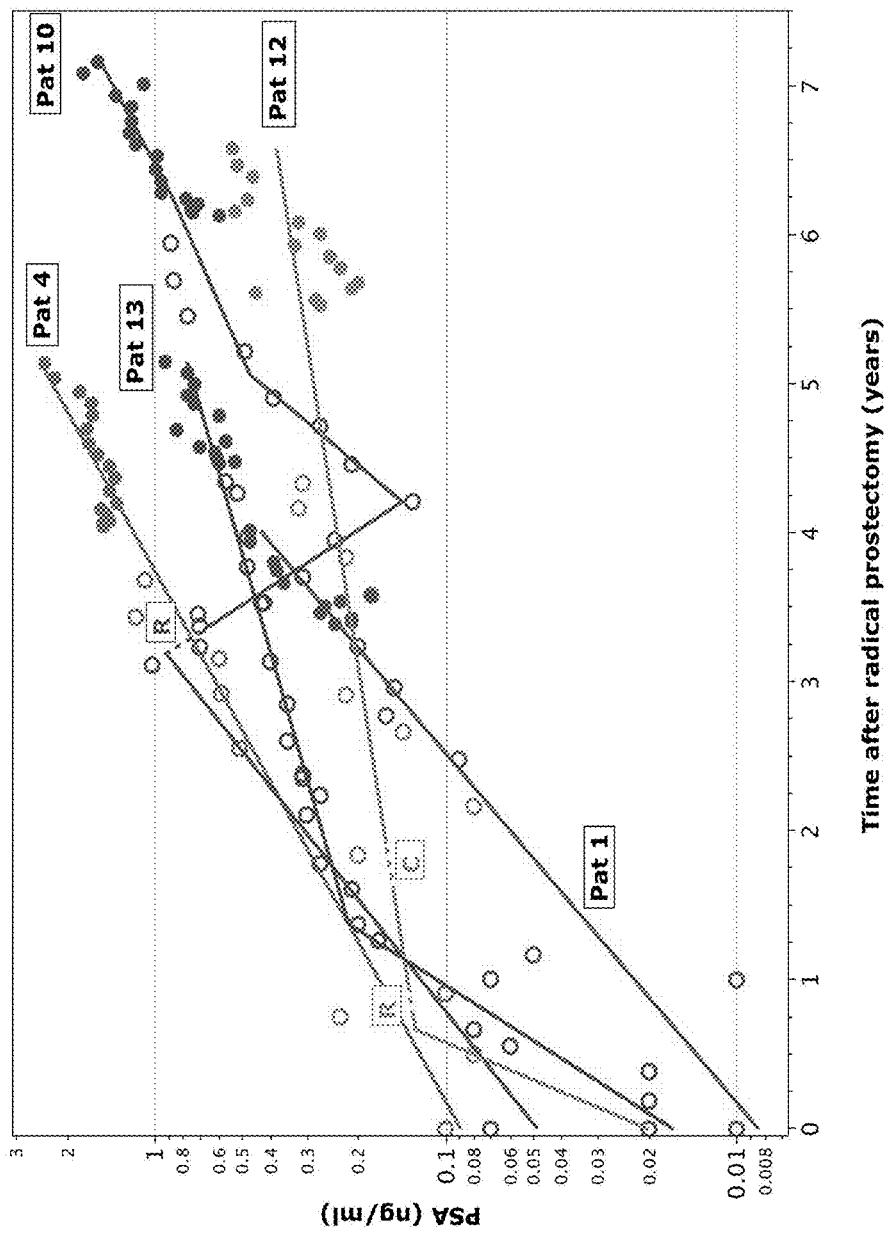
Figure 9. No change of PSA DT during vaccination

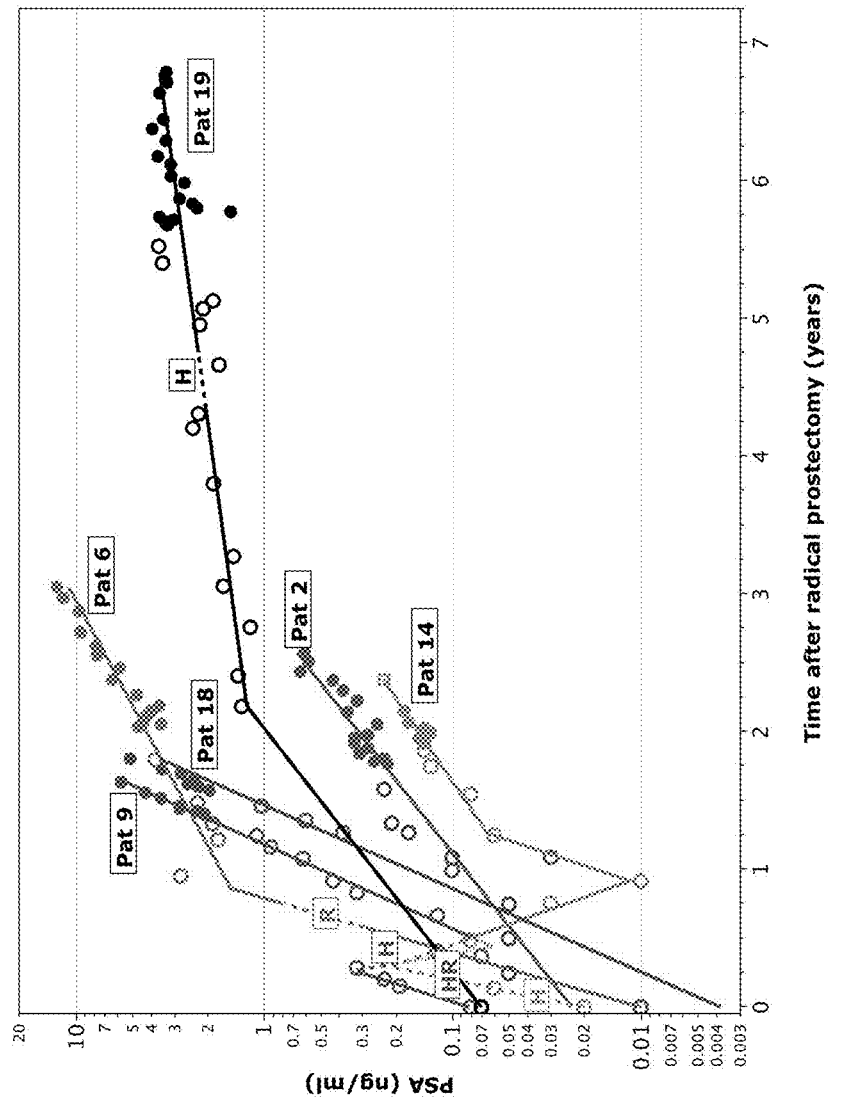
Figure 10. No change of PSA DT during vaccination

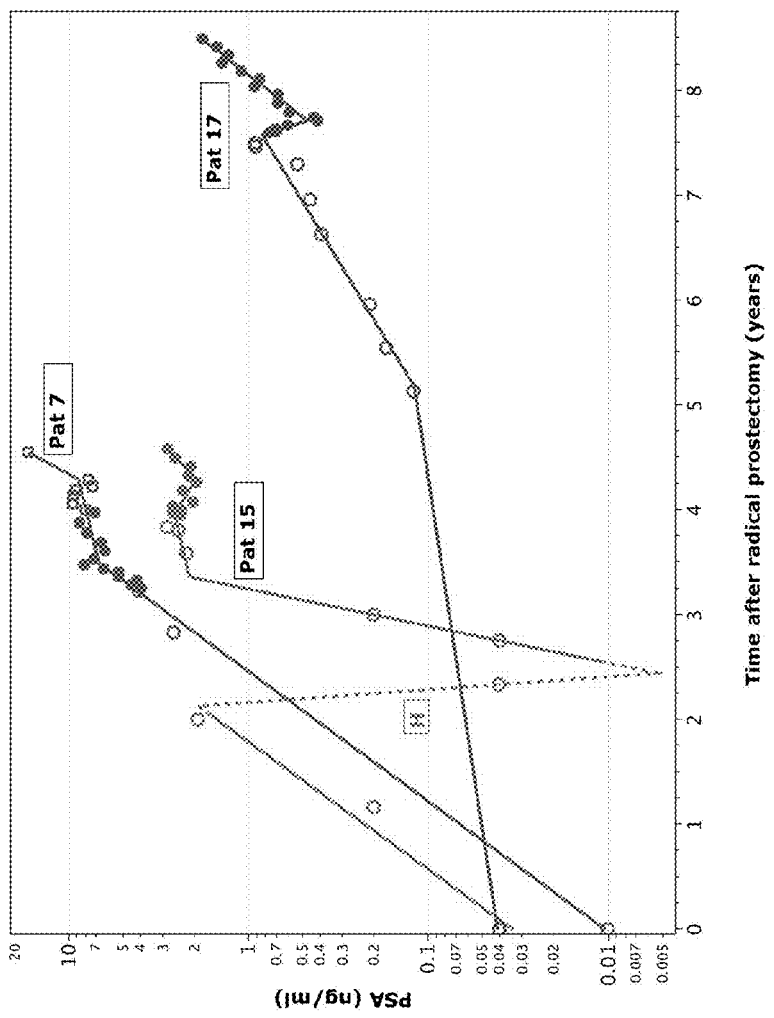
Figure 11. Interim PSA decline or DT increase followed by DT decrease
Figure legend
circle: PSA value prior or after vaccination
dot: PSA value at each vaccination
broken line R: interval of external radiotherapy
broken line H: interval of intermittent hormone therapy
broken line C: interval of taxotere chemotherapy Multifunctional CD4+ T cells
Pro10 11.V

Figure 15.

| | HLA class II typing of cell lines | Pro26 (DR1,DR13,DRB3, DQ5, DQ6) | Pro15 (DR1, DR11, DRB3, DQ3, DQ5) |
|---|---|---|---|
| AL | DR1, DQ1 | +++ | +++ |
| LAM | DQ3, DR4, DP4, DQA1*03 | - | - |
| HO301 | DQ5, DR6, DP19 | +++ | ++ |
| BM15 | DR11, DRB3, DQ3 | +++ | + |
| MGAR | DQ6, DR15, DP4, DW2 | - | - |
| LG2-EBV | DQ5, DRB3, DR14, DR7, DQB1*02 | n.t. | n.t. |
| EMJ | DR13, DQ1, DP3,4, DW19 | n.t. | n.t. |

TNFa responses: (-) < 0,1% CD4+, (+) > 3x control, (++) > 5x control, (+++) > 10x control

SEQUENCE LISTING

<160> NUMBER OF SEQ ID NOS: 83

<210> SEQ ID NO 1
<211> LENGTH: 15
<212> TYPE: PRT
<213> ORGANISM: Homo sapiens

<400> SEQUENCE: 1

Thr Leu Gly Glu Phe Leu Lys Leu Asp Arg Glu Arg Ala Lys Asn
1               5                   10                  15

<210> SEQ ID NO 2
<211> LENGTH: 17

```
<212> TYPE: PRT
<213> ORGANISM: Homo sapiens

<400> SEQUENCE: 2

Glu Leu Thr Leu Gly Glu Phe Leu Lys Leu Asp Arg Glu Arg Ala Lys
1               5                   10                  15

Asn

<210> SEQ ID NO 3
<211> LENGTH: 15
<212> TYPE: PRT
<213> ORGANISM: Homo sapiens

<400> SEQUENCE: 3

Thr Leu Gly Glu Phe Leu Lys Leu Asp Arg Glu Arg Ala Lys Asp
1               5                   10                  15

<210> SEQ ID NO 4
<211> LENGTH: 16
<212> TYPE: PRT
<213> ORGANISM: Homo sapiens

<400> SEQUENCE: 4

Ser Gln Asp Asp Ile Lys Gly Ile Gln Lys Leu Tyr Gly Lys Arg Ser
1               5                   10                  15

<210> SEQ ID NO 5
<211> LENGTH: 9
<212> TYPE: PRT
<213> ORGANISM: Homo sapiens

<400> SEQUENCE: 5

Val Met Ala Gly Asp Ile Tyr Ser Val
1               5

<210> SEQ ID NO 6
<211> LENGTH: 9
<212> TYPE: PRT
<213> ORGANISM: Homo sapiens

<400> SEQUENCE: 6

Ser Val Ala Ser Thr Ile Thr Gly Val
1               5

<210> SEQ ID NO 7
<211> LENGTH: 9
<212> TYPE: PRT
<213> ORGANISM: Homo sapiens

<400> SEQUENCE: 7

Ala Leu Ala Asp Gly Val Gln Lys Val
1               5

<210> SEQ ID NO 8
<211> LENGTH: 9
<212> TYPE: PRT
<213> ORGANISM: Homo sapiens

<400> SEQUENCE: 8

Leu Leu Gly Ala Thr Cys Met Phe Val
1               5

<210> SEQ ID NO 9
<211> LENGTH: 9
<212> TYPE: PRT
```

-continued

<213> ORGANISM: Homo sapiens

<400> SEQUENCE: 9

Ser Val Phe Ala Gly Val Val Gly Val
1               5

<210> SEQ ID NO 10
<211> LENGTH: 9
<212> TYPE: PRT
<213> ORGANISM: Homo sapiens

<400> SEQUENCE: 10

Ala Leu Phe Asp Gly Asp Pro His Leu
1               5

<210> SEQ ID NO 11
<211> LENGTH: 9
<212> TYPE: PRT
<213> ORGANISM: Homo sapiens

<400> SEQUENCE: 11

Tyr Val Asp Pro Val Ile Thr Ser Ile
1               5

<210> SEQ ID NO 12
<211> LENGTH: 9
<212> TYPE: PRT
<213> ORGANISM: Homo sapiens

<400> SEQUENCE: 12

Ser Thr Ala Pro Pro Val His Asn Val
1               5

<210> SEQ ID NO 13
<211> LENGTH: 9
<212> TYPE: PRT
<213> ORGANISM: Homo sapiens

<400> SEQUENCE: 13

Leu Ala Ala Leu Pro His Ser Cys Leu
1               5

<210> SEQ ID NO 14
<211> LENGTH: 10
<212> TYPE: PRT
<213> ORGANISM: Homo sapiens

<400> SEQUENCE: 14

Phe Leu Pro Ser Asp Phe Phe Pro Ser Val
1               5                   10

<210> SEQ ID NO 15
<211> LENGTH: 9
<212> TYPE: PRT
<213> ORGANISM: Homo sapiens

<400> SEQUENCE: 15

Ala Leu Ser Asn Leu Glu Val Thr Leu
1               5

<210> SEQ ID NO 16
<211> LENGTH: 9
<212> TYPE: PRT
<213> ORGANISM: Homo sapiens

<400> SEQUENCE: 16

```
Ile Leu Ala Pro Val Ile Leu Tyr Ile
1               5
```

<210> SEQ ID NO 17
<211> LENGTH: 9
<212> TYPE: PRT
<213> ORGANISM: Homo sapiens

<400> SEQUENCE: 17

```
Ile Leu Asp Gln Lys Ile Asn Glu Val
1               5
```

<210> SEQ ID NO 18
<211> LENGTH: 10
<212> TYPE: PRT
<213> ORGANISM: Homo sapiens

<400> SEQUENCE: 18

```
Lys Leu Met Asp Leu Asp Val Glu Gln Leu
1               5                   10
```

<210> SEQ ID NO 19
<211> LENGTH: 10
<212> TYPE: PRT
<213> ORGANISM: Homo sapiens

<400> SEQUENCE: 19

```
Ala Leu Phe Val Arg Leu Leu Ala Leu Ala
1               5                   10
```

<210> SEQ ID NO 20
<211> LENGTH: 10
<212> TYPE: PRT
<213> ORGANISM: Homo sapiens

<400> SEQUENCE: 20

```
Lys Ile Phe Asp Glu Ile Leu Val Asn Ala
1               5                   10
```

<210> SEQ ID NO 21
<211> LENGTH: 15
<212> TYPE: PRT
<213> ORGANISM: Homo sapiens

<400> SEQUENCE: 21

```
Thr Pro Pro Ile Asp Ala His Thr Arg Asn Leu Leu Arg Asn His
1               5                   10                  15
```

<210> SEQ ID NO 22
<211> LENGTH: 16
<212> TYPE: PRT
<213> ORGANISM: Homo sapiens

<400> SEQUENCE: 22

```
Ser Pro Gln Tyr Ser Trp Arg Ile Asn Gly Ile Pro Gln Gln His Thr
1               5                   10                  15
```

<210> SEQ ID NO 23
<211> LENGTH: 9
<212> TYPE: PRT
<213> ORGANISM: Homo sapiens

<400> SEQUENCE: 23

```
Tyr Leu Ser Gly Ala Asn Leu Asn Leu
1               5
```

<210> SEQ ID NO 24
<211> LENGTH: 9
<212> TYPE: PRT
<213> ORGANISM: Homo sapiens

<400> SEQUENCE: 24

Val Leu Cys Gly Pro Pro Pro Ala Val
1               5

<210> SEQ ID NO 25
<211> LENGTH: 15
<212> TYPE: PRT
<213> ORGANISM: Homo sapiens

<400> SEQUENCE: 25

Leu Thr Leu Gly Glu Phe Leu Lys Leu Asp Arg Glu Arg Ala Lys
1               5                   10                  15

<210> SEQ ID NO 26
<211> LENGTH: 15
<212> TYPE: PRT
<213> ORGANISM: Homo sapiens

<400> SEQUENCE: 26

Gly Glu Phe Leu Lys Leu Asp Arg Glu Arg Ala Lys Asn Lys Ile
1               5                   10                  15

<210> SEQ ID NO 27
<211> LENGTH: 15
<212> TYPE: PRT
<213> ORGANISM: Homo sapiens

<400> SEQUENCE: 27

Leu Lys Leu Asp Arg Glu Arg Ala Lys Asn Lys Ile Ala Lys Glu
1               5                   10                  15

<210> SEQ ID NO 28
<211> LENGTH: 15
<212> TYPE: PRT
<213> ORGANISM: Homo sapiens

<400> SEQUENCE: 28

Trp Gln Pro Phe Leu Lys Asp His Arg Ile Ser Thr Phe Lys Asn
1               5                   10                  15

<210> SEQ ID NO 29
<211> LENGTH: 15
<212> TYPE: PRT
<213> ORGANISM: Homo sapiens

<400> SEQUENCE: 29

Phe Lys Asn Trp Pro Phe Leu Glu Gly Ala Ala Ala Thr Pro Glu
1               5                   10                  15

<210> SEQ ID NO 30
<211> LENGTH: 15
<212> TYPE: PRT
<213> ORGANISM: Homo sapiens

<400> SEQUENCE: 30

Glu Ala Gly Phe Ile His Ala Pro Thr Glu Asn Glu Pro Asp Leu
1               5                   10                  15

<210> SEQ ID NO 31

```
<211> LENGTH: 15
<212> TYPE: PRT
<213> ORGANISM: Homo sapiens

<400> SEQUENCE: 31

Phe Phe Cys Phe Lys Glu Leu Glu Gly Trp Glu Pro Asp Asp Asp
1               5                   10                  15

<210> SEQ ID NO 32
<211> LENGTH: 16
<212> TYPE: PRT
<213> ORGANISM: Homo sapiens

<400> SEQUENCE: 32

Leu Gly Glu Phe Leu Lys Leu Asp Arg Glu Arg Ala Lys Asn Lys Ile
1               5                   10                  15

<210> SEQ ID NO 33
<211> LENGTH: 15
<212> TYPE: PRT
<213> ORGANISM: Homo sapiens

<400> SEQUENCE: 33

Lys Asn Lys Ile Ala Lys Glu Thr Asn Asn Lys Lys Lys Glu Phe
1               5                   10                  15

<210> SEQ ID NO 34
<211> LENGTH: 15
<212> TYPE: PRT
<213> ORGANISM: Homo sapiens

<400> SEQUENCE: 34

Phe Phe Cys Phe Lys Glu Leu Glu Gly Trp Glu Pro Asp Asp Asp
1               5                   10                  15

<210> SEQ ID NO 35
<211> LENGTH: 15
<212> TYPE: PRT
<213> ORGANISM: Homo sapiens

<400> SEQUENCE: 35

Leu Gly Glu Phe Leu Lys Leu Asp Arg Glu Arg Ala Lys Asn Lys
1               5                   10                  15

<210> SEQ ID NO 36
<211> LENGTH: 15
<212> TYPE: PRT
<213> ORGANISM: Homo sapiens

<400> SEQUENCE: 36

Phe Lys Asn Trp Pro Phe Leu Glu Gly Cys Ala Cys Thr Pro Glu
1               5                   10                  15

<210> SEQ ID NO 37
<211> LENGTH: 15
<212> TYPE: PRT
<213> ORGANISM: Homo sapiens

<400> SEQUENCE: 37

Gly Glu Phe Leu Lys Leu Asp Arg Glu Arg Ala Lys Asn Lys Ile
1               5                   10                  15

<210> SEQ ID NO 38
<211> LENGTH: 15
<212> TYPE: PRT
<213> ORGANISM: Homo sapiens
```

```
<400> SEQUENCE: 38

Trp Gln Pro Phe Leu Lys Asp His Arg Ile Ser Thr Phe Lys Asn
1               5                   10                  15

<210> SEQ ID NO 39
<211> LENGTH: 15
<212> TYPE: PRT
<213> ORGANISM: Homo sapiens

<400> SEQUENCE: 39

Ala Pro Thr Leu Pro Pro Ala Trp Gln Pro Phe Leu Lys Asp His
1               5                   10                  15

<210> SEQ ID NO 40
<211> LENGTH: 15
<212> TYPE: PRT
<213> ORGANISM: Homo sapiens

<400> SEQUENCE: 40

Leu Gly Glu Phe Leu Lys Leu Asp Arg Glu Arg Ala Lys Asn Lys
1               5                   10                  15

<210> SEQ ID NO 41
<211> LENGTH: 15
<212> TYPE: PRT
<213> ORGANISM: Homo sapiens

<400> SEQUENCE: 41

Trp Gln Pro Phe Leu Lys Asp His Arg Ile Ser Thr Phe Lys Asn
1               5                   10                  15

<210> SEQ ID NO 42
<211> LENGTH: 15
<212> TYPE: PRT
<213> ORGANISM: Homo sapiens

<400> SEQUENCE: 42

Ala Pro Thr Leu Pro Pro Ala Trp Gln Pro Phe Leu Lys Asp His
1               5                   10                  15

<210> SEQ ID NO 43
<211> LENGTH: 15
<212> TYPE: PRT
<213> ORGANISM: Homo sapiens

<400> SEQUENCE: 43

Lys Lys Glu Phe Glu Glu Thr Ala Glu Lys Val Arg Arg Ala Ile
1               5                   10                  15

<210> SEQ ID NO 44
<211> LENGTH: 15
<212> TYPE: PRT
<213> ORGANISM: Homo sapiens

<400> SEQUENCE: 44

Ala Glu Lys Val Arg Arg Ala Ile Glu Gln Leu Ala Ala Met Asp
1               5                   10                  15

<210> SEQ ID NO 45
<211> LENGTH: 15
<212> TYPE: PRT
<213> ORGANISM: Homo sapiens

<400> SEQUENCE: 45
```

```
Ala Pro Thr Leu Pro Pro Ala Trp Gln Pro Phe Leu Lys Asp His
1               5                   10                  15
```

<210> SEQ ID NO 46
<211> LENGTH: 15
<212> TYPE: PRT
<213> ORGANISM: Homo sapiens

<400> SEQUENCE: 46

```
Asp His Arg Ile Ser Thr Phe Lys Asn Trp Pro Phe Leu Glu Gly
1               5                   10                  15
```

<210> SEQ ID NO 47
<211> LENGTH: 15
<212> TYPE: PRT
<213> ORGANISM: Homo sapiens

<400> SEQUENCE: 47

```
Leu Glu Gly Cys Ala Cys Thr Pro Glu Arg Met Ala Glu Ala Gly
1               5                   10                  15
```

<210> SEQ ID NO 48
<211> LENGTH: 15
<212> TYPE: PRT
<213> ORGANISM: Homo sapiens

<400> SEQUENCE: 48

```
Glu Ala Gly Phe Ile His Cys Pro Thr Glu Asn Glu Pro Asp Leu
1               5                   10                  15
```

<210> SEQ ID NO 49
<211> LENGTH: 15
<212> TYPE: PRT
<213> ORGANISM: Homo sapiens

<400> SEQUENCE: 49

```
Phe Glu Glu Leu Thr Leu Gly Glu Phe Leu Lys Leu Asp Arg Glu
1               5                   10                  15
```

<210> SEQ ID NO 50
<211> LENGTH: 15
<212> TYPE: PRT
<213> ORGANISM: Homo sapiens

<400> SEQUENCE: 50

```
Lys Leu Asp Arg Glu Arg Ala Lys Asn Lys Ile Ala Lys Glu Thr
1               5                   10                  15
```

<210> SEQ ID NO 51
<211> LENGTH: 15
<212> TYPE: PRT
<213> ORGANISM: Homo sapiens

<400> SEQUENCE: 51

```
Leu Gly Glu Phe Leu Lys Leu Asp Arg Glu Arg Ala Lys Asn Lys
1               5                   10                  15
```

<210> SEQ ID NO 52
<211> LENGTH: 15
<212> TYPE: PRT
<213> ORGANISM: Homo sapiens

<400> SEQUENCE: 52

```
Gly Cys Ala Phe Leu Ser Val Lys Lys Gln Phe Glu Glu Leu Thr
1               5                   10                  15
```

<210> SEQ ID NO 53
<211> LENGTH: 15
<212> TYPE: PRT
<213> ORGANISM: Homo sapiens

<400> SEQUENCE: 53

Phe Phe Cys Phe Lys Glu Leu Glu Gly Trp Glu Pro Asp Asp Asp
1               5                   10                  15

<210> SEQ ID NO 54
<211> LENGTH: 15
<212> TYPE: PRT
<213> ORGANISM: Homo sapiens

<400> SEQUENCE: 54

Glu Leu Thr Leu Gly Glu Phe Leu Lys Leu Asp Arg Glu Arg Ala
1               5                   10                  15

<210> SEQ ID NO 55
<211> LENGTH: 15
<212> TYPE: PRT
<213> ORGANISM: Homo sapiens

<400> SEQUENCE: 55

Ile Ser Thr Phe Lys Asn Trp Pro Phe Leu Glu Gly Cys Ala Cys
1               5                   10                  15

<210> SEQ ID NO 56
<211> LENGTH: 15
<212> TYPE: PRT
<213> ORGANISM: Homo sapiens

<400> SEQUENCE: 56

Ala Gln Cys Phe Phe Cys Phe Lys Glu Leu Glu Gly Trp Glu Pro
1               5                   10                  15

<210> SEQ ID NO 57
<211> LENGTH: 9
<212> TYPE: PRT
<213> ORGANISM: Homo sapiens

<400> SEQUENCE: 57

Phe Leu Lys Leu Asp Arg Glu Arg Ala
1               5

<210> SEQ ID NO 58
<211> LENGTH: 9
<212> TYPE: PRT
<213> ORGANISM: Homo sapiens

<400> SEQUENCE: 58

Leu Lys Leu Asp Arg Glu Arg Ala Lys
1               5

<210> SEQ ID NO 59
<211> LENGTH: 9
<212> TYPE: PRT
<213> ORGANISM: Homo sapiens

<400> SEQUENCE: 59

Phe Leu Lys Leu Asp Arg Glu Arg Ala
1               5

<210> SEQ ID NO 60
<211> LENGTH: 9

```
<212> TYPE: PRT
<213> ORGANISM: Homo sapiens

<400> SEQUENCE: 60

Phe Leu Lys Leu Asp Arg Glu Arg Ala
1               5

<210> SEQ ID NO 61
<211> LENGTH: 9
<212> TYPE: PRT
<213> ORGANISM: Homo sapiens

<400> SEQUENCE: 61

Leu Gly Glu Phe Leu Lys Leu Asp Arg
1               5

<210> SEQ ID NO 62
<211> LENGTH: 13
<212> TYPE: PRT
<213> ORGANISM: Homo sapiens

<400> SEQUENCE: 62

Leu Gly Glu Phe Leu Lys Leu Asp Arg Glu Arg Ala Lys
1               5                   10

<210> SEQ ID NO 63
<211> LENGTH: 14
<212> TYPE: PRT
<213> ORGANISM: Homo sapiens

<400> SEQUENCE: 63

Thr Leu Gly Glu Phe Leu Lys Leu Asp Arg Glu Arg Ala Lys
1               5                   10

<210> SEQ ID NO 64
<211> LENGTH: 15
<212> TYPE: PRT
<213> ORGANISM: Homo sapiens

<400> SEQUENCE: 64

Asn Tyr Thr Leu Arg Val Asp Cys Thr Pro Leu Met Tyr Ser Leu
1               5                   10                  15

<210> SEQ ID NO 65
<211> LENGTH: 18
<212> TYPE: PRT
<213> ORGANISM: Human immunodeficiency virus

<400> SEQUENCE: 65

Tyr Val Asp Arg Phe Tyr Lys Thr Leu Arg Ala Glu Gln Ala Ser Gln
1               5                   10                  15

Glu Val

<210> SEQ ID NO 66
<211> LENGTH: 9
<212> TYPE: PRT
<213> ORGANISM: Homo sapiens

<400> SEQUENCE: 66

Arg Leu Tyr Asn Phe Ser Phe Leu Asn
1               5

<210> SEQ ID NO 67
<211> LENGTH: 9
<212> TYPE: PRT
```

<213> ORGANISM: Homo sapiens

<400> SEQUENCE: 67

Tyr Ala Asp Gly Gly Gln Trp Tyr Asn
1               5

<210> SEQ ID NO 68
<211> LENGTH: 9
<212> TYPE: PRT
<213> ORGANISM: Homo sapiens

<400> SEQUENCE: 68

Lys Leu Asp Arg Glu Arg Ala Lys Asn
1               5

<210> SEQ ID NO 69
<211> LENGTH: 10
<212> TYPE: PRT
<213> ORGANISM: Homo sapiens

<400> SEQUENCE: 69

Leu Lys Leu Asp Arg Glu Arg Ala Lys Asn
1               5                   10

<210> SEQ ID NO 70
<211> LENGTH: 8
<212> TYPE: PRT
<213> ORGANISM: Homo sapiens

<400> SEQUENCE: 70

Leu Asp Arg Glu Arg Ala Lys Asn
1               5

<210> SEQ ID NO 71
<211> LENGTH: 10
<212> TYPE: PRT
<213> ORGANISM: Homo sapiens

<400> SEQUENCE: 71

Phe Leu Pro Ser Asp Tyr Phe Pro Ser Val
1               5                   10

<210> SEQ ID NO 72
<211> LENGTH: 9
<212> TYPE: PRT
<213> ORGANISM: Homo sapiens

<400> SEQUENCE: 72

Lys Leu Asp Arg Glu Arg Ala Lys Asp
1               5

<210> SEQ ID NO 73
<211> LENGTH: 9
<212> TYPE: PRT
<213> ORGANISM: Homo sapiens

<400> SEQUENCE: 73

Val Met Cys Gly Pro Pro Pro Ala Leu
1               5

<210> SEQ ID NO 74
<211> LENGTH: 9
<212> TYPE: PRT
<213> ORGANISM: Homo sapiens

<400> SEQUENCE: 74

```
Val Ile Cys Gly Pro Pro Ala Leu
1               5
```

<210> SEQ ID NO 75
<211> LENGTH: 9
<212> TYPE: PRT
<213> ORGANISM: Homo sapiens

<400> SEQUENCE: 75

```
Val Leu Cys Glu Pro Pro Lys Val
1               5
```

<210> SEQ ID NO 76
<211> LENGTH: 9
<212> TYPE: PRT
<213> ORGANISM: Homo sapiens

<400> SEQUENCE: 76

```
Ile Leu Ala Gly Ile Ile Ala Glu Val
1               5
```

<210> SEQ ID NO 77
<211> LENGTH: 9
<212> TYPE: PRT
<213> ORGANISM: Homo sapiens

<400> SEQUENCE: 77

```
Leu Leu Tyr Pro Lys Leu Tyr Ala Val
1               5
```

<210> SEQ ID NO 78
<211> LENGTH: 9
<212> TYPE: PRT
<213> ORGANISM: Homo sapiens

<400> SEQUENCE: 78

```
Phe Leu Phe Thr Tyr Thr His Ala Val
1               5
```

<210> SEQ ID NO 79
<211> LENGTH: 9
<212> TYPE: PRT
<213> ORGANISM: Homo sapiens

<400> SEQUENCE: 79

```
Lys Leu Pro Gly Asn Pro Pro Ala Val
1               5
```

<210> SEQ ID NO 80
<211> LENGTH: 9
<212> TYPE: PRT
<213> ORGANISM: Homo sapiens

<400> SEQUENCE: 80

```
Val Met Cys Met Pro Phe Pro Ala Val
1               5
```

<210> SEQ ID NO 81
<211> LENGTH: 9
<212> TYPE: PRT
<213> ORGANISM: Homo sapiens

<400> SEQUENCE: 81

```
Tyr Leu Ser Gly Val Pro Pro Ala Val
1               5
```

```
<210> SEQ ID NO 82
<211> LENGTH: 9
<212> TYPE: PRT
<213> ORGANISM: Homo sapiens

<400> SEQUENCE: 82

Val Leu Arg Gly Pro Pro Pro Ala Val
1               5

<210> SEQ ID NO 83
<211> LENGTH: 9
<212> TYPE: PRT
<213> ORGANISM: Homo sapiens

<400> SEQUENCE: 83

Val Met Cys Gly Pro Pro Pro Ala Leu
1               5
```

POWERFUL MHC-CLASS II PEPTIDES DERIVED FROM SURVIVIN

RELATED APPLICATIONS

This application claims priority to U.S. provisional application No. 61/053,182, filed on May 14, 2008 and EP application 08 008944.4, filed on May 14, 2008, both of which are herein incorporated by reference in their entirety.

FIELD OF THE INVENTION

The present invention relates to peptides, nucleic acids, and cells for use in immunotherapeutic methods. In particular, the present invention relates to the immunotherapy of cancer. The present invention furthermore relates to survivin-derived tumor-associated cytotoxic T cell (CTL) peptide epitopes, alone or in combination with other tumor-associated peptides that serve as active pharmaceutical ingredients of vaccine compositions that stimulate anti-tumor immune responses. The present invention specifically relates to three novel peptide sequences and variants thereof derived from HLA class I and class II molecules of human tumor cells that can be used in vaccine compositions for eliciting anti-tumor immune responses.

BACKGROUND OF THE INVENTION

Gliomas are brain tumors originating from glial cells in the nervous system. Glial cells, commonly called neuroglia or simply glia, are non-neuronal cells that provide support and nutrition, maintain homeostasis, form myelin, and participate in signal transmission in the nervous system. The two most important subgroups of gliomas are astrocytomas and oligodendrogliomas, named according to the normal glial cell type from which they originate (astrocytes or oligodendrocytes, respectively). Belonging to the subgroup of astrocytomas, glioblastoma multiforme (referred to as glioblastoma hereinafter) is the most common malignant brain tumor in adults and accounts for approximately 40% of all malignant brain tumors and approximately 50% of gliomas (CBTRUS, 2006). It aggressively invades the central nervous system and is ranked at the highest malignancy level (grade IV) among all gliomas. Although there has been steady progress in treatment due to improvements in neuroimaging, microsurgery, diverse treatment options, such as temozolomide or radiation, glioblastomas remain incurable (Macdonald, 2001; Burton and Prados, 2000; Prados and Levin, 2000). The lethality rate of this brain tumor is very high: the average life expectancy is 9 to 12 months after first diagnosis. The 5-year survival rate during the observation period from 1986 to 1990 was 8.0%. To date, the five-year survival rate following aggressive therapy including gross tumor resection is still less than 10% (Burton and Prados, 2000; Nieder et al., 2000; Napolitano et al., 1999; Dazzi et al., 2000). Accordingly, there is a strong medical need for an alternative and effective therapeutic method.

Tumor cells of glioblastomas are the most undifferentiated cells among brain tumors. Thus, the tumor cells have high potential of migration and proliferation and are highly invasive, leading to very poor prognosis. Glioblastomas lead to death due to rapid, aggressive, and infiltrative growth in the brain. The infiltrative growth pattern is responsible for the unresectable nature of these tumors. Glioblastomas are also relatively resistant to radiation and chemotherapy, and, therefore, post-treatment recurrence rates are high. In addition, the immune response to the neoplastic cells is rather ineffective in completely eradicating all neoplastic cells following resection and radiation therapy (Roth and Weller, 1999; Dix et al., 1999; Sablotzki et al., 2000).

Glioblastoma is classified into primary glioblastoma (de novo) and secondary glioblastoma, depending on differences in the gene mechanism during malignant transformation of undifferentiated astrocytes or glial precursor cells. Secondary glioblastoma occurs in a younger population of up to 45 years of age. During 4 to 5 years, on average, secondary glioblastoma develops from lower-grade astrocytoma through undifferentiated astrocytoma. In contrast, primary glioblastoma predominantly occurs in an older population with a mean age of 55 years. Generally, primary glioblastoma occurs as fulminant glioblastoma characterized by tumor progression within 3 months from the state with no clinical or pathological abnormalities (Pathology and Genetics of the Nervous Systems. 29-39 (IARC Press, Lyon, France, 2000)).

Glioblastoma migrates along myelinated nerves and spreads widely in the central nervous system. In most cases surgical treatment shows only limited sustainable therapeutic effect (Neurol. Med. Chir. (Tokyo) 34, 91-94, 1994; Neurol. Med. Chir. (Tokyo) 33, 425-458, 1993; Neuropathology 17, 186-188, 1997) (Macdonald, 2001; Prados and Levin, 2000).

Malignant glioma cells evade detection by the host's immune system by producing immunosuppressive agents that impair T cell proliferation and production of the immune-stimulating cytokine IL-2 (Dix et al., 1999).

Intracranial neoplasms can arise from any of the structures or cell types present in the central nervous system (CNS), including the brain, meninges, pituitary gland, skull, and even residual embryonic tissue. The overall annual incidence of primary brain tumors in the United States is 14 cases per 100,000. The most common primary brain tumors are meningiomas, representing 27% of all primary brain tumors, and glioblastomas, representing 23% of all primary brain tumors (whereas glioblastomas account for 40% of malignant brain tumor in adults). Many of these tumors are aggressive and are of high grade. Primary brain tumors are the most common solid tumors in children and the second most frequent cause of cancer death, after leukemia, in children.

The search for effective treatment of glioblastomas in patients is still ongoing today. Immunotherapy, or treatment via recruitment of the immune system, to fight these neoplastic cells has been investigated. First encouraging results were obtained by Northwest Therapeutics using "DCVax Brain" for the treatment of glioblastoma in immuno-therapeutic studies in humans, in which antigen-specific cytotoxic lymphocyte (CTL) responses could be induced leading to prolonged median survival times compared to that obtained applying standard treatment. Further this treatment was accompanied by minimal toxicity (Heimberger et al., 2006).

Colorectal Carcinoma

According to the American Cancer Society, colorectal cancer (CRC) is the third most common cancer in the US afflicting more than 175,000 new patients each year. In the US, Japan, France, Germany, Italy, Spain and the U K it affects more than 480,000 patients. It is one of the most common causes of cancer mortality in developed countries. The 1- and 5-year relative survival for persons with colorectal cancer is 84% and 64%, respectively. Survival continues to decline beyond 5 years. For instance at 10 years after diagnosis survival is 57%. When colorectal cancers are detected at an early, localized stage, the 5-year survival is 90%; however, only 39% of colorectal cancers are diagnosed at this stage, mostly due to low rates of screening. After the cancer has spread regionally to involve adjacent organs or lymph nodes, the 5-year survival drops to 68%. For persons with distant metastases, 5-year survival is 10%.

Research suggests that the onset of colorectal cancer is the result of interactions between inherited and environmental factors. In most cases, adenomatous polyps appear to be precursors to colorectal tumors; however the transition may take many years. The primary risk factor for colorectal cancer is age, with 90% of cases diagnosed over the age of 50 years. Other risk factors for colorectal cancer according to the American Cancer Society include alcohol consumption, a diet high in fat and/or red meat and an inadequate intake of fruits and vegetables. Incidence continues to rise, especially in areas such as Japan, where the adoption of westernized diets with excess fat and meat intake and a decrease in fiber intake may be to blame. However, incidence rates are rising not as fast as previously, which may be due to increasing screening and polyp removal, thus preventing progression of polyps to cancer.

As in most solid tumors, first line treatment is surgery, however, its benefits remain confined to early-stage patients. A significant proportion of patients are diagnosed in advanced stages of the disease. For advanced colorectal cancer chemotherapy, regimens based on fluorouracil-based regimens are standard of care. The majority of these regimens are the so-called FOLFOX (infusional 5-FU/leucovorin plus oxaliplatin) and FOLFIRI (irinotecan, leucovorin, bolus and continuous-infusion 5-FU) protocols.

The introduction of third-generation cytotoxics such as irinotecan and oxaliplatin has raised the hope of significantly improving efficacy, but prognosis is still relatively poor, and the survival rate generally remains at approximately 20 months in metastatic disease and, as a result, the unmet needs in the disease remain high.

Recently, a novel generation of drugs, molecular-targeted agents, such as AVASTIN® (bevacizumab) and ERBITUX® (cetuximab), became available, and about 40 compounds are in late-stage clinical development for different stages of colorectal cancer. Combinations of several of these compounds increase the number of potential treatment options to be expected for the future. The vast majority of substances are in phase II, with the EGFR being addressed by these compounds more often than any other target in colorectal cancer trials, which is due to the fact that in ~80% of patients with colorectal cancer, EGFR expression is upregulated.

Clinical trials with stage II patients combining chemotherapy with the recently approved monoclonal antibodies (mAbs) (cetuximab+irinotecan or FOLFOX4; bevacizumab as a single-agent or together with FOLFOX4) are currently being conducted. Three to four year observation periods are expected for statistically significant results from these trials.

Monoclonal antibodies (mAbs) presently used in oncology in general have an excellent chance of not interfering with active immunotherapy. In fact, there is preclinical (GABRILOVICH 1999) and clinical evidence suggesting that depletion of VEGF (by bevacizumab) contributes positively to DC-mediated activation of T-cells (Osada T, Chong G, Tansik R, Hong T, Spector N, Kumar R, Hurwitz H I, Dev I, Nixon A B, Lyerly H K, Clay T, Morse M A. The effect of anti-VEGF therapy on immature myeloid cell and dendritic cells in cancer patients. Cancer Immunol Immunother. 2008 Jan. 10.).

Prostate Carcinoma and Other Tumors

With an estimated 27,050 deaths in 2007, prostate cancer is a leading cause of cancer death in men. Although death rates have been declining among white and African American men since the early 1990s, rates in African American men remain more than twice as high as those in white men. Prostate cancer is the most frequently diagnosed cancer in men. For reasons that remain unclear, incidence rates are significantly higher in African American men than in white men. Incidence rates of prostate cancer have changed substantially over the last 20 years: rapidly increasing from 1988-1992, declining sharply from 1992-1995, and increasing modestly since 1995. These trends in large part reflect increased prostate cancer screening with the prostate-specific antigen (PSA) blood test. Moderate incidence increases in the last decade are most likely attributable to widespread PSA screening among men younger than 65. Prostate cancer incidence rates have leveled off in men aged 65 years and older. Rates peaked in white men in 1992 (237.6 per 100,000 men) and in African American men in 1993 (342.8 per 100,000 men).

Treatment for prostate cancer may involve watchful waiting, surgery, radiation therapy, High Intensity Focused Ultrasound (HIFU), chemotherapy, cryosurgery, hormonal therapy, or some combination. The best option depends on the stage of the disease, the Gleason score, and the PSA level. Other important factors are the man's age, his general health, and his feelings about potential treatments and their possible side effects. Because all treatments can have significant side effects, such as erectile dysfunction and urinary incontinence, treatment discussions often focus on balancing the goals of therapy with the risks of lifestyle alterations.

If the cancer has spread beyond the prostate, treatment options significantly change, so most doctors who treat prostate cancer use a variety of nomograms to predict the probability of spread. Treatment by watchful waiting, HIFU, radiation therapy, cryosurgery, and surgery are generally offered to men whose cancer remains within the prostate. Hormonal therapy and chemotherapy are often reserved for disease that has spread beyond the prostate. However, there are exceptions: radiation therapy may be used for some advanced tumors, and hormonal therapy is used for some early stage tumors. Cryotherapy, hormonal therapy, and chemotherapy may also be offered if initial treatment fails and the cancer progresses.

In a significant number of patients with prostate carcinoma who undergo radical prostatectomy because of clinically suspected organ-limited growth, a definitive histological workup of the surgical preparation shows a locally extensive tumor extending beyond the borders of the organ. These patients have a high risk for early local recurrence, usually detectable as increasing PSA level in terms of a biochemical relapse. Therapeutic options in this situation include external radiotherapy and hormone ablation; however, the value of these therapeutic approaches, especially with respect to prolonging the patient's long-term survival, must not be regarded as proven. In addition, possible treatment-associated complications such as the development of urethral strictures (radiotherapy), loss of libido and impotence, the risk of a reduction in skeletal calcium salts in terms of osteoporosis, and a markedly increased risk of pathologic bone fractures (hormone ablation) must be considered.

More than 90% of all prostate cancers are discovered in the local and regional stages; the 5-year relative survival rate for patients whose tumors are diagnosed at these stages approaches 100%. Over the past 25 years, the 5-year survival rate for all stages combined has increased from 69% to nearly 90%. According to the most recent data, relative 10-year survival is 93% and 15-year survival is 77%. The dramatic improvements in survival, particularly at 5 years, are partly attributable to earlier diagnosis and improvements in treatment. Nevertheless, the survival rate drops significantly after spreading to other tissues and organs.

Lung Cancer

Estimated 210,000 new cases are expected in 2007 in the USA, accounting for about 15% of cancer diagnoses. The incidence rate is declining significantly in men, from a high of 102 cases per 100,000 in 1984 to 78.5 in 2003. In women, the rate is approaching a plateau after a long period of increase. Lung cancer is classified clinically as small cell (13%) or non-small cell (87%) for the purposes of treatment.

Lung cancer accounts for the most cancer-related deaths in both men and women. An estimated 160,390 deaths, accounting for about 29% of all cancer deaths, are expected to occur in 2007. Since 1987, more women have died each year from lung cancer than from breast cancer. Death rates have continued to decline significantly in men from 1991-2003 by about 1.9% per year. Female lung cancer death rates are approaching a plateau after continuously increasing for several decades. These trends in lung cancer mortality reflect the decrease in smoking rates over the past 30 years.

Treatment options are determined by the type (small cell or non-small cell) and stage of cancer and include surgery, radiation therapy, chemotherapy, and targeted biological therapies such as bevacizumab (AVASTIN®) and erlotinib (TARCEVA®). For localized cancers, surgery is usually the treatment of choice. Recent studies indicate that survival with early-stage, non-small cell lung cancer is improved by chemotherapy following surgery. Because the disease has usually spread by the time it is discovered, radiation therapy and chemotherapy are often used, sometimes in combination with surgery. Chemotherapy alone or combined with radiation is the usual treatment of choice for small cell lung cancer. However with this regimen, a large percentage of patients experience remission, which is long lasting in some cases.

The 1-year relative survival for lung cancer has slightly increased from 37% in 1975-1979 to 42% in 2002, largely due to improvements in surgical techniques and combined therapies. However, the 5-year survival rate for all stages combined is only 16%. The survival rate is 49% for cases detected when the disease is still localized; however, only 16% of lung cancers are diagnosed at this early stage.

carcinoma, lung cancer, CNS, ovarian, melanoma (Tamm et al. 1998) pancreatic cancer, squamous cell carcinoma, leukemia and medulloblastoma and other tumors that show an overexpression of survivin, as well as enhancing the well-being of the patients without using chemotherapeutic agents or other agents which may lead to severe side effects.

SUMMARY OF THE INVENTION

In a first aspect thereof, the present invention relates to a peptide comprising a sequence selected from the group of SEQ ID NO: 1 to SEQ ID NO: 3, or a variant thereof that is at least 85% homologous to SEQ ID NO: 1 to SEQ ID NO: 3, or a variant thereof that induces T cells cross-reacting with said variant peptide; wherein said peptide is not the full-length polypeptide of human survivin. Preferably, said peptide is selected from a peptide having a specific HLA-subtype, such as HLA-A*02 or HLA-DR.

In a second aspect thereof, the present invention relates to a nucleic acid, encoding a peptide according to the present invention or an expression vector capable of expressing said nucleic acid.

In a third aspect thereof, the present invention relates to a host cell comprising the nucleic acid or the expression vector according to the present invention, wherein the host cell preferably is an antigen presenting cell, in particular a dendritic cell or antigen presenting cell.

In a fourth aspect, the present invention relates to an in vitro method for producing activated cytotoxic T lymphocytes (CTL), comprising contacting in vitro CTL with antigen loaded human class I MHC molecules expressed on the surface of a suitable antigen-presenting cell or an artificial construct mimicking an antigen-presenting cell for a period of time sufficient to activate the CTL in an antigen specific manner, wherein the antigen is a peptide according to the present invention.

The present invention also provides a use of a peptide, the nucleic acid, the expression vector, the host cell, or an activated cytotoxic T lymphocyte produced according to the

TABLE 1

Estimated new cancer cases and deaths by sex for the US in 2007 (American Cancer Society. Cancer Facts & Figures 2007. Atlanta: American Cancer Society; 2007.)

| Sites | Estimated New Cases | | | Estimated Deaths | | |
|---|---|---|---|---|---|---|
| | Both Sexes | Male | Female | Both Sexes | Male | Female |
| Glioma and Brain | 20,500 | 11,170 | 9,330 | 12,740 | 7,150 | 5,590 |
| Breast | 180,510 | 2,030 | 178,480 | 40,910 | 450 | 40,460 |
| Prostate | 218,890 | 218,890 | | 27,050 | 27,050 | |
| Esophagus | 15,560 | 12,130 | 3,430 | 13,940 | 10,900 | 3,040 |
| Colon | 112,340 | 55,290 | 57,050 | 52,180 | 26,000 | 26,180 |
| Renal | 51,190 | 31,590 | 19,600 | 12,890 | 8,080 | 4,810 |
| Pancreas | 37,170 | 18,830 | 18,340 | 33,370 | 16,840 | 16,530 |
| Squamous cell carcinomas; Keratinocytic neoplasms of the skin | 1,000,000 | n.d. | n.d. | n.d. | n.d. | n.d. |
| Leukemia | 44,240 | 24,800 | 19,440 | 21,790 | 12,320 | 9,470 |
| Lung | 213,380 | 114,760 | 98,620 | 160,390 | 89,510 | 70,880 |
| Non-Hodgkins Lymphoma | 63,190 | 34,210 | 28,990 | 18,660 | 9,600 | 9,060 |
| Ovarian | 22,430 | | 22,430 | 15,280 | | 15,280 |
| Melanoma | 59,940 | 33,910 | 26,030 | 8,110 | 5,220 | 2,890 |

There thus remains a need for new efficacious and safe treatment option for glioblastoma, prostate tumor, breast cancer, esophageal cancer, colorectal cancer, clear cell renal cell present invention for the treatment of cancer or for the manufacture of a medicament against cancer. The medicament is preferably a vaccine. Preferably, the cancer is selected from astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, teratoma, gangliogliomas, gangliocytoma, central gangliocytoma, primitive neuroectodermal tumors (PNET, e.g. medulloblastoma, medulloepithelioma, neuroblastoma, retinoblastoma, ependymoblastoma), tumors of the pineal parenchyma (e.g. pineocytoma, pineoblastoma), ependymal cell tumors, choroid plexus tumors, neuroepithelial tumors of uncertain origin (e.g. gliomatosis cerebri, astroblastoma), glioblastoma prostate tumor, breast cancer, esophageal cancer, colon cancer, colorectal cancer, renal cell carcinoma, clear cell renal cell carcinoma, lung cancer, CNS, ovarian, melanoma pancreatic cancer, squamous cell carcinoma, leukemia and medulloblastoma, and other tumors or cancers showing an overexpression of Survivin.

The present invention also provides a kit, comprising: (a) a container that contains a pharmaceutical composition containing a peptide, a the nucleic acid or the expression vector according to a host cell, or an activated cytotoxic T lymphocyte according to the present invention, in solution or in lyophilized form; (b) optionally, a second container containing a diluent or reconstituting solution for the lyophilized formulation; (c) optionally, at least one peptide selected from the group consisting of the peptides according to SEQ ID NOS: 4 to 24, and (d) optionally, instructions for the use of the solution and/or the reconstitution and/or use of the lyophilized formulation.

The present invention also provides a method for producing a recombinant antibody that specifically binds to a human major histocompatibility complex (MHC) class I or II complexed with a HLA-restricted antigen. The method comprises immunizing a genetically engineered non-human mammal having cells that expresses a human major histocompatibility complex (MHC) class I or II. The non-human mammal is immunized with a soluble form of a MHC class I or II molecule complexed with a HLA-restricted antigen. mRNA molecules are isolated from antibody producing cells of the non-human mammal. A phage display library displaying protein molecules encoded by the mRNA molecules is provided. At least one phage is isolated from the phage display library, wherein the at least one phage displaying the antibody specifically binds to the human major histocompatibility complex (MHC) class I or II complexed with the HLA-restricted antigen.

The present invention further provides an antibody that specifically binds to a human major histocompatibility complex (MHC) class I or II complexed with a HLA-restricted antigen, wherein the antibody is preferably is a polyclonal antibody, monoclonal antibody and/or a chimeric antibody.

BRIEF DESCRIPTION OF THE DRAWINGS

FIG. 1 shows the ESI-liquid chromatography mass spectrum identifying the tumor associated peptide NCAN-001 from the glioblastoma sample GB1006.

FIG. 2 depicts the mRNA expression profile of the gene NCAN encoding the glioblastoma associated peptide NCAN-001. Expression of this gene is absent or very low in normal tissues while it is strongly increased in glioblastoma samples (GB1006T to GB1011T; NCH359T and NCH361T).

FIG. 3 depicts the relative mRNA expression profile of the gene BIRC.5 Expression of this gene is absent or very low in normal tissues while it is strongly increased in tumor samples.

FIGS. 4*a* and 4*b* depict the presence of PSMA and Survivin-specific IFNγ-secreting CD4$^+$ T-cells in peripheral blood mononuclear cells (PBMC) from different time points of a vaccinated patient which were determined using an IFNγ-ELISPOT®. Time points: pre-vaccination (a) and after 3.(b), 6.(c), 7.(d), 8.(e), 9.(f), 10.(g), 11.(h) vaccination.

FIG. 5 shows the presence of Survivin-specific IFNγ, IL-5, IL-10, TNFα-secreting CD4$^+$ T-cells in PBMC from three different time points of a vaccinated patient that were determined via ICS-Assay. Time points: after 1.(a), 3.(b), 7.(c), vaccination.

FIG. 6 shows the biochemical response in patients 8 and 10, showing PSA stability with no rise greater than 10% from baseline PSA.

FIG. 7 shows the biochemical response in patients II and 16, showing PSA DT increase without PSA stability.

FIG. 8 shows the biochemical response in patient 5, showing PSA DT increase without PSA stability.

FIG. 9 shows the biochemical response in patients 1, 4, 10, 12 and 13 showing no change of PSA DT during vaccination.

FIG. 10 shows the biochemical response in patients 2, 6, 9, 14, 18 and 19 showing no change of PSA DT during vaccination.

FIG. 11 shows the biochemical response in patients 7, 15 and 17 showing interim PSA decline or DT increase followed by DT decrease.

FIG. 15 shows that several tumor cell lines expressing different HLA-DR alleles are recognized by patient-derived PBMCs (shown for the patients Pro26 and Pro15). Patients develop multi-clonal T-cell responses after vaccination with BIR-002. BIR-002 shows promiscuous binding to several HLA class II alleles: DR1; (see also Wang et al.); DQ5 (not tested by Wang et al.); DR11 (see also Wang et al.); or DRB3 (in contrast to Wang et al., 2008, Table 1). Functional presentation of BIR-002 is possible in the context of several HLA class II molecules (TNF-alpha production). As for HLA class I (HLA-A, -B, C), in principle, also three different gene loci can be found for HLA class II that express functional class II molecules on the cell surface, namely HLA-DQ, HLA-DP and HLA-DR. Class I molecules are composed of a heavy chain (-A, -B, -C) and a beta-2-microglobulin that is constant in all three genes. Nevertheless, class II molecules are composed of two each of variable chains (alpha und beta). Thus, sophisticated genetically typing is always complicated with class II. In the table so-called serologic types are given, which are based on antibody binding. Thus, "DQ3" for example comprises different alleles of HLA-DQ alpha and beta chains that are commonly found together and react with a particular antibody. The cells in the table are:

Figure 12:
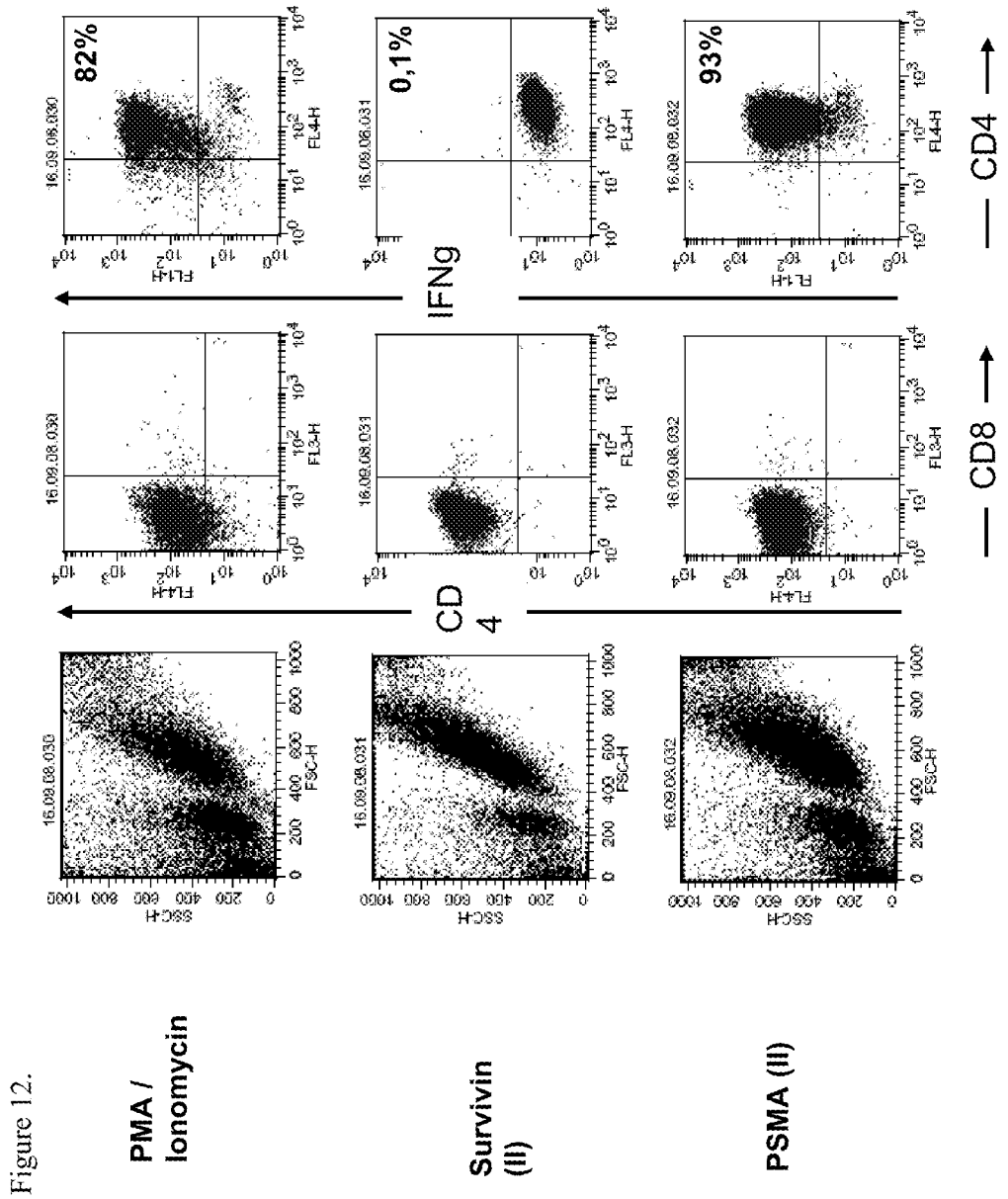
FIG. 12 shows that from the prostate cancer vaccination study, BIR-002-peptide-specific CD4+ T-cell clones could be established from several vaccinated cancer patients that are functional with respect to IFN-gamma production in response to BIR-002. Wang et al., 2008 describe T-cell clones obtained from healthy donors only after several rounds of in vitro priming and stimulation, while the present T-cells can be induced in patients by vaccinations. PMA/ionomycin=antigen-independent unspecific activation; Survivin (II): BIR-002 stimulation; PSMA (II): stimulation with irrelevant peptide. All reactive cells are CD4 positive.
Figure 13:
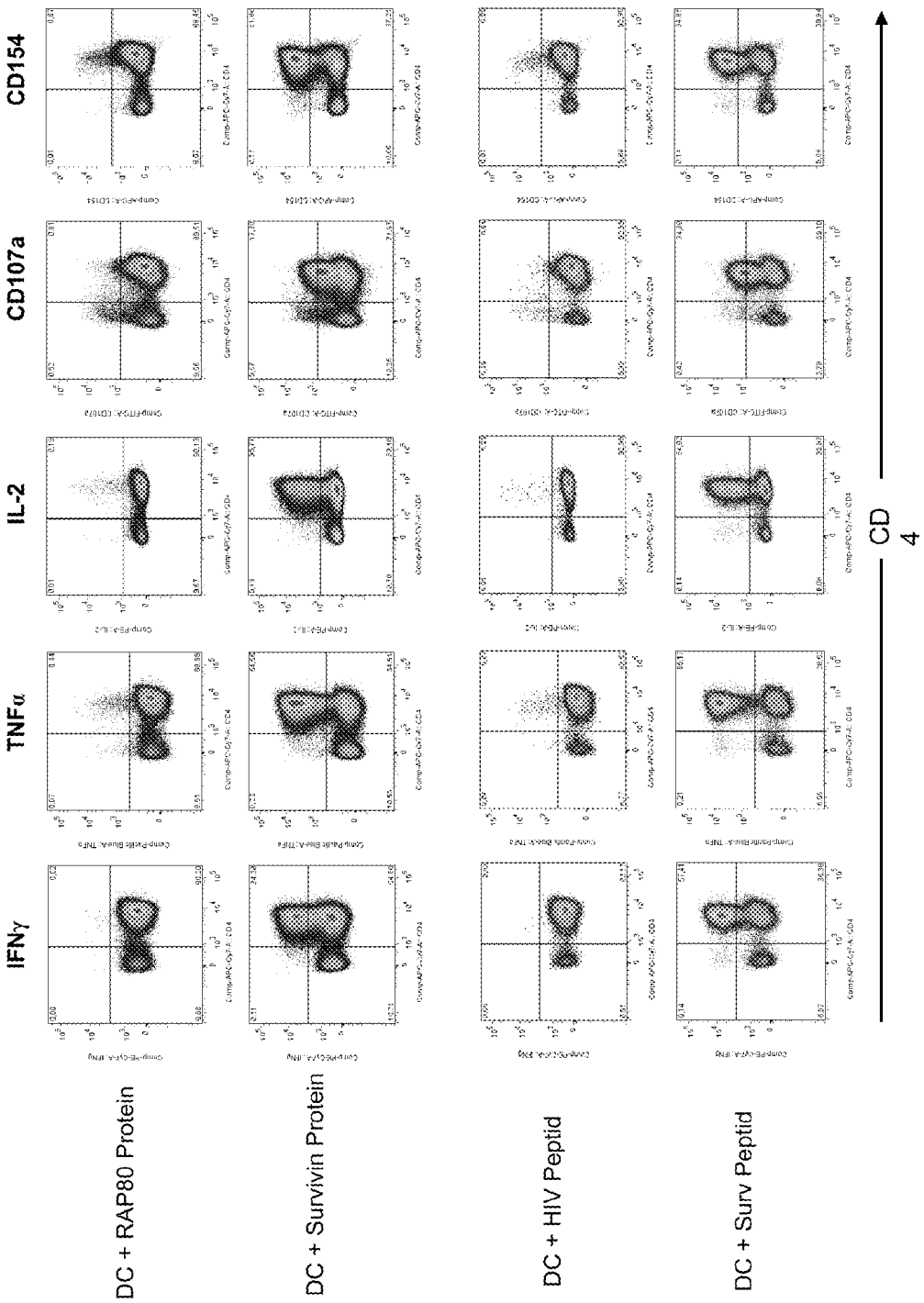
FIG. 13 shows that BIR-002 is naturally presented by dendritic cells. Immature dendritic cells incubated with recombinant survivin protein are recognized by BIR-002 specific T-cells from vaccinated patients as shown by intracellular cytokine staining. These results suggest that BIR-002 is naturally processed by proteinases within dendritic cells and that the BIR-002 epitope is not destroyed by processing. In addition, these CD4+ T-cells are multifunctional as they secrete cytokines IFN-gamma, TNF-alpha and IL-2, have surface expression of CD40 ligand (CD154) and degranulate indicated by surface expression of CD107a. The indicated T-cell response is antigen-specific, as the T-cells are not activated by dendritic cells incubated with the irrelevant protein RAP80, or HIV-001 peptide.
Figure 14:
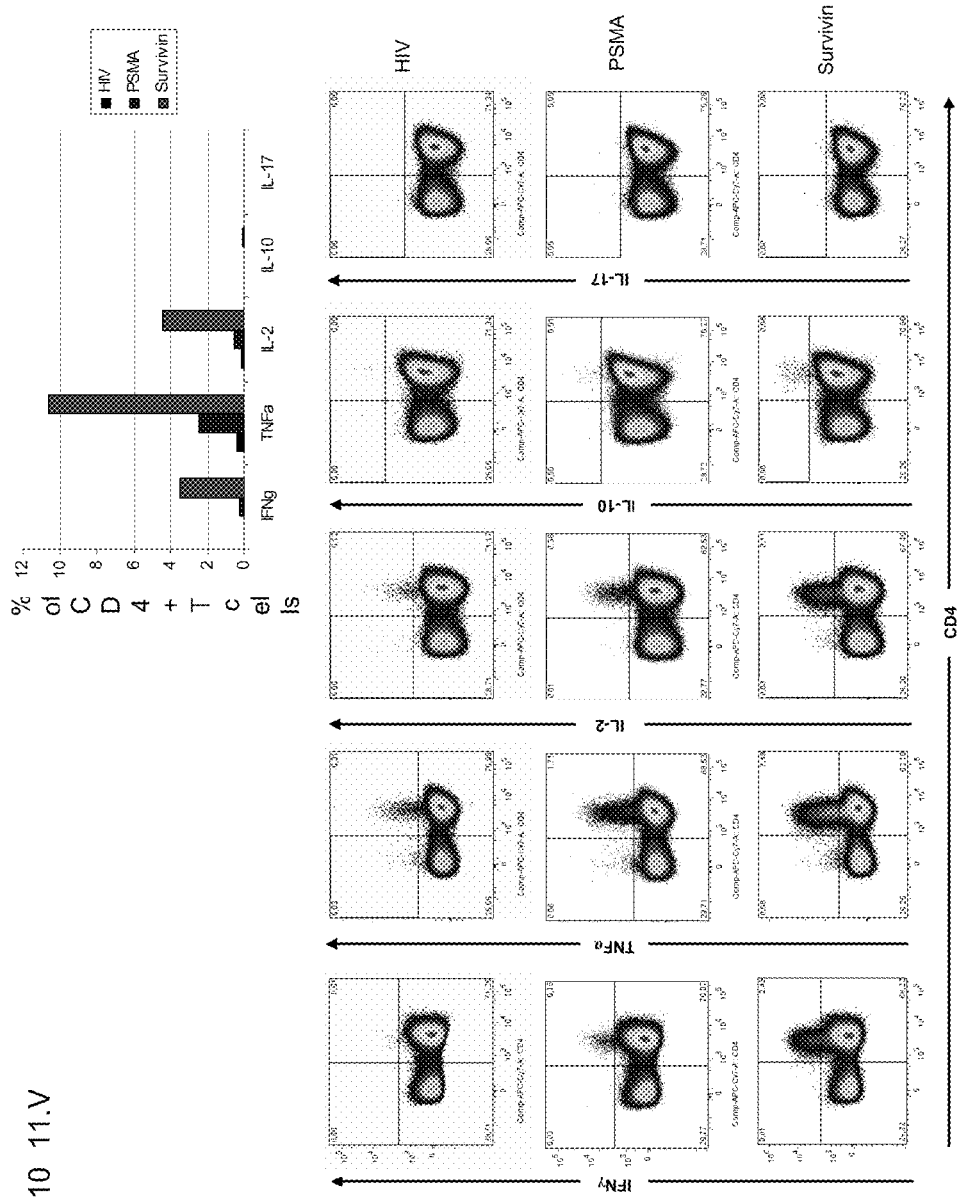
FIG. 14 shows that a high fraction of BIR-002-specific CD4+ T cells derived from BIR-002 vaccinated prostate cancer patients express beneficial cytokines IFN-gamma, TNF-alpha, IL-2 while the immunoregulatory cytokines IL-10 and IL-17 are not expressed to that extent. Shown are primary data and summarized data from intracellular cytokine staining of T-cells specific for BIR-002 or two control class II restricted peptides.

A peptide, oligopeptide, protein, or polynucleotide coding for such a molecule is "immunogenic" (and thus an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response.

A T cell "epitope" requires a short peptide that is bound to a class I or II MHC receptor, which forms a ternary complex (MHC class I alpha chain, beta-2-microglobulin, and peptide) that can be recognized by a T cell bearing a matching T-cell

| Name | cell line | Reference |
|---|---|---|
| AL | E418 EBV transformed B-cell line | Human Immunology Volume 51, Issue 1, November 1996, Pages 13-22 |
| LAM | B lymphoma cell line | Oncogenomics 19 Sept. 2002, Volume 21, Number 42, Pages 6549-6556 |
| HO301 | EBV transformed B cell line | The Journal of Immunology, 1998, 160: 3363-3373. |
| BM15 | Dr11 + APC cell line | The Journal of Immunology, 2004, 173: 1876-1886 |
| MGAR | homozygous B-LCL | Gene Therapy (2004) 11, 1408-1415 |
| LG2-EBV | autologous B cell line | Cancer Immunity, Vol. 2, p. 9 (19 Jul. 2002) |
| EMJ | B Lymphoblastoid Cell Line | ECACC NO: 8602103 IHW Number 9097: and Hum Immunol. 1980 December; 1(4): 363-8. |

DETAILED DESCRIPTION OF THE INVENTION

The term "peptide" is used herein to designate a series of amino acid residues, connected one to the other typically by peptide bonds between the alpha-amino and carbonyl groups of the adjacent amino acids. The peptides are typically 9 amino acids in length, but can be as short as 8 amino acids in length, and as long as 16 amino acids in length.

The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 14 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

receptor binding to the MHC/peptide complex with appropriate affinity. Peptides binding to MHC class I molecules are typically 8 to 14 amino acids in length, and most typically 9 amino acids in length. T cell epitopes that bind to MHC class II molecules are typically 12 to 30 amino acids in length. In the case of peptides that bind to MHC class II molecules, the same peptide and the corresponding T cell epitope may share a common core segment, but differ in the overall length due to flanking sequences of differing lengths upstream of the amino-terminus of the core sequence and downstream of its carboxy-terminus, respectively. MHC class II receptors have a more open conformation, peptides bound to MHC class II receptors are correspondingly not completely buried in the structure of the MHC class II molecule peptide-binding cleft as they are in the MHC class I molecule peptide-binding cleft. Surprisingly, this is not the case for the peptide according to SEQ ID NO: 1, as small variations in the length of the peptide lead to an extreme decrease of activity (see below).

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-A*11 are examples of different MHC class I alleles that can be expressed from these loci.

TABLE 2

Top 30 expressed alleles in different populations
% chance of allele expressed in an individual
Top 30 expressed alleles

| Allele | Caucasian | Allele | African-American | Allele | Hispanic | Allele | Asian |
|---|---|---|---|---|---|---|---|
| A*0201 | 45.6% | C*0401 | 29.0% | A*0201 | 37.1% | A*1101 | 38.4% |
| C*0701 | 27.7% | C*0701 | 25.4% | C*0401 | 25.4% | A*2402 | 33.7% |
| A*0101 | 27.4% | C*0602 | 23.0% | A*2402 | 24.9% | C*0702 | 33.3% |
| A*0301 | 23.8% | A*0201 | 22.3% | C*0702 | 24.2% | C*0102 | 27.7% |
| C*0702 | 21.5% | A*2301 | 20.7% | C*0701 | 20.8% | A*3303 | 23.3% |
| C*0401 | 21.2% | C*0202 | 19.0% | C*0304 | 14.4% | C*0801 | 21.6% |

TABLE 2-continued

Top 30 expressed alleles in different populations
% chance of allele expressed in an individual
Top 30 expressed alleles

| Allele | Caucasian | Allele | African-American | Allele | Hispanic | Allele | Asian |
|---|---|---|---|---|---|---|---|
| B*4402 | 20.2% | A*0301 | 18.7% | A*0301 | 14.3% | C*0304 | 19.9% |
| B*0702 | 18.1% | C*0702 | 18.1% | B*0702 | 13.2% | A*0201 | 18.1% |
| B*0801 | 18.1% | B*5301 | 18.1% | B*3501 | 12.8% | B*4001 | 15.2% |
| C*0501 | 17.2% | B*0702 | 15.8% | C*0602 | 12.3% | C*0401 | 14.0% |
| C*0304 | 16.8% | C*1601 | 15.7% | C*0501 | 11.9% | B*5801 | 13.3% |
| C*0602 | 15.7% | B*1503 | 13.9% | A*0101 | 11.4% | B*4601 | 12.7% |
| A*1101 | 15.3% | B*5801 | 13.5% | A*1101 | 11.0% | B*5101 | 12.4% |
| B*4001 | 13.6% | A*6802 | 12.7% | B*5101 | 10.8% | C*0302 | 12.0% |
| A*2402 | 12.1% | C*1701 | 11.7% | C*1601 | 10.6% | B*3802 | 11.4% |
| B*3501 | 10.7% | B*4501 | 10.8% | B*4403 | 9.9% | A*0207 | 11.0% |
| C*0303 | 10.6% | B*4201 | 10.5% | C*0102 | 9.7% | B*1501 | 9.4% |
| B*5101 | 10.4% | A*3001 | 10.4% | A*2902 | 9.7% | A*0206 | 9.3% |
| C*1203 | 9.9% | B*3501 | 10.1% | C*0802 | 9.3% | C*0303 | 9.2% |
| B*1501 | 9.6% | A*0101 | 10.0% | B*1801 | 9.1% | B*1502 | 9.1% |
| A*2902 | 8.9% | C*0304 | 9.3% | A*3101 | 8.9% | A*0203 | 8.8% |
| A*2601 | 8.2% | A*3002 | 9.2% | B*5201 | 8.6% | B*4403 | 8.6% |
| A*3201 | 8.2% | B*0801 | 8.5% | B*1402 | 8.6% | C*1402 | 8.4% |
| C*0802 | 7.7% | A*3402 | 8.4% | C*0202 | 7.6% | B*3501 | 7.2% |
| A*2501 | 7.5% | A*7401 | 8.4% | C*1203 | 7.6% | C*0602 | 7.0% |
| B*5701 | 7.1% | A*3303 | 8.0% | A*2601 | 7.6% | B*5401 | 6.9% |
| B*1402 | 6.7% | C*1801 | 7.3% | A*6801 | 7.1% | B*1301 | 6.6% |
| C*0202 | 6.6% | A*2902 | 7.2% | B*0801 | 7.0% | B*4002 | 6.3% |
| B*1801 | 6.4% | B*4403 | 6.9% | A*3002 | 6.8% | B*5502 | 6.3% |
| B*4403 | 6.4% | B*4901 | 6.9% | B*4402 | 6.5% | A*2601 | 6.0% |

There are 3 different loci in the human genome for MHC class II genes: HLA-DR, HLA-DQ, and HLA-DP. MHC class II receptors are heterodimers consisting of an alpha and a beta chain, both anchoring in the cell membrane via a transmembrane region. HLA-DRB1*04, and HLA-DRB 1*07 are two examples of different MHC class II beta alleles that are known to be encoded in these loci. Class II alleles are very polymorphic, e.g. several hundred different HLA-DRB1 alleles have been described. Therefore, for therapeutic and diagnostic purposes a peptide that binds with appropriate affinity to several different HLA class II receptors is highly desirable. A peptide binding to several different HLA class II molecules is called a promiscuous binder.

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence. The term "coding region" refers to that portion of a gene that either naturally or normally codes for the expression product of that gene in its natural genomic environment, i.e., the region coding in vivo for the native expression product of the gene.

The coding region can be from a normal, mutated or altered gene, or can even be from a DNA sequence, or gene, wholly synthesized in the laboratory using methods well known to those of skill in the art of DNA synthesis.

The term "nucleotide sequence" refers to a heteropolymer of deoxyribonucleotides.

The nucleotide sequence coding for a particular peptide, oligopeptide, or polypeptide may be naturally occurring or may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements preferably derived from a microbial or viral operon.

The term "expression product" means the polypeptide or protein that is the natural translation product of the gene and any nucleic acid sequence coding equivalents resulting from genetic code degeneracy and thus coding for the same amino acid(s).

The term "fragment," when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal nontranslated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase can start synthesis of a deoxyribonucleotide chain.

The term "promoter" means a region of DNA involved in binding of RNA polymerase to initiate transcription.

The term "open reading frame (ORF)" means a series of triplets coding for amino acids without any termination codons and is a sequence (potentially) translatable into protein.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, the claimed polypeptide which has a purity of preferably 99.999%, or at least 99.99% or 99.9%; and even desirably 99% by weight or greater is expressly contemplated.

The nucleic acids and polypeptide expression products disclosed according to the present invention, as well as expression vectors containing such nucleic acids and/or such polypeptides, may be in "enriched form." As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form.

The term "active fragment" means a fragment that generates an immune response (i.e., has immunogenic activity) when administered, alone or optionally with a suitable adjuvant, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. This means that any such fragment will necessarily contain as part of its amino acid sequence a segment, fragment or portion, that is substantially identical, if not exactly identical, to a sequence of SEQ ID NO: 1 to SEQ ID NO: 3, which correspond to the naturally occurring, or "parent" protein of the SEQ ID NO: 1 to SEQ ID NO: 3, namely survivin. When used in relation to polynucleotides, such terms refer to the products produced by treatment of said polynucleotides with any of the common endonucleases.

In accordance with the present invention, the term "percent identity" or "percent identical," when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

$$\text{Percent Identity} = 100[1-(C/R)]$$

wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference;

and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity, then the Compared Sequence has the specified minimum percent identity to the Reference Sequence even though alignments may exist in which the herein above calculated Percent Identity is less than the specified Percent Identity.

The original peptides disclosed herein can be modified by the substitution of one or more residues at different, possibly selective, sites within the peptide chain, if not otherwise stated. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, amino acids possessing non-standard R groups (i.e., R groups other than those found in the common 20 amino acids of natural proteins) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than four positions within the peptide would simultaneously be substituted.

The term "T-cell response" means the specific proliferation and activation of effector functions induced by a peptide in vitro or in vivo. For MHC class I restricted CTLs, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or performs induced by peptide, or degranulation. For MHC class II-restricted T helper cells, effector functions may be peptide induced secretion of cytokines, preferably, IFN-gamma, TNF-alpha, IL-4, IL-5, IL-10, or IL-2, or peptide-induced degranulation. Possible effector functions for CTLs and T helper cells are not limited to this list.

Preferably, when the CTLs specific for a peptide derived from any of SEQ ID NO: 1 to 3 are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 µM, and most preferably no more than about 10 µM. It is also preferred that the substituted peptide be recognized by CTLs from more than one individual, at least two, and more preferably three individuals.

Thus, the epitopes of the present invention may be identical to naturally occurring tumor-associated or tumor-specific epitopes or may include epitopes that differ by no more than four residues from the reference peptide, as long as they have substantially identical antigenic activity.

Stimulation of an immune response is dependent upon the presence of antigens recognized as foreign by the host immune system. The discovery of the existence of tumor associated antigens has now raised the possibility of using a host's immune system to foster an immune response that is specific for target antigens expressed on the surface of tumor cells and which through this mechanism of action is capable of inducing regression, stasis or slowed-down growth of the tumor. Various mechanisms of harnessing both the humoral and cellular arms of the immune system are currently being explored for cancer immunotherapy.

Specific elements of the cellular immune response are capable of specifically recognizing and destroying tumor cells. The isolation of cytotoxic T cells (CTL) from tumor-infiltrating cell populations or from peripheral blood suggests that such cells play an important role in natural immune defenses against cancer (Cheever et al., 1993; Zeh, III et al., 1999). Based on the analysis of 415 specimens from patients suffering from colorectal cancer, Galon et al. were able to demonstrate that type, density and location of immune cells in tumor tissue are actually a better predictor for survival of patients than the widely employed TNM-staging of tumors (Galon et al., 2006).

MHC class I present peptides that result from proteolytic cleavage of predominantly endogenous proteins, DRIPs and larger peptides. MHC class II molecules can be found predominantly on professional antigen presenting cells (APCs), and primarily present peptides of exogenous or transmembrane proteins that are taken up by APCs during the course of endocytosis, and are subsequently processed (Cresswell, 1994). Complexes of peptide and MHC class I molecules are recognized by CD8-positive cytotoxic T-lymphocytes bearing the appropriate TCR (T-cell receptor), and complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells (Wang and Livingstone, 2003; Sun and Bevan, 2003; Shedlock and Shen, 2003). Initially, the priming and expansion of CTLs in lymph nodes is supported by CD4+ T-cells (Schoenberger et al., 1998). One mechanism therefore might be the guidance of naive CD8+ cells to the place of functional CD4+ T-cell—APC interaction (Castellino et al., 2006). Finally, the generation of functional CD8+ memory cells is in most cases dependent on CD4+ T-cell assistance (Sun and Bevan, 2003; Janssen et al., 2003). For these reasons, the identification of CD4-positive T-cell epitopes derived from tumor associated antigens (TAA) is of great importance for the development of pharmaceutical products for triggering anti-tumor immune responses (Kobayashi et al., 2002; Qin et al., 2003; Gnjatic et al., 2003). At the tumor site, T helper cells, support a CTL friendly cytokine milieu (Qin and Blankenstein, 2000; Mortara et al., 2006) and attract effector cells, e.g. CTLS, NK cells, macrophages, granulocytes (Marzo et al., 2000; Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, and dendritic cells. In cancer patients, cells of the tumor have surprisingly been found to express MHC class II molecules (Dengjel et al., 2006).

It was shown in mammalian animal models, e.g., mice, that even in the absence of CTL effector cells (i.e., CD8-positive T lymphocytes), CD4-positive T cells are sufficient for inhibiting manifestation of tumors via inhibition of angiogenesis by secretion of interferon-gamma (IFNγ) (Qin and Blankenstein, 2000). Also the direct killing of tumor cells by cytotoxic CD4+ T cells via lymphotoxins and granzyme B has been proposed (Penna et al., 1992; Littaua et al., 1992).

Additionally, it was shown that CD4-positive T cells recognizing peptides from tumor-associated antigens presented by HLA class II molecules can counteract tumor progression via the induction of antibody (Ab) responses (Kennedy et al., 2003).

In contrast to tumor-associated peptides binding to HLA class I molecules, only a small number of class II ligands of tumor associated antigens (TAA) have been described to date.

Since the constitutive expression of HLA class II molecules is usually limited to cells of the immune system (Mach et al., 1996), the possibility of isolating class II peptides directly from primary tumors was not considered possible. However, Dengjel et al. were recently successful in identifying a number of MHC Class II epitopes directly from tumors (WO 2007/028574, EP 1 760 088 B1; (Dengjel et al., 2006).

The antigens that are recognized by the tumor specific cytotoxic T lymphocytes, that is, their epitopes, can be molecules derived from all protein classes, such as enzymes, receptors, transcription factors, etc. which are expressed and, as compared to unaltered cells of the same origin, up-regulated in cells of the respective tumor.

The current classification of tumor associated antigens (TAAs) comprises the following major groups (Novellino et al., 2005):

1. Cancer-testis antigens: The first TAAs ever identified that can be recognized by T cells (van der Bruggen et al., 1991) belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members or NY-ESO-1.

2. Differentiation antigens: These TAAs are shared between tumors and the normal tissue from which the tumor arose; most are found in melanomas and normal melanocytes. Many of these melanocyte lineage-related proteins are involved in the biosynthesis of melanin and are therefore not tumor specific, but nevertheless are widely used for cancer immunotherapy. Examples include, but are not limited to, tyrosinase and Melan-A/MART-1 for melanoma or PSA for prostate cancer.

3. Overexpressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their overexpression in tumor cells can trigger an anticancer response by breaking previously established tolerance. Prominent examples for this class of TAAs are Her-2/neu, Survivin, Telomerase or WT1.

4. Tumor specific antigens: These unique TAAs arise from mutations of normal genes (such as β-catenin, CDK4, etc.). Some of these molecular changes are associated with neoplastic transformation and/or progression. Tumor specific antigens are generally able to induce strong immune responses without bearing the risk for autoimmune reactions against normal tissues. On the other hand, these TAAs are in most cases only relevant to the exact tumor on which they were identified and are usually not shared between many individual tumors.

5. TAAs arising from abnormal post-translational modifications: Such TAAs may arise from proteins that are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation, which may or may not be tumor specific (Hanada et al., 2004; Vigneron et al., 2004).

6. Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

For proteins to be recognized by cytotoxic T-lymphocytes as tumor-specific or -associated antigens, and to be used in a therapy, particular prerequisites must be fulfilled. The antigen should be expressed mainly by tumor cells and not or in comparably small amounts by normal healthy tissues. It is furthermore desirable, that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to a function e.g. in cell cycle control or suppression of apoptosis. Additionally, also downstream targets of the proteins directly causative for a transformation may be upregulated and thus may be indirectly tumor-associated. Such indirectly tumor-associated antigens may also be targets of a vaccination approach (Singh-Jasuja et al., 2004). In both cases it is essential that epitopes are present in the amino acid sequence of the antigen, since such a peptide ("immunogenic peptide") that is derived from a tumor associated antigen should lead to an in vitro or in vivo T-cell-response.

Basically, any peptide able to bind a MHC molecule may function as a T-cell epitope. A prerequisite for the induction of an in vitro or in vivo T-cell-response is the presence of a T cell with a corresponding TCR and the absence of immunological tolerance for this particular epitope.

Therefore, TAAs are a starting point for the development of a tumor vaccine. The methods for identifying and characterizing the TAAs are based on the use of CTL that can be isolated from patients or healthy subjects, or they are based on the generation of differential transcription profiles or differential peptide expression patterns between tumors and normal tissues (Lemmel et al., 2004; Weinschenk et al., 2002).

However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and immunological tolerance for this particular epitope needs to be absent or minimal. It is therefore important to select only those peptides from over-expressed or selectively expressed proteins that are presented in connection with MHC molecules against which a functional T cell can be found. Such a functional T cell is defined as a T cell that upon stimulation with a specific antigen can be clonally expanded and is able to execute effector functions ("effector T cell").

T-helper cells play an important role in orchestrating the effector function of CTLs in anti-tumor immunity. T-helper cell epitopes that trigger a T-helper cell response of the $T_{H1}$ type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

Since both types of response, CD8 and CD4 dependent, contribute jointly and synergistically to the anti-tumor effect, the identification and characterization of tumor-associated antigens recognized by either CD8+ CTLs (ligand: MHC class I molecule+peptide epitope) or by CD4-positive T-helper cells (ligand: MHC class II molecule+peptide epitope) is important in the development of tumor vaccines.

Considering the severe side-effects and expense associated with treating cancer better prognosis and diagnostic methods are desperately needed. Therefore, there is a need to identify other factors representing biomarkers for cancer in general and glioblastoma in particular. Furthermore, there is a need to identify factors that can be used in the treatment of cancer in general and glioblastoma in particular.

Furthermore, there is no established therapeutic design for prostate cancer patients with biochemical relapse after radical prostatectomy, usually caused by residual tumor left in situ in the presence of locally advanced tumor growth. New therapeutic approaches that confer lower morbidity with comparable therapeutic efficacy relative to the currently available therapeutic approaches would be desirable.

The present invention provides peptides that are useful in treating glioblastoma, prostate cancer and other tumors that overexpress survivin. These peptides were partly directly shown by mass spectrometry to be naturally presented by HLA molecules on primary human glioblastoma samples (see Example 1 and FIG. 1), or in the case of SEQ ID NO: 1 and 2 predicted according to the SYFPEITHI prediction algorithm (Rammensee et al., 1995) to be promiscuous binders to the HLA-DR alleles HLA-DRB1*01, DRB1*03, DRB1*04, DRB1*11, and DRB1*15 (see attachment). Based on this data and the frequencies of these frequent DRB1 alleles (Mori et al., 1995; Chanock et al., 2004), it can be assumed that 92% of A*02-positive Caucasians express at least one DRB1 allele that binds these peptides (SEQ ID NO: 1 to SEQ ID NO: 3). SEQ ID NO: 2 contains the same core sequence as SEQ ID NO: 1, elongated by two N-terminal amino acids from the natural survivin sequence to contain a described class I T-cell epitope from survivin (Schmitz et al., 2000). SEQ ID NO: 3 contains the same sequence as SEQ ID NO: 1, wherein the last C-terminal amino acid is modified from an asparagine (N) to aspartic acid (D).

The source gene from which SEQ ID NO: 1 to SEQ ID NO: 3 are derived—survivin—was shown to be highly overexpressed in glioblastoma, prostate tumor, breast cancer, esophageal cancer, colorectal cancer, clear cell renal cell carcinoma, lung cancer, CNS, ovarian, melanoma (Tamm et al. 1998) pancreatic cancer, squamous cell carcinoma, leukemia and medulloblastoma compared with normal tissues (see Example 2 and FIG. 2) demonstrating a high degree of tumor association of the peptide, i.e. these peptides are strongly presented on tumor tissue but not on normal tissues.

HLA-bound peptides can be recognized by the immune system, specifically T lymphocytes/T cells. T cells can destroy the cells presenting the recognized HLA/peptide complex, e.g. glioblastoma tumor cells presenting the survivin-derived (SEQ ID NO: 1 to SEQ ID NO: 3). T helper cells activated by the survivin-derived peptides can inhibit tumor vascularization, can attract effector cells of the immune system and facilitate CTL priming, proliferation, and a sustained CD8+ T-cell response.

All peptides of the present invention have been shown to be capable of stimulating T cell responses (see Example 4 and FIG. 4). Thus, the peptides are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The pharmaceutical compositions comprise the peptides either in the free form or in the form of a pharmaceutically acceptable salt.

As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —$NH_2$ group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment the pharmaceutical compositions comprise the peptides as salts of acetic acid (acetates) or hydrochloric acid (chlorides).

In addition to being useful for treating cancer, the peptides of the present invention are also useful as diagnostics. Since the peptides were generated from glioblastoma and since it was determined that these peptides are not present in normal tissues, these peptides can be used to diagnose the presence of a cancer.

The presence of claimed peptides on tissue biopsies can assist a pathologist in diagnosis of cancer. Detection of certain peptides by means of antibodies, mass spectrometry or other methods known in the art can tell the pathologist that the tissue is malignant or inflamed or generally diseased. Presence of groups of peptides can enable classification or subclassification of diseased tissues.

The detection of peptides on diseased tissue specimen can enable the decision about the benefit of therapies involving the immune system, especially if T lymphocytes are known or expected to be involved in the mechanism of action. Loss of MHC expression is a well described mechanism by which infected of malignant cells escape immunosurveillance. Thus, presence of peptides shows that this mechanism is not exploited by the analyzed cells.

The peptides might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The peptides can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

In addition, they can be used to verify a pathologist's diagnosis of a cancer based on a biopsied sample.

Table 3 shows the peptides according to the present invention, their respective SEQ ID NO:, the HLA alleles to which the respective peptides bind, and the source proteins from which these peptides may arise. Of special interest is the fact that the peptide according to SEQ ID NO: 2 binds to HLA-DR as well as HLA-A*02, thus eliciting two different responses.

TABLE 3

Peptides of the present invention

| SEQ ID NO: | Peptide Code | Sequence | HLA Alleles | Source Protein(s) |
|---|---|---|---|---|
| 1 | BIR-002 | TLGEFLKLDRERAKN | HLA-DR | Survivin |
| 2 | BIR-004 | ELTLGEFLKLDRERAKN | HLA-DR and HLA-A*02 | Survivin |
| 3 | BIR-002a | TLGEFLKLDRERAKD | HLA-DR | Survivin |

Expression of BIRC5 (survivin), a member of the inhibitor of apoptosis protein (IAP) family, is elevated in fetal tissues and in various human cancers, with greatly reduced expression in adult normal differentiated tissues, particularly if their proliferation index is low. Survivin seems to be capable of regulating both cellular proliferation and apoptotic cell death. Although survivin is usually located in the cell cytoplasmic region and associated with poor prognosis in cancer, nuclear localization, indicative of favorable prognosis, has also been reported (O'Driscoll et al., 2003). Regulation of and through survivin has been described by several mechanisms. Survivin seems to be associated with the molecular chaperone Hsp60. In vivo, Hsp60 is abundantly expressed in primary human tumors as compared with matched normal tissues. Acute ablation of Hsp60 by small interfering RNA destabilizes the mitochondrial pool of survivin, induces mitochondrial dysfunction, and activates caspase-dependent apoptosis (Ghosh et al., 2008). Furthermore, Ras inhibition results in release of the survivin "brake" on apoptosis and in activation of the mitochondrial apoptotic pathway. Especially in glioblastoma, resistance to apoptosis can be abolished by a Ras inhibitor that targets survivin (Blum et al., 2006). There also seems to be a correlation between NF-kappaB hyperactivity in gliomas and hyperexpression of survivin, one of NF-kappaB target genes. Thus, NF-kappaB-activated anti-apoptotic genes are hyperexpressed in tumor samples. Especially in glioblastoma, very high levels of survivin expression are detectable (Angileri et al., 2008). It is suggested that survivin overexpression in brain gliomas might play an important role in malignant proliferation, anti-apoptosis and angiogenesis (Zhen et al., 2005; Liu et al., 2006). Several analyses were performed to study survivin expression and its impact on survival in glioblastoma. To summarize, survivin expression, especially the simultaneous expression in nucleus and cytoplasm in astrocytic tumors was significantly associated with malignancy grade (with highest survivin expression in glioblastoma) and shorter overall survival times compared with patients who had survivin-negative tumors (Kajiwara et al., 2003; Saito et al., 2007; Uematsu et al., 2005; Mellai et al., 2008; Grunda et al., 2006; Xie et al., 2006; Sasaki et al., 2002; Chakravarti et al., 2002).

Survivin-overexpression has also been described for other tumor entities. In breast cancer, survivin expression is associated with higher grade and shorter disease-free survival (Yamashita et al., 2007; Al-Joudi et al., 2007; Span et al., 2004). In esophageal cancer cell lines, the promoter activity of survivin was shown to be 28.5 fold higher than in normal tissues (Sato et al., 2006). In colorectal cancer, survivin expression is also associated with pathological grade and lymph node metastasis (Tan et al., 2005). The aggressiveness of clear cell renal cell carcinoma was shown to be associated with survivin expression. Furthermore, expression of survivin is inversely associated with cancer-specific survival (Kosari et al., 2005). Survivin expression can be detected in a panel of keratinocytic neoplasms and hyperproliferative skin lesions but not in normal skin (Bowen et al., 2004). In pancreatic cancer cell lines, survivin was amplified in 58% of the tested cell lines (Mahlamaki et al., 2002). In squamous cell carcinoma, survivin expression can help to identify cases with more aggressive and invasive clinical phenotype (Lo et al., 2001).

As survivin is such a promising target for cancer therapy, studies using survivin-derived peptides showed that survivin is immunogenic in tumor patients by eliciting CD8+ T cell-mediated responses. In addition, survivin specifically stimulated CD4+ T-cell reactivity in peripheral blood lymphocytes from the same patients (Casati et al., 2003; Piesche et al., 2007).

Survivin (SVN, BIRC) is overexpressed in a multitude of cancer entities. Thus, in general, overexpression of survivin is thought to be associated with shorter overall-survival and higher malignancy grades.

Piesche (2006) disclosed as part of his study (see also (Piesche et al., 2007)), MHC class II and HLA class II-restricted candidate epitopes in survivin (SVN) and in proteinase-3 (PR3), which were determined using the computer program TEPITOPE (Bian and Hammer, 2004). The TEPITOPE analysis yielded 6 candidate epitopes for SVN and 11 candidate epitopes for PR3 with high binding probability for various HLA-DR alleles. These 17 peptides were used in T cell immunologic experiments after synthesis and chromatographic purification. The variable lengths of the peptides resulted from overlapping epitopes that were considered together in one peptide (Table 4).

TABLE 4

Names, AA position, and AA sequences of the synthetic SVN peptides disclosed by Piesche 2006.

| Peptide | Position | Amino acid sequence | T cell frequency |
|---|---|---|---|
| $S_{10}$ | 10-24 (SEQ ID NO: 28) | WQPFLKDHRISTFKN | $8.64 * 10^{-7}$ |
| $S_{22}$ | 22-36 (SEQ ID NO: 29) | FKNWPFLEGAAATPE | $7.2 * 10^{-7}$ |
| $S_{40}$ | 40-54 (SEQ ID NO: 30) | EAGFIHAPTENEPDL | $8.64 * 10^{-7}$ |
| $S_{58}$ | 58-72 (SEQ ID NO: 31) | FFCFKELEGWEPDDD | $4.32 * 10^{-7}$ |
| $S_{88}$ | 88-103 (SEQ ID NO: 32) | LGEFLKLDRERAKNKI | $1.73 * 10^{-7}$ |
| $S_{110}$ | 110-124 (SEQ ID NO: 33) | KNKIAKETNNKKKEF | $8.64 * 10^{-7}$ |

(Note: $S_{88}$ actually is $S_{98}$, thus, Piesche et al. may have made an error in determining the position of this epitope).

Titration experiments with the corresponding peptides were performed by Piesche to estimate the peptide HLA affinity or the peptide HLA/TCR avidity. The lower the peptide concentration, the higher the binding affinity of the peptide epitopes to the MHC molecules, an important prerequisite for the natural presentation of "genuine" T cell epitopes from an intracellular processing of the protein antigen. The measured half-maximal proliferative activity of the peptide-specific T cell clones were <50 nM for $S_{10}$, 400-700 nM for $S_{40}$, 2000-3000 nM for $S_{88}$ and 100-300 nM for $P_{58}$. Piesche further disclosed that only the SVN peptide $S_{10}$ elicited a specific T cell proliferation during exposure with recombinant SVN protein. This was shown in three $S_{10}$-specific T cell clones from different donors. Piesche et al. investigated the processing and presentation of SVN peptide epitopes from natural antigen by co-culturing of peptide-specific T cell clones with SVN protein-pulsed DCs. Only the SVN peptide $S_{10}$ was able to cause specific T cell proliferation during exposure with recombinant SVN protein. This was shown in three $S_{10}$-specific T cell clones from different donors. No specific proliferation in response to the natural antigen was detected for the $PR_3$-specific T cell clones.

Further, tumor antigens from apoptotic or necrotic tumor cells were internalized by APCs in vivo, processed independently of MHC II and presented to CD4+ T cells. For T cell recognition of the genuine $S_{10}$ epitope, DCs with tumor cell lysates from various SVN-positive tumor cell lines were pulsed. For the $S_{10}$ epitope, direct in vitro recognition of lysate-pulsed DCs from the tumor cell lines Karpas-422, Jurkat, and HL-60 was detected. This was shown in at least three $S_{10}$-specific T cell clones from different donors.

To show that the epitope $S_{10}$ can induce an immune response in cancer patients the presence of the corresponding CD4+ T lymphocytes in the blood of tumor patients had to be confirmed. PBMCs from various patients were isolated and stimulated with the $S_{10}$ peptide. For this purpose PBMC samples were drawn from patients before beginning of treatment and after the start of cytotoxicstatic therapy, Monocytes and B cells contained in the PBMC fraction were used as antigen-/peptide-presenting cells. After one week of culturing, the cells were analyzed with respect to their peptide-specific proliferation using a [$^3$H]-thymidine incorporation assay. Of 13 tested patients, only three had a detectable proliferative response in vitro.

The potential use of peptide epitopes in immunotherapy essentially depends on whether the peptide-specific CD4+ T lymphocytes respond to the corresponding antigen. Recognition of the naturally processed protein antigen in the form of "genuine" or "true" epitopes is influenced by various factors in principle.

Piesche showed that protein recognition was only detectable for the SVN epitope $S_{10}$. For the other identified peptides (SVN: $S_{40}$, $S_{88}$; $PR_3$: $P_{58}$, $P_{216}$, $P_{235}$, and $P_{239}$) no protein recognition was detectable. Piesche et al. stated that it is important, during endosomal proteolysis, for the present sequence motifs not to be degraded, as in the case of "cryptic" epitopes. In contrast to MHC class I-restricted epitopes, MHC class II molecules can take up peptides of variable length (12-28); therefore, proteolytic cleavage of the peptide epitopes into defined lengths is not required.

Surprisingly and in contrast to Piesche's epitopes, the inventors show in the present invention that another epitope, SEQ ID NO: 1, derived from survivin which is shorter than $S_{88}$, but also overlapping, elicited a strong immuno-response in 16 out of 19 patients in vivo. (See Example 4). Due to the high polymorphism of the HLA-DR locus, this is also a proof of the highly promiscuous binding of peptide SEQ ID NO: 1 as predicted, as an immune response can only be evoked by a peptide bound to an HLA molecule.

The importance of the cancer entities for which an overexpression of survivin was described in the literature is illustrated by Table 1. Cancer indications for which overexpression of survivin are a commonly described feature were accountable for over 415,000 deaths in 2007 (see Table 1).

Piesche et al. (2006) showed in vitro the presence of appropriate precursors for peptide $S_{88}$ in three out of four donors with overlapping HLA-DR alleles. Here the body of evidence is too small to deduce a promiscuous binding of $S_{88}$ to HLA-DR, as the obtained results may be explained by binding to two different HLA-DR alleles (e.g. DR3 and DR11, or DR1 and DR3, or DR11 and DR4). In addition, the stimulation indices obtained by a quite unspecific proliferation assay ([$^3$H]-thymidine incorporation) from whole PBMC cultures are quite low and a positive control is missing (e.g. a mix of well-characterized, strongly immunogenic viral peptides) and appropriate negative controls (stimulation during proliferation assay with an irrelevant control peptide) are missing. The data on precursor frequencies were not confirmed by a second type of assay.

WO 2007/036638 ("Wang et al"), amongst others, discloses survivin peptides of the amino acid sequences:

```
96-110    (LTLGEFLKLDRERAK; SEQ ID NO: 25);

99-113    (GEFLKLDRERAKNKI; SEQ ID NO: 26); and 102-116   (LKLDRERAKNKIAKE; SEQ ID NO: 27).
```

As a region binding HLA-molecules of MHC class II with "good" affinity ($IC_{50}$<1000 nM), the region 84 to 113 is described. Nevertheless, the peptides as examined in Wang et al. show a very broad spectrum of binding towards the different HLA-molecules, and the binding even differs drastically within the region as described, when the peptides are shifted in their sequence by one or two amino acids.

The peptide of the present invention of SEQ ID NO: 3 (TLGEFLKLDRERAKD; "BIR-002a" peptide) comprises a sequence of the BIR-002 peptide of the present invention of SEQ ID NO: 1, except that C-terminally, the peptide ends with the amino acid aspartic acid (D) instead of asparagine (N). The peptide overlaps with the peptide $S_{88}$ of Piesche, which contains the last three amino acids NKI. As mentioned above, the $S_{88}$ peptide was inactive in a specific T cell proliferation assay during exposure with recombinant SVN protein. In contrast, the BIR-002a peptide showed a strong MHC II-related immuno-response. Without wanting to be bound by theory, it is assumed that an enzymatic conversion of the asparagine into aspartic acid through an asparaginase takes place in vivo, and thus the C-terminal amino acid is modified (and the peptide becomes activated and/or further activated). Since the C-terminal asparagine of the Piesche-peptide $S_{88}$ is blocked by two amino acids, the peptide is inactive (further showing the importance of a single amino acid change in the activity of this peptide).

Furthermore, it was noted that the immuno-responses and activities of other peptides comprising a C-terminal asparagine (such as, for example, SEQ ID NO: 1) may also depend on a C-terminal conversion into an acid amino acid, in particular aspartic acid. Thus, in one aspect of the present invention, the peptide according to SEQ ID NO: 1 may be seen as a "prodrug" for SEQ ID NO: 3, which provides the active peptide according to SEQ ID NO: 3 after enzymatic conversion. It should be understood that the present invention also encompasses chemical conversion of the amino acid, particularly asparagine, and the spontaneous deamidation by the loss of one molecule of water.

Furthermore, the examples showing an activity for the peptide according to SEQ ID NO: 1 also support an activity for the modified peptide according to SEQ ID NO: 3.

It could furthermore be found in the context of the present invention that the solubilities of peptides in the area of the BIR-002 peptide (region 84 to 113) differ drastically for very similar peptides. It has to be noted that in Wang et al., peptides in the region close to the BIR-002 peptide were actually insoluble, and binding studies could not be performed.

The solubilities were determined as follows:

BIR-002 (SEQ ID No: 1): <32.9 mg/mL (acetate)

BIR-002a (SEQ ID No: 3) (D instead of N at the C-terminal end): <23.5 mg/mL

BIR-014 (comparative peptide of Wang, SEQ ID NO: 25): <99.5 mg/mL

Yet another aspect of the present invention relates to an antibody that specifically binds to a human major histocompatibility complex (MHC) class I or II complexed with a HLA-restricted antigen (in the following also designate as "complex-specific antibody"). Yet another aspect of the present invention relates to a method of producing the antibody specifically binding to a human major histocompatibility complex (MHC) class I or II complexed with a HLA-restricted antigen, the method comprising: immunizing a genetically engineered non-human mammal comprising cells expressing a human major histocompatibility complex (MHC) class I or II with a soluble form of a MHC class I or II molecule being complexed with the HLA-restricted antigen; isolating mRNA molecules from antibody producing cells of the non-human mammal; producing a phage display library displaying protein molecules encoded by the mRNA molecules; and isolating at least one phage from said phage display library, the at least one phage displaying the antibody specifically bindable to the human major histocompatibility complex (MHC) class I or II complexed with the HLA-restricted antigen. Respective methods for producing such antibodies and single chain class I major histocompatibility complexes, as well as other tools for the production of these antibodies are disclosed in WO 03/068201, WO 2004/084798, WO 01/72768, WO 03/070752, and Cohen C J, Denkberg G, Lev A, Epel M, Reiter Y. Recombinant antibodies with MHC-restricted, peptide-specific, T-cell receptor-like specificity: new tools to study antigen presentation and TCR-peptide-MHC interactions. J Mol Recognit. 2003 September-October; 16(5):324-32.; Denkberg G, Lev A, Eisenbach L, Benhar I, Reiter Y. Selective targeting of melanoma and APCs using a recombinant antibody with TCR-like specificity directed toward a melanoma differentiation antigen. J Immunol. 2003 Sep. 1; 171(5):2197-207; and Cohen C J, Sarig O, Yamano Y, Tomaru U, Jacobson S, Reiter Y. Direct phenotypic analysis of human MHC class I antigen presentation: visualization, quantitation, and in situ detection of human viral epitopes using peptide-specific, MHC-restricted human recombinant antibodies. J Immunol. 2003 Apr. 15; 170(8):4349-61, which for the purposes of the present invention are all explicitly incorporated by reference in their entireties.

Preferably, the antibody binds with a binding affinity of below 20 nanomolar, preferably of below 10 nanomolar, to the complex, which is regarded as "specific" in the context of the present invention.

The term "antibody" is used herein in a broad sense and includes both polyclonal and monoclonal antibodies. In addition to intact immunoglobulin molecules, also included in the term "antibodies" are fragments such as, but not limited to, Fabs and scFvs or polymers of those immunoglobulin molecules and humanized versions of immunoglobulin molecules, so long as they exhibit any of the desired properties (e.g., being a complex-specific antibody as above, delivery of a toxin to a cancer cell expressing an cancer marker gene at an increased level, and/or inhibiting the activity of an cancer marker polypeptide, such as survivin) described herein.

Whenever possible, the antibodies of the invention may be purchased from commercial sources. The antibodies of the invention may also be generated using well-known methods. The skilled artisan will understand that either full length cancer marker polypeptides or fragments thereof may be used to generate the antibodies of the invention. A polypeptide to be used for generating an antibody of the invention may be partially or fully purified from a natural source, or may be produced using recombinant DNA techniques. For example, a cDNA encoding a survivin polypeptide, or a fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the cancer marker polypeptide used to generate the antibody. Complex-specific antibodies will usually be generated as above.

One of skill in the art will know that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Harlow and Lane, Antibodies: A Laboratory Manual, Cold Spring Harbor Laboratory Press, Cold Spring Harbor, N.Y., 1988). For example, the antibodies may be tested in ELISA assays, Western blots, immunohistochemical staining of formalin-fixed cancer samples or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567).

Monoclonal antibodies of the invention may be prepared using hybridoma methods. In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries as, for example, described above for the complex-specific antibodies.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Additional carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. Antibodies in Human Diagnosis and Therapy, Haber et al, eds. Raven Press, New York (1977) pp. 365-389. A typical daily dosage of the antibody used alone might range from about 1 (μg/kg to up to 100 mg/kg of body weight or more per day) depending on the factors mentioned above. Following administration of an antibody for treating cancer, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of cancers.

The antibodies may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more cancer targets and the affinity value (Kd) is less than $1 \times 10$ µM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with the probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the desired protein expressed in situ.

The present invention thus provides a peptide comprising a sequence that is selected from the group of SEQ ID NO: 1 to SEQ ID NO: 3 or a variant thereof which is 85% homologous to SEQ ID NO: 1 to SEQ ID NO: 3 or a variant thereof that will induce T cells cross-reacting with the peptide. In a preferred embodiment, the variant is 95% homologous or 95% identical to SEQ ID NO: 1 or SEQ ID NO: 3, as long as the variant will induce T cells cross-reacting with the peptide.

In a preferred embodiment for the treatment of renal cell carcinoma the peptide of the SEQ ID NO: 1 and/or SEQ ID NO: 2 and/or SEQ ID NO: 3 is used in combination with at least two of the peptides with SEQ ID NO: 4 to SEQ ID NO: 13 and SEQ ID NO: 24. The peptide of the SEQ ID NO: 1 to SEQ ID NO: 3 may thereby be administered separately or together with the other peptides in one formulation.

| Internal Sequence ID | Antigen | Sequence | SEQ ID NO: |
|---|---|---|---|
| IMA-MMP-001 | Matrix metalloproteinase 7 | SQDDIKGIQKLYGKRS | 4 |
| IMA-ADF-002 | Adipophilin | VMAGDIYSV | 5 |
| IMA-ADF-001 | Adipophilin | SVASTITGV | 6 |
| IMA-APO-001 | Apolipoprotein L1 | ALADGVQKV | 7 |
| IMA-CCN-001 | Cyclin D1 | LLGATCMFV | 8 |
| IMA-GUC-001 | GUCY1A3 | SVFAGVVGV | 9 |
| IMA-K67-001 | KIAA0367 | ALFDGDPHL | 10 |
| IMA-MET-001 | c-met proto-oncogene | YVDPVITSI | 11 |
| IMA-MUC-001 | MUC1 | STAPPVHNV | 12 |
| IMA-RGS-001 | RGS-5 | LAALPHSCL | 13 |
| IMA-HBV-001 | HBV | FLPSDFFPSV | 14 |
| IMA-NCAN-001 | Neurocan | VLCGPPPAV | 24 |

A detailed description of the peptides and the antigens provided above is disclosed in WO 2007/028573.

In a preferred embodiment for the treatment of colon cancer, the peptide of the SEQ ID NO: 1 to SEQ ID NO: 3 is used in combination with at least two of the peptides with SEQ ID NO: 15 to 24, 4, 8, 11 or 12. The peptide of the SEQ ID NO: 1 to SEQ ID NO: 3 may thereby be administered separately or together with the other peptides in one formulation.

| SEQ ID NO: | Peptide ID | Sequence | Gene Symbol | Function | binds to MHC |
|---|---|---|---|---|---|
| 15 | C20-001 | ALSNLEVTL | C20orf42 | implicated in linking actin cytoskeleton to ECM | HLA-A*02 |
| 16 | NOX-001 | ILAPVILYI | NOX1 | NADPH oxidase | HLA-A*02 |
| 17 | ODC-001 | ILDQKINEV | ODC1 | Ornithine decarboxylase | HLA-A*02 |
| 18 | PCN-001 | KLMDLDVEQL | PCNA | DNA polymerase delta auxiliary protein | HLA-A*02 |
| 19 | TGFBI-001 | ALFVRLLALA | TGFBI | transforming growth factor, beta-induced | HLA-A*02 |
| 20 | TOP-001 | KIFDEILVNA | TOP2A/TOP2B | Topoisomerase | HLA-A*02 |
| 21 | TGFBI-004 | TPPIDAHTRNLLRNH | TGFBI | transforming growth factor, beta-induced | HLA-DR |
| 22 | CEA-006 | SPQYSWRINGIPQQHT | CEACAM5 | Carcinoembryonic antigen | HLA-DR |
| 8 | CCN-001 | LLGATCMFV | CCND1 | Cyclin D1 | HLA-A*02 |

-continued

| SEQ ID NO: | Peptide ID | Sequence | Gene Symbol | Function | binds to MHC |
|---|---|---|---|---|---|
| 12 | MUC-001 | STAPPVHNV | MUC1 | Mucin 1 | HLA-A*02 |
| 4 | MMP-001 | SQDDIKGIQKLYGKRS | MMP7 | Metalloproteinase 7 | HLA-DR |
| 23 | CEA-004 | YLSGANLNL | CEACAM5 | variant of CEA peptide | HLA-A*02 |
| 11 | MET-001 | YVDPVITSI | MET | met proto-oncogene | HLA-A*02 |

A detailed description of the peptides and the antigens provided above is disclosed in EP07014796.2 and U.S. 60/953,161.

The peptides of the invention have the ability to bind to a molecule of the human major histocompatibility complex (MHC) class-I or -II.

In the present invention, the term "homologous" refers to the degree of identity between sequences of two amino acid sequences, i.e. peptide or polypeptide sequences. The aforementioned "homology" is determined by comparing two sequences aligned under optimal conditions over the sequences to be compared. The sequences to be compared herein may have an addition or deletion (for example, gap and the like) in the optimum alignment of the two sequences. Such a sequence homology can be calculated by creating an alignment using, for example, the ClustalW algorithm (Nucleic Acid Res., 22(22): 4673 4680 (1994). Commonly available sequence analysis software, more specifically, Vector NTI, GENETYX or analysis tools provided by public databases.

A person skilled in the art will be able to assess, whether T cells induced by a variant of a specific peptide will be able to cross-react with the peptide itself (Fong et al., 2001); (Zaremba et al., 1997; Colombetti et al., 2006; Appay et al., 2006).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in SEQ ID NO: 1 to 24. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated CTL. These CTL can subsequently cross-react with cells and kill cells that express a polypeptide that contains the natural amino acid sequence of the cognate peptide as defined in the aspects of the invention. As can be derived from the scientific literature (Rammensee et al., 1997) and databases (Rammensee et al., 1999), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus one skilled in the art would be able to modify the amino acid sequences set forth in SEQ ID NO: 1 to 24, by maintaining the known anchor residues, and would be able to determine whether such variants maintain the ability to bind MHC class I or II molecules. The variants of the present invention retain the ability to bind to the TCR of activated CTL, which can subsequently cross-react with—and kill cells that express a polypeptide containing the natural amino acid sequence of the cognate peptide as defined in the aspects of the invention.

Those amino acid residues that do not substantially contribute to interactions with the T-cell receptor can be modified by replacement with another amino acid whose incorporation does not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 5

Variants and motif of the peptide according to SEQ ID NO: 24

| SEQ ID NO NCAN | | Position | | | | | | | | |
|---|---|---|---|---|---|---|---|---|---|---|
| | | 1 | 2 | 3 | 4 | 5 | 6 | 7 | 8 | 9 |
| 24 | Peptide Code | V | L | C | G | P | P | P | A | V |
| 73 | Variants | | M | | | | | | | L |
| 74 | | | I | | | | | | | L |
| 75 | | | | | E | | | K | | |
| 76 | | I | | A | G | I | I | A | E | |
| 77 | | L | | Y | P | K | L | Y | | |
| 78 | | F | | F | T | Y | T | H | | |
| 79 | | K | | P | | N | | | | |
| 80 | | | | M | | M | | F | | |
| 81 | | Y | | S | | V | | | | |
| 82 | | V | | R | | | | | | |
| 83 | | | M | | | | | | | L |

It is furthermore known for MHC-class II-presented peptides that these peptides are composed of a "core sequence" having an amino acid sequence fitting to a certain HLA-allele-specific motif and, optionally, N- and/or C-terminal extensions that do not interfere with the function of the core sequence (i.e. are deemed as irrelevant for the interaction of the peptide and all or a subset of T cell clones recognizing the natural counterpart). The N- and/or C-terminal extensions can, for example, be between 1 to 10 amino acids in length, respectively. These peptides can be used either directly to load MHC class II molecules or the sequence can be cloned into the vectors according to the description herein below. As these peptides constitute the final product of the processing of larger peptides within the cell, longer peptides can be used as well. The peptides of the invention may be of any size, but typically they may be less than 100,000 in molecular weight, preferably less than 50,000, more preferably less than 10,000 and typically about 5,000. In terms of the number of amino acid residues, the peptides of the invention may have fewer than 1,000 residues, preferably fewer than 500 residues, more preferably fewer than 100, more preferably fewer than 100 and most preferably between 30 and 8 residues. Accordingly, the present invention also provides peptides and variants thereof wherein said peptide or variant has an overall length of between 8 and 100, preferably between 8 and 30, and most preferred between 8 and 16, namely 8, 9, 10, 11, 12, 13, 14, 15, 16 amino acids.

For MHC class II restricted peptides, several different peptides with the same core sequence may be presented in the MHC molecule. As the interaction with the recognizing T (helper) cell is defined by a core sequence of 9 to 11 amino acids, several length variants may be recognized by the same T (helper) cell clone. Thus, several different lengths variants of a core binding sequence may be used for direct loading of MHC class II molecules without the need for further processing and trimming at the N- or C-terminal ends. Correspondingly, naturally occurring or artificial variants that induce T cells cross-reacting with a peptide of the invention are often length variants.

If a peptide that is longer than around 12 amino acid residues is used directly to bind to a MHC class II molecule, it is preferred that the residues that flank the core HLA binding region are residues that do not substantially affect the ability of the peptide to bind specifically to the binding groove of the MHC class II molecule or to present the peptide to the T (-helper) cell. However, as already indicated above, it will be appreciated that larger peptides may be used, e.g. when encoded by a polynucleotide, since these larger peptides may be fragmented by suitable antigen-presenting cells. However, in same cases it has been shown that the core sequence flanking regions can influence the peptide binding to MHC class II molecule or the interaction of the dimeric MHC:peptide complex with the TCR in both directions compared to a reference peptide with the same core sequence. Intramolecular tertiary structures within the peptide (e.g. loop formation) normally decrease the affinities to the MHC or TCR. Intermolecular interactions of the flanking regions with parts of the MHC or TCR beside the peptide binding grooves may stabilize the interaction. These changes in affinity can have a dramatic influence on the potential of a MHC class II peptide to induce T (helper) cell responses.

It is also possible, that MHC class I epitopes, although usually between 8-10 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

Accordingly, the present invention also provides peptides and variants of MHC class I epitopes wherein the peptide or variant has an overall length of between 8 and 100, preferably between 8 and 30, and most preferred between 8 and 16, namely 8, 9, 10, 11, 12, 13, 14, 15, 16 amino acids.

Of course, the peptide or variant according to the present invention will have the ability to bind to a molecule of the human major histocompatibility complex (MHC) class I or II. Binding of a peptide or a variant to a MHC complex may be tested by methods known in the art, for example those described in the literature for different MHC class II alleles (e.g. Vogt et al., 1994; Malcherek et al., 1994; Manici et al., 1999; Hammer et al., 1995; Tompkins et al., 1993; Boyton et al., 1998).

In a particularly preferred embodiment of the invention the peptide consists or consists essentially of an amino acid sequence according to SEQ ID NO: 1 to SEQ ID NO: 3.

The peptides according to the present invention can also consist of a continuous stretch of amino acids as depicted in SEQ ID NO: 1 to 3, wherein said stretch is a part of said sequence having a length of at least 8 amino acids (e.g. 8, 9, 10, 11, 12, 13, 14, 15, or 16), as long as a core sequence is present in said peptide, rendering it functional in eliciting an immuno-response as described herein.

"Consisting essentially of" shall mean that a peptide according to the present invention, in addition to the sequence according to any of SEQ ID NO: 1 to SEQ ID NO: 3 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is a fusion protein that comprises, for example, the 80 N-terminal amino acids of the HLA-DR antigen-associated invariant chain (p33, in the following "Ii") as derived from the NCBI, GenBank Accession-number X00497 (Strubin, M. et al 1984).

Examples of further preferred peptides include peptides having a specific HLA-subtype and that are capable of stimulating CD8 cells, and wherein the peptide comprises the specific anchor amino acid-motif as depicted in the following Table 6.

TABLE 6

HLA-subtypes and anchor motifs of preferred peptide according to SEQ ID NO: 24

| Peptide | HLA-subtype | | Position |
|---|---|---|---|
| | | | 1 2 3 4 5 6 7 8 9 |
| 24 | A*02 | Petide Code | V L C G P P P A V |
| | | Anchor motif | x L x x x x x x V |

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) J. Immunol. 159, 3230-3237, incorporated herein by reference. This approach involves making pseudopeptides containing changes involving the backbone, and not the orientation of side chains. Meziere et al (1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH=CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxycarbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, $3^{rd}$ d ed. CRC Press, 2005, which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley & Sons NY 1995-2000) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The web sites of companies such as Sigma-Aldrich provide information on specific reagents.

Selective reduction of disulfide bonds in proteins is also common. Disulfide bonds can be formed and oxidized during the heat treatment of biopharmaceuticals.

Woodward's Reagent K may be used to modify specific glutamic acid residues. N-(3-(dimethylamino)propyl)-N'-ethylcarbodimide can be used to form intra-molecular crosslinks between a lysine residue and a glutamic acid residue.

For example, diethylpyrocarbonate is a reagent for the modification of histidyl residues in proteins. Histidine can also be modified using 4-hydroxy-2-nonenal.

The reaction of lysine residues and other α-amino groups is, for example, useful in binding of peptides to surfaces or the cross-linking of proteins/peptides. Lysine is the site of attachment of poly(ethylene)glycol and the major site of modification in the glycation of proteins. Methionine residues in proteins can be modified with e.g. iodoacetamide, bromoethylamine, and chloramine T. Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethyleneglycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lu et al (1981) and references therein. Temporary N-amino group protection is afforded by the 9-fluorenylmethyloxycarbonyl (Fmoc) group. Repetitive cleavage of this highly base-labile protecting group is done using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/lhydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, Bruckdorfer et al. 2004, and the references as cited therein).

Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from e.g. Calbiochem-Novabiochem (UK) Ltd, Nottingham NG7 2QJ, UK.

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitril/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

A further aspect of the invention provides a nucleic acid (for example a polynucleotide) encoding a peptide or peptide variant of the invention. The polynucleotide may be, for example, DNA, cDNA, PNA, CNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide or peptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc, New Haven, C N USA.

A desirable method of modifying the DNA encoding the polypeptide or peptide of the invention uses the polymerase chain reaction as disclosed by (Saiki et al (1988)). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide or peptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell. Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the fl origin. Vectors containing the preprotrypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of 10801 University Boulevard, Manassas, Va.

20110-2209 (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells, which are human embryonic kidney cells. Preferred insect cells are Sf9 cells, which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well known methods that typically depend on the type of vector used. With regard to transformation of prokaryotic host cells, see, for example, Cohen et al (1972) Proc. Natl. Acad. Sci. USA 69, 2110, and Sambrook et al (1989) Molecular Cloning, A Laboratory Manual, Cold Spring Harbor Laboratory, Cold Spring Harbor, N.Y. Transformation of yeast cells is described in Sherman et al (1986) Methods In Yeast Genetics, A Laboratory Manual, Cold Spring Harbor, N.Y. The method of Beggs (1978) Nature 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment, the host cell is an antigen presenting cell, in particular a dendritic cell or antigen presenting cell. APCs loaded with a recombinant fusion protein containing prostatic acid phosphatase (PAP) are currently under investigation for the treatment of prostate cancer (Sipuleucel-T) (Small E J et al 2006; Rini et al 2006).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 µg and 1.5 mg, preferably 125 µg to 500 µg, of peptide or DNA may be given and will depend on the respective peptide or DNA. Doses of this range were successfully used in previous trials (Brunsvig et al 2006; Staehler et al 2007).

Another aspect of the present invention includes an in vitro method for producing activated T cells, the method comprising contacting T-cells in vitro with antigen loaded human class I or II MHC molecules expressed on the surface of a suitable antigen-presenting cell for a period of time sufficient to activate the T-cell in an antigen specific manner, wherein the antigen is a peptide according to the invention. Preferably, a sufficient amount of the antigen is used with an antigen-presenting cell.

In the case of a MHC class II epitope being used as an antigen, the T-cells are CD4-positive helper cells, preferably of $T_{H1}$-type. The MHC class II molecules may be expressed on the surface of any suitable cell. Preferably the cell does not naturally express MHC class II molecules (in which case the cell has been transfected in order to express such a molecule). Alternatively, if the cell naturally expresses MHC class II molecules, it is preferred that it is defective in the antigen-processing or antigen-presenting pathways. In this way, it is possible for the cell expressing the MHC class II molecule to be completely loaded with a chosen peptide antigen before activating the T-cell.

The antigen-presenting cell (or stimulator cell) typically has MHC class II molecules on its surface and preferably is itself substantially incapable of loading said MHC class II molecule with the selected antigen. The MHC class II molecule may readily be loaded with the selected antigen in vitro.

Preferably, the mammalian cell lacks or has a reduced level or function of the TAP peptide transporter. Suitable cells that lack the TAP peptide transporter include T2, RMA-S and *Drosophila* cells. TAP is the Transporter associated with Antigen Processing.

The human peptide loading deficient cell line T2 is available from the American Type Culture Collection, 12301 Parklawn Drive, Rockville, Md. 20852, USA under Catalogue No CRL 1992; the *Drosophila* cell line Schneider line 2 is available from the ATCC under Catalogue No CRL 19863; the mouse RMA-S cell line is described in Karre et al. 1985.

Preferably, the host cell before transfection expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class II molecules and of the costimulator molecules are publicly available from the GenBank and EMBL databases.

Similarly, when a MHC class I epitope is used as an antigen, the T cells are CD8-positive CTLs.

If an antigen-presenting cell is transfected to express such an epitope, preferably the cell comprises an expression vector capable of expressing a peptide containing SEQ ID NO: 1 to SEQ ID NO: 3 or a variant amino acid sequence thereof.

A number of other methods may be used for generating CTL in vitro. For example, the methods described in Peoples et al. (1995) and Kawakami et al (1992) use autologous tumor-infiltrating lymphocytes in the generation of CTL. Plebanski et al. (1995) makes use of autologous peripheral blood lymphocytes (PLBs) in the preparation of CTL. Jochmus et al. (1997) describes the production of autologous CTL by pulsing dendritic cells with peptide or polypeptide, or via infection with recombinant virus. Hill et al. (1995) and Jerome et al. (1993) make use of B cells in the production of autologous CTL. In addition, macrophages pulsed with peptide or polypeptide, or infected with recombinant virus, may be used in the preparation of autologous CTL. S. Walter et al. 2003 describe the in vitro priming of T cells by using artificial antigen presenting cells (aAPCs), which is also a suitable way for generating T cells against the peptide of choice. In this study, aAPCs were generated by the coupling of preformed MHC:peptide complexes to the surface of polystyrene particles (microbeads) by biotin:streptavidin biochemistry. This system permits the exact control of the MHC density on aAPCs, which allows to selectively elicit high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore such aAPC-based systems often require the addition of appropriate soluble factors, e.g. cytokines like interleukin-12.

Allogeneic cells may also be used in the preparation of T cells and a method is described in detail in WO 97/26328, incorporated herein by reference. For example, in addition to Drosophila cells and T2 cells, other cells may be used to present antigens such as CHO cells, baculovirus-infected insect cells, bacteria, yeast, vaccinia-infected target cells. In addition plant viruses may be used (see, for example, Porta et al. (1994)) which describes the development of cowpea mosaic virus as a high-yielding system for the presentation of foreign peptides.

The activated T-cells that are directed against the peptides of the invention are useful in therapy. Thus, a further aspect of the invention provides activated T cells obtainable by the foregoing methods of the invention. Activated T cells, which are produced by the above method, will selectively recognize a cell that aberrantly expresses a polypeptide that comprises an amino acid sequence of SEQ ID NO: 1 to SEQ ID NO: 3.

Preferably, the T-cell recognizes the cell by interacting through its TCR with the HLA/peptide-complex (for example, binding). The T-cells are useful in a method of killing target cells in a patient whose target cells aberrantly express a polypeptide comprising an amino acid sequence of the invention wherein the patient is administered an effective number of the activated T-cells. The T-cells that are administered to the patient may be derived from the patient and activated as described above (i.e. they are autologous T-cells). Alternatively, the T-cells are not from the patient but are from another individual. Of course, it is preferred if the individual is a healthy individual. By "healthy individual" the inventors mean that the individual is generally in good health, preferably has a competent immune system and, more preferably, is not suffering from any disease which can be readily tested for, and detected.

In vivo, the target cells for the CD4-positive T-cells according to the present invention can be cells of the tumor (which sometimes express MHC class II) and/or stromal cells surrounding the tumor (tumor cells) (which sometimes also express MHC class II (Dengjel et al., 2006)).

The T-cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T-cells as defined above.

By "aberrantly expressed" the inventors also mean that the polypeptide is over-expressed compared to normal levels of expression or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T-cells may be obtained by methods known in the art, e.g. those described above. Protocols for this so-called adoptive transfer of T-cells are well known in the art and can be found, e.g. in (Rosenberg et al., 1987; Rosenberg et al., 1988; Dudley et al., 2002; Yee et al., 2002; Dudley et al., 2005); reviewed in (Gattinoni et al., 2006) and (Morgan et al., 2006).

Any molecule of the invention, i.e. the peptide, nucleic acid, expression vector, cell, activated CTL, T-cell receptor or the nucleic acid encoding it is useful for the treatment of disorders, characterized by cells escaping an immune response. Therefore any molecule of the present invention may be used as medicament or in the manufacture of a medicament. The molecule may be used by itself or combined with other molecule(s) of the invention or (a) known molecule(s).

Preferably, the medicament of the present invention is a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and Longenecker et al. (1993)). The peptide may also be tagged, may be a fusion protein, or may be a hybrid molecule. The peptides whose sequence is given in the present invention are expected to stimulate CD4 or CD8 T-cells. However, stimulation of CD8 CTLs is more efficient in the presence of help provided by CD4 T-helper cells. Thus, for MHC Class I epitopes that stimulate CD8 CTL, the fusion partner or sections of a hybrid molecule suitably provide epitopes that stimulate CD4-positive T cells. CD4- and CD8-stimulating epitopes are well known in the art and include those identified in the present invention.

In one aspect, the vaccine comprises at least one peptide having the amino acid sequence set forth in SEQ ID NO: 1, 2 or 3 and at least one additional peptide, preferably two to 50, more preferably two to 25, even more preferably two to 15 and most preferably two, three, four, five, six, seven, eight, nine, ten, eleven, twelve or thirteen peptides. The peptide(s) may be derived from one or more specific TAAs and may bind to MHC class I and/or class II molecules. Preferably the at least one additional peptide has the amino acid sequence set forth in SEQ ID NO: 4 to 24.

The polynucleotide may be substantially pure, or contained in a suitable vector or delivery system. The nucleic acid may be DNA, cDNA, PNA, CNA, RNA or a combination thereof. Methods for designing and introducing such a nucleic acid are well known in the art. An overview is provided by e.g. Pascolo S. 2006; Stan R. 2006, or A Mahdavi 2006. Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun," may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CTLs and helper-T ($T_H$) cells to an antigen, and would thus be considered useful in the medicament of the present invention. Suitable adjuvants include, but are not limited to, 1018 ISS, aluminium salts, AMPLIVAX®, AS15, BCG, CP-870,893, CpG7909, CyaA, dSLIM, flagellin or TLR5 ligands derived from flagellin, FLT3 ligand, GM-CSF, IC30, IC31, Imiquimod (ALDARA®), ImuFact IMP321, Interleukins as IL-2, IL-13, IL-21, Interferon-alpha or -beta, or pegylated derivatives thereof, IS Patch, ISS, ISCOMATRIX®, ISCOMs, JUVIMMUNE®, LIPOVAC®, MALP2, MF59, monophosphoryl lipid A, MONTANIDE® IMS 1312, MONTANIDE® ISA 206, MONTANIDE® ISA 50V, MONTANIDE® ISA-51, water-in-oil and oil-in-water emulsions, OK-432, OM-174, OM-197-MP-EC, ONTAK®, OspA, PepTel® vector system, PLG and dextran microparticles, resiquimod, SRL172, Virosomes and other Virus-like particles, YF-17D, VEGF trap, R848, beta-glucan, Pam3Cys, Aquila's QS21 STIMULON®, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Dupuis M et al. 1998; Allison 1998). Also cytokines may be used. Several cytokines have been directly linked to influencing dendritic cell migration to lymphoid tissues (e.g., TNF-α), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al. 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of $T_{H1}$ cells and strong cytotoxic T-lymphocyte (CTL) generation, even in the absence of CD4 T cell help. The $T_{H1}$ bias induced by TLR9 stimulation is maintained even in the presence of vaccine adjuvants such as alum or incomplete Freund's adjuvant (IFA) that normally promote a $T_{H2}$ bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg et al. 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany), which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and AMPLIGEN®, non-CpG bacterial DNA or RNA as well as immunoactive small molecules and antibodies such as cyclophosphamide, sunitinib, Bevacizumab, CELEBREX®, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4 and SC58175, which may act therapeutically and/or as an adjuvant. The amounts and concentrations of adjuvants and additives useful in the context of the present invention can readily be determined by the skilled artisan without undue experimentation. Preferred adjuvants are dSLIM, Interferon-alpha, -beta, CpG7909, IC31, ALDARA® (Imiquimod), PeviTer, RNA, tadalafil, temozolomide, and JUVIMMUNE®.

The present invention provides a medicament that useful in treating cancer, in particular glioma and brain cancer, breast cancer, prostate cancer, esophagus cancer, colorectal cancer, renal cancer, pancreatic cancer, squamous cell carcinomas and keratinocytic neoplasms of the skin, leukemia, lung cancer, ovarian cancer, and melanoma.

The present invention includes a kit comprising: (a) a container that contains a pharmaceutical composition as described above, in solution or in lyophilized form; (b) optionally a second container containing a diluent or reconstituting solution for the lyophilized formulation; and (c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contains instructions on or associated with the container that indicates directions for reconstitution and/or use. For example, the label may indicate that the lyophilized formulation is to be reconstituted to peptide concentrations as described herein. The label may further indicate that the formulation is useful or intended for subcutaneous administration.

The container holding the formulation may be a multi-use vial, which allows for repeat administrations (e.g., from 2 to 6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 μg) and preferably not more than 3 mg/mL/peptide (=1500 g). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, a anti-angiogenesis agent or inhibitor, a apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthalmic, subcutaneous, intradermal, intramuscular, intravenous or transdermal. Preferably the administration is s.c., and most preferably, i.d. Administration may be by infusion pump.

Regarding the sequencing listing, SEQ ID NO: 1 to SEQ ID NO: 3 show the sequences of the tumor associated peptide of the present invention derived from survivin.

SEQ ID NO: 4 to SEQ ID NO: 13 and SEQ ID NO: 24 show the sequences of other tumor associated peptides used in the present invention. SEQ ID NO: 14 shows the sequences of the peptide of HBV. SEQ ID NO: 15 to SEQ ID NO: 23 show the sequences of other tumor associated peptides used in the present invention. SEQ ID NO: 25 to SEQ ID NO: 27 show the sequences of the associated peptides of Wang et al. (WO 2007/036638). SEQ ID NO: 28 to SEQ ID NO: 33 show the sequences of tumor associated peptides of Piesche. SEQ ID NO: 34 to SEQ ID NO: 63 show the sequences of the Peptides as designed in Example 3. SEQ ID NO: 64 and SEQ ID NO: 65 show the sequences of the Peptides as used in Example 4.

The present invention will now be described in the following examples that describe preferred embodiments thereof, nevertheless, without being limited thereto. For the purposes of the present invention, all references as cited herein are incorporated by reference in their entireties.

EXAMPLES

Example 1

Identification of Tumor Associated Peptides Presented on Cell Surface

Tissue Samples

Patients' tumor and healthy tissues were provided by Hôpital Cantonal Universitaire de Genève (Medical Oncology Laboratory of Tumor Immunology) and Neurochirurgische Universitäts-Klinik Heidelberg (Molekularbiologisches Labor). Written informed consents of all patients had been given before surgery. Tissues were shock-frozen in liquid nitrogen immediately after surgery and stored until isolation of peptides at −80° C.

Isolation of HLA Peptides from Tissue Samples

HLA peptide pools from shock-frozen tissue samples were obtained by immune precipitation from solid tissues according to a slightly modified protocol (Falk, K. et al 1991; Seeger, F. H. et al. T 1999) using the HLA-A*02-specific antibody BB7.2 or the HLA-A, -B, -C-specific antibody W6/32, CNBr-activated sepharose, acid treatment, and ultrafiltration.

Method Two:

The HLA peptide pools as obtained were separated according to their hydrophobicity by reversed-phase chromatography (Acquity HPLC system, Waters) and the eluting peptides were analyzed in an LTQ—Orbitrap hybrid mass spectrometer (ThermoElectron) equipped with an ESI source. Peptide pools were loaded directly onto the analytical fused-silica micro-capillary column (75 μm i.d.×250 mm) packed with 1.7 μm C18 reversed-phase material (Waters) applying a flow rate of 400 mL per minute. Subsequently, the peptides were separated using an two-step 180 minute-binary gradient from 10% to 33% B at flow rates of 300 mL per minute. The gradient was composed of Solvent A (0.1% formic acid in water) and solvent B (0.1% formic acid in acetonitrile). A gold coated glass capillary (PicoTip, New Objective) was used for introduction into the micro-ESI source. The LTQ-Orbitrap mass spectrometer was operated in the data-dependent mode using a TOP5 strategy. In brief, a scan cycle was initiated with a full scan of high mass accuracy in the orbitrap (R=30 000), which was followed by MS/MS scans also in the orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide. FIG. 1 shows an exemplary spectrum obtained from tumor tissue for the MHC class I associated peptide NCAN-001.

Example 2

Expression Profiling of Genes Encoding the Peptides of the Invention

Not all peptides identified as being presented on the surface of tumor cells by MHC molecules are suitable for immunotherapy, because the majority of these peptides are derived from normal cellular proteins expressed by many cell types. Only few of these peptides are tumor-associated and likely able to induce T cells with a high specificity of recognition for the tumor from which they were derived. To identify such peptides and minimize the risk for autoimmunity induced by vaccination the inventors focused on those peptides that are derived from proteins that are over-expressed on tumor cells compared to the majority of normal tissues.

The "ideal" peptide will be derived from a protein that is unique to the tumor and not present in any other tissue. To identify peptides that are derived from genes with an expression profile similar to the "ideal" peptide, the identified peptides were assigned to the proteins and genes, respectively, from which they were derived and expression profiles of these genes were generated.

RNA Sources and Preparation

Surgically removed tissue specimens were provided by two different clinical sites (see Example 1) after written informed consent had been obtained from each patient. Tumor tissue specimens were snap-frozen in liquid nitrogen immediately after surgery and later homogenized with mortar and pestle under liquid nitrogen. Total RNA was prepared from these samples using TRIzol (Invitrogen, Karlsruhe, Germany) followed by a cleanup with RNEASY® (QIAGEN, Hilden, Germany); both methods were performed according to the manufacturer's protocol.

Total RNA from healthy human tissues was obtained commercially (Ambion, Huntingdon, UK; Clontech, Heidelberg, Germany; Stratagene, Amsterdam, Netherlands; BioChain, Hayward, Calif., USA). The RNA from several individuals (between 2 and 123 individuals) was mixed such that RNA from each individual was equally weighted. Leukocytes were isolated from blood samples of 4 healthy volunteers.

Quality and quantity of all RNA samples were assessed on an Agilent 2100 Bioanalyzer (Agilent, Waldbronn, Germany) using the RNA 6000 Pico LabChip Kit (Agilent).

Microarray Experiments

Gene expression analysis of all tumor and normal tissue RNA samples was performed by Affymetrix Human Genome (HG) U133A or HG-U133 Plus 2.0 oligonucleotide microarrays (Affymetrix, Santa Clara, Calif., USA). All steps were carried out according to the Affymetrix manual. Briefly, double-stranded cDNA was synthesized from 5-8 µg of total RNA, using SuperScript RTII (Invitrogen) and the oligo-dT-T7 primer (MWG Biotech, Ebersberg, Germany) as described in the manual. In vitro transcription was performed with the BioArray High Yield RNA Transcript Labelling Kit (ENZO Diagnostics, Inc., Farmingdale, N.Y., USA) for the U133A arrays or with the GeneChip IVT Labelling Kit (Affymetrix) for the U133 Plus 2.0 arrays, followed by cRNA fragmentation, hybridization, and staining with streptavidin-phycoerythrin and biotinylated anti-streptavidin antibody (Molecular Probes, Leiden, Netherlands). Images were scanned with the Agilent 2500A GeneArray Scanner (U133A) or the Affymetrix Gene-Chip Scanner 3000 (U133 Plus 2.0), and data were analyzed with the GCOS software (Affymetrix), using default settings for all parameters. For normalization, 100 housekeeping genes provided by Affymetrix were used. Relative expression values were calculated from the signal log ratios given by the software and the normal sample was arbitrarily set to 1.0.

The expression profile of the source gene NCAN of the peptide NCAN-001 of the present invention shows a high expression in glioblastoma tumor tissue whereas the gene is not expressed or expressed at very low levels in normal tissues (FIG. 2).

Example 3

HLA-DR Motif Peptides from Survivin (Swissprot: O15392)

Epitope Prediction: Prediction of potential HLA-DR ligands was carried out using the database SYFPEITHI.

Briefly, the sequence of survivin was screened against a matrix pattern which evaluates every amino acid within the nonamer core sequence of 15mer peptides fitting the respective HLA-DR motif. Anchor residues are given values of up to 10; other residues values up to 3, reflecting amino acid preferences for certain positions within the peptide. The theoretical maximum score for a candidate peptide varies from 28 to 43; scores for abundant natural ligands are typically above 20. TLGEFLKLDRERAKN (SEQ ID NO: 1) (or truncated versions) appears among the top scoring peptides in 5 of 6 predictions.

```
DRB1*01 (maximal theoretical score 43)
   58 FFCFKELEGWEPDDD          (SEQ ID NO: 34)   36

98 LGEFLKLDRERAKNK          (SEQ ID NO: 35)   28

22 FKNWPFLEGCACTPE          (SEQ ID NO: 36)   28

DRB1*03 (maximal theoretical score 40)
   99 GEFLKLDRERAKNKI          (SEQ ID NO: 37)   29

10 WQPFLKDHRISTFKN          (SEQ ID NO: 38)   26

3 APTLPPAWQPFLKDH          (SEQ ID NO: 39)   25

DRB1*04 (maximal theoretical score 28)
   98 LGEFLKLDRERAKNK          (SEQ ID NO: 40)   28

10 WQPFLKDHRISTFKN          (SEQ ID NO: 41)   28

3 APTLPPAWQPFLKDH          (SEQ ID NO: 42)   26

DRB1*07 (maximal theoretical score 34)
  121 KKEFEETAEKVRRAI          (SEQ ID NO: 43)   24

128 AEKVRRAIEQLAAMD          (SEQ ID NO: 44)   24

3 APTLPPAWQPFLKDH          (SEQ ID NO: 45)   22

16 DHRISTFKNWPFLEG          (SEQ ID NO: 46)   20

28 LEGCACTPERMAEAG          (SEQ ID NO: 47)   18

40 EAGFIHCPTENEPDL          (SEQ ID NO: 48)   18

93 FEELTLGEFLKLDRE          (SEQ ID NO: 49)   16

103 KLDRERAKNKIAKET          (SEQ ID NO: 50)   16

DRB1*11 (maximal theoretical score 38)
   98 LGEFLKLDRERAKNK          (SEQ ID NO: 51)   32

83 GCAFLSVKKQFEELT          (SEQ ID NO: 52)   24

58 FFCFKELEGWEPDDD          (SEQ ID NO: 53)   22

DRB1*15 (maximal theoretical score 34)
   95 ELTLGEFLKLDRERA          (SEQ ID NO: 54)   30

19 ISTFKNWPFLEGCAC          (SEQ ID NO: 55)   28

55 AQCFFCFKELEGWEP          (SEQ ID NO: 56)   28
```

Steps Leading to the Decision about the Sequence

1. For each peptide, a 9mer core sequence is necessary for HLA-DR binding. Predicted core sequences:

```
DRB1*01      FLKLDRERA       (SEQ ID NO: 57)

DRB1*03      LKLDRERAK       (SEQ ID NO: 58)

DRB1*04      FLKLDRERA       (SEQ ID NO: 59)

DRB1*11      FLKLDRERA       (SEQ ID NO: 60)

DRB1*15      LGEFLKLDR       (SEQ ID NO: 61)
```

2. Combine core sequences to obtain one promiscuitive core sequence:
Combined: LGEFLKLDRERAK (SEQ ID NO: 62)
3. Add flanking sequences to a final length of 15 amino acids:
Final: TLFEFLKLDRERAK (SEQ ID NO: 63)

Example 4

Clinical Study

A clinical study was conducted to confirm the immunogenicity of the peptide with the SEQ ID NO: 1. The primary study objective was the investigation of the PSA (prostate-specific antigen)-based response (PSA-R) to the subcutaneous administration of a prostate-specific peptide panel (vaccination therapy) in patients with biochemical relapse after radical prostatectomy without detection of manifest metastatic lesions.

The secondary study objective was the investigation of the tolerability and feasibility of administering vaccination therapy in patients with prostate carcinoma with special consideration of immunological phenomena in terms of a T cell response.

The study was designed as a prospective, randomized Phase I/II study for the indication of "biochemical relapse after radical prostatectomy without detection of manifest metastatic lesions."

Study Population

As part of this Phase I/II study, an attempt was made to induce PSA regression as an indicator of cessation of tumor growth by means of vaccination with a prostate-specific peptide panel in HLA-A*02+ patients with biochemical relapse after radical prostatectomy. A combination of prostate-specific peptides was administered subcutaneously with evaluation of the extent of the respective immune response in the context of various administration forms of the antigenic structures.

In contrast to previous vaccination studies, the planned study targeted the treatment of patients with a small tumor burden not yet detectable by imaging procedures. The patients were all immunized in the same way using known prostate-specific antigenic structures to enhance the immune response to the malignantly transformed cells. Nineteen patients were treated.

TABLE 7

Study population

| | Total | % | Median | Range |
|---|---|---|---|---|
| Age | 19 | | 63 | 55-77 |
| Prior neo-/adjuvant treatment | | | | |
| None | 11 | 58 | | |
| Radiation | 3 | 16 | | |
| Intermittent Hormonal Therapy | 2 | 11 | | |
| Rad. + Int. Horm. Therapy | 2 | 11 | | |
| Rad. + Chemotherapy | 1 | 5 | | |
| TNM at RPX | | | | |
| T2a-c R0 | 6 | 32 | | |
| T3a-c R0 | 6 | 32 | | |
| T2a-c R1 | 3 | 16 | | |
| T3a-c R1 | 3 | 16 | | |
| T3aN2 R0 | 1 | 5 | | |
| Gleason score | | | | |
| 5-7 | 10 | 53 | | |
| 8-10 | 3 | 16 | | |
| unknown | 6 | 32 | | |

TABLE 7-continued

Study population

| | Total | % | Median | Range |
|---|---|---|---|---|
| RPX prior to vaccination in months | | | 41 | 9-124 |
| First relapse post OP in months | | | 14 | 1-90 |
| PSA at vaccination start | | | 0.76 | 0.14-10.8 |

Treatment Schedule

After rule-out of manifest metastatic lesions using computed tomography and skeletal scintigraphy, the prostate-specific peptide vaccine was subcutaneously administered according to the different administration forms to patients with detected PSA relapse after prior radical prostatectomy (PSA increase in terms of a 50% elevated value during two measurements at least 14 days apart). The vaccine was administered 8× on days 0, 7, 14, 28, 42, and 56 (approximately 100 micrograms per peptide and injection each time). After each vaccination treatment and again on day 70, PSA was measured to evaluate the therapeutic response.

If a tumor response (complete remission [PSA-CR], partial remission [PSA-PR], or stable clinical course [no change, PSA-NC]) is detected, the patient received the vaccine once a month as maintenance therapy according to the selected administration form. The patient's response to vaccination therapy was evaluated in detail as follows:

Complete remission (PSA-CR): Normalization of an initially elevated PSA level, confirmed by measurement after an interval of at least 4 weeks. Normalization is defined as a PSA nadir of <0.2 ng/ml, which would be expected after radical prostatectomy with complete tumor or prostate extirpation.

Partial remission: a) PSA-PR≤80% (Reduction in an initially elevated PSA level by 80%, confirmed by measurement after an interval of at least 4 weeks); and b) PSA-PR≤50% (Reduction in an initially elevated PSA level by 50%, confirmed by measurement after an interval of at least 4 weeks.)

Stable disease (PSA-SD): No significant change over a period of at least four weeks. This includes stabilization and a reduction of less than 50% and an increase of less than 10%, confirmed by measurement after an interval of at least 4 weeks.

Progression (PSA-PD): Increase in the PSA level by more than 10%. In the event of PSA progression, the study was terminated.

After enrollment of the patients in the study, the epitope-specific vaccine was used; the proteins specifically expressed in prostatic epithelial cells (e.g., PSMA/PSCA) were taken into account. In addition to investigating the general efficacy of the administered vaccine with respect to monitoring the growth of residual tumor fractions as evaluated by PSA monitoring, this study investigated the effects of various vaccination methods with respect to efficient modulation of the immune system. In addition to simple subcutaneous administration of the peptides according to the invention alone, various combinations with adjuvants were also used. The vaccine included a combination of at least 6 peptides derived from PSA, PSCA, PSMA, Survivin, TRP-P8 and Prostein, respectively. A peptide derived from influenza MP was used as a positive control. Peptides derived from PSMA and Survivin were used at T helper epitopes. In particular, depot and adjuvant activity for peptide vaccines of MONTANIDE® (a formulation of the classical incomplete Freund's adjuvant suitable for use in humans), which has recently been described very favorably, was used. For this purpose, 500 μl of the peptide solution was mixed with 500 μl of MONTANIDE® and administered. Thereby, a water-in-oil emulsion is built that slowly releases the antigen contained in the aqueous phase over weeks. The physical stability of the emulsion is very high, as at 4° C. it can be stored for more than 3 months without significant phase separation. The depot function of MONTANIDE® has been exploited in several vaccination trials with good results (Okat et al., 2004).

One study arm investigated the efficacy of vaccination during concomitant stimulation of the immune system by growth factors, GM-CSF, Leukine® solution for injection. GM-CSF is a very commonly used adjuvant in peptide vaccination trials with several thereof reporting enhanced clinical and T-cell responses. Initially, GM-CSF is a dendritic cell recruitment and differentiation factor that is thought to enhance the number of dendritic cell at the vaccines' injection site. Although GM-CSF does not by itself activate antigen presenting cells as dendritic cells and macrophages an indirect activation in vivo has been reported (Molenkamp et al., 2005).

Another study arm investigated the efficacy of vaccination during concomitant activation of dendritic cells by epicutaneous use of imiquimod. Imiquimod was administered as a 5% ointment (ALDARA®). It has a strong immunostimulatory via its effect on TLR7 positive cells (e.g. plasmacytoid DCs, Langerhans cells, dermal DCs), activates the MyD88-dependent pathway. Activated APCs release T-cell stimulating and inflammatory cytokines, upregulate costimulation and migrate to draining lymph nodes. The potential of iniquimod to enhance peptide-induced CTL response by mixing the antigens into the ointment or by application of ALDARA® over the s.c. or i.d. injection site for the antigens has been demonstrated in animal models.

Another study arm investigated the efficacy of vaccination during concomitant activation of dendritic cells by mixing them with protamine-stabilized mRNA encoding mucin-1 to activate TLR 7/8. mRNA shows a broad activation of mouse and human immune cell populations. The presence of the poly-basic protein protamine in the formulation increases the half-life of the mRNA and induces the formation of potentially depot-forming particles. This adjuvant may therefore combine depot-forming and APC-activating properties.

In summary, the administration forms of the vaccine included the following approaches:

a) Subcutaneous administration of the peptide vaccine emulsified in MONTANIDE®;

b) Subcutaneous administration of the peptide vaccine emulsified in 500 μl of MONTANIDE® in combination with topical administration of 225 μl of GM-CSF with the objective of achieving a stronger immune response triggered by concomitant administration of growth factors;

c) Subcutaneous administration of the peptide vaccine emulsified in 500 μl of MONTANIDE® in combination with local hyperthermia, the latter given with the objective of achieving a thermally induced stronger immune response;

d) Subcutaneous administration of the peptide vaccine emulsified in 500 μl of MONTANIDE® in combination with epicutaneous imiquimod in order to activate dendritic cells via TLR 7;

e) Subcutaneous administration of the peptide vaccine emulsified in 500 μl of MONTANIDE® together with 55 μl of mucin-1 mRNA/protamine to activate dendritic cells via TLR 7/8.

Schedule

The entire duration of the study was 3 years. Prostate-specific peptide vaccines were administered to patients on days 0, 7, 14, 28, 42, and 56. In patients with stable disease or an objective tumor response (PSA-CR or PSA-PR), the vaccinations were administered once a month i.d. until detectable progression occurs. On the basis of the experience available thus far, peptide injections are tolerated without significant adverse reactions. Because the response to vaccination therapy was evaluated solely serologically on the basis of the PSA measurement, a test was performed at the start of the study to determine whether the administered vaccine interferes with PSA measurement in vitro, which could simulate a clinical response. On days 0, 7, 14, 28, 42, 56, and 70, blood samples was taken for laboratory tests, PSA levels, differential blood count, FACS analysis, and cytokines. If treatment is continued past day 70, 6-week PSA monitoring was performed to detect treatment failure in a timely manner.

Treatment was ended if documented progression of the disease occurred in terms of a continuous PSA elevation.

Beginning on day 84, immunization therapy was continued at 4-week intervals until documented progression or up to day 420 (15 months). Decisions regarding continuation of therapy (in successful cases) outside of this study were made on a case-by-case basis. Unexpected adverse reactions did not occur in this study.

The laboratory tests included coagulation, electrolytes, LDH, B2-M, CK, hepatic enzymes, bilirubin, creatinine, uric acid, total protein, coagulation, CRP, differential blood count with smear, PSA level, cytokines, FACS, ELISPOT®.

Analysis of the cutaneous reaction to defined bacterial and fungal antigens (48-72 hours after administration, delayed type hypersensitivity (DTH), T cell-mediated, served as an analysis of the patient's cellular immune system before the start of the study).

The peptides required for the study (nona-peptides) were manufactured in the laboratory of PD Dr. Stefan Stevanovic in the department of Prof. H.-G. Rammensee. These peptides were purified by HPLC and analyzed by mass spectrometry. The purity of the peptides can also be checked by HPLC, mass spectrometry, and Edman sequencing. Using these methods, purity of up to 98% can be documented (which must be regarded as the maximum according to the current state of the methods). The synthesized peptides was dissolved in DMSO (CryoSure, WAK Chemie Medical GmbH; 10 mg/ml), diluted to 1:10 in Ampuwa (Fresenius Kabi), and aliquoted under sterile conditions.

Clinical Response

In two patients PET-CT scan could reveal local recurrence after local tumor was detected by continuous digital rectal examination. In the remaining 17 patients the location of disease activity could not be verified at study termination.

Repeated laboratory evaluation of differential blood count or extensive clinical chemistry did not reveal any abnormalities nor changes during the study.

Of the 19 patients, 16 patients reacted to the Survivin II peptide (IFN-g ELISPOT, +/− ICS) according to SEQ ID NO: 1. Among them were 12 patients with induction of an anti-survivin T-cell response upon vaccination, 2 with pre-existing anti-Survivin T cells and 2 patients of whom it was not determined, whether pre-existing anti-Survivin T cells were abundant.

Biochemical Response

Complete response was considered as a non-detectable PSA value according to the lowest value detected after initially elevated PSA. The measurement had to be confirmed after an interval of at least four weeks. A PR>80% and >50% had to be reevaluated after four weeks accordingly. A PSA within the range of less than 50% decrease or less than 10% increase reflected stable disease if at least confirmed after four weeks. Progressive disease was considered any increase of more than 10% of PSA at treatment start.

Biochemical response in patients who terminated the study was followed until they received further treatment with local radiation or antihormonal therapy. 19 patients consented to participate and the data was analyzed with the longest follow-up lasting about 3.75 years.

PSA Stability and DT Increase

PSA values of two patients (10.2%) exhibited stability according to the above mentioned criteria of biochemical response which state that no rise of the PSA value greater than 10% at treatment start had occurred at study end (FIG. 6, Tables 8, 9, and 10). Follow up in those two cases was conducted 14 and 16 months after the last vaccine application. Average duration of stability was 24 months (28 and 31) at data cut-off with an average of 18 vaccinations (14 and 20) applied.

Out of these two patients, one patient showed partial response>50% for a period of 9 months, followed by a period of slow PSA rise with a doubling time of 20.5 compared to 9.8 months prior vaccination. Initial PSA relapse started 18 months post surgery for a pT2pN0 Gleason 5 tumor.

At data analysis, Patient 8 exhibited stable disease since the beginning of the vaccination program. Patients stopped treatment due to an allergic reaction after 10 months and the 14$^{th}$ vaccination. The patient had an unfavorable pT3b Gleason 3+4 situation with a PSA nadir after radical prostatectomy not below 0.6 ng/ml and PSA progression without timely delay after initial decline postoperatively. Doubling time slowed from 6.6 months to 148 months.

These two patients received dermal Imiquimod at the application site at each peptide vaccination (FIGS. 9, 10, and 11, Table 13).

PSA DT Increase without PSA Stability

PSA DT of Patient 11 was increased from 1.5 to 10.1 months during six months in the study. Since the patient started with a PSA of 10.8 ng/ml and progressed to 17.8 ng/ml, the patient terminated the study to receive antiandrogen monotherapy without any malignant lesions visualized in PET-CT. The patient received ALDARA® as adjuvant.

Patient 16 started into vaccine treatment plus Mucin-1-mRNA/protamine with a doubling time of 6.1 months. PSA velocity declined into a half life time of 2.7 months for five months followed by a statistically calculated rise of PSA DT of 14.4 months which is continuing 16 months after treatment start. With an initial PSA of 0.29 ng/ml, he dropped to 0.19 ng/ml during the first 5 months on study treatment, rose to 0.4 ng/ml within the following 8 months and terminated the study per protocol with 0.41 ng/ml 19 months after treatment start (FIG. 7 Table 8 and 10).

PSA Progression

Patient 5 progressed during the study according to the estimated PSA doubling time before vaccination. However, the patient experienced a PSA decline with a half-time life of 20.2 months after treatment end for a continuing period of 10 months at data cut-off. He still was not receiving any secondary treatment after vaccination end. He was vaccinated with MONTANIDE® as the only adjuvant (FIG. 8, Table 13).

TABLE 8

PSA Doubling Time in months

|  | Total | % | Geometric Mean | Range of DT |
|---|---|---|---|---|
| PSA DT prior vaccination in months | 19 |  | 8.3 | 1.5-44.8 |
| PSA DT at study end or at end of follow-up | 18* |  | 11.2 | 2.2-148 |
| No change of PSA DT during vaccination | 11 | 58 |  | 2.2-44.8 |
| Increased PSA DT continuing at end of study | 4 | 21 |  |  |
| No change of PSA DT during vacc but decline after | 1 | 5 |  |  |
| Interim PSA decline or DT increase followed by DT decrease | 3 | 16 |  |  |

*PSA DT at study end or end of follow-up was not included for Pat. 5 due to PSA decline

TABLE 9

PSA stability with no rise greater than 10% from baseline PSA

|  | $PSA_{baseline}$ ng/ml | $PSA_{end\ of\ study}$ ng/ml | $PSA_{end\ of\ follow\ up}$ ng/ml | $Months_{since\ baseline}$ |
|---|---|---|---|---|
| pat 3 | 0.7 | 0.51 | 0.73 | 31 |
| pat 8 | 1.76 | 1.84 | 1.85 | 28 |

TABLE 10

Permanent increase of PSA DT in months during vaccination

|  | 1$^{th}$ DT prior vaccine months | 2$^{th}$ DT during vaccine months | 3$^{th}$ DT during vaccine months |
|---|---|---|---|
| pat 3 | 9.8 | -2.3 | 20.5 |
| pat 8 | 6.6 | 148 |  |
| pat 11 | 1.5 | 10.1 |  |
| pat 16 | 6.1 | -2.7 | 14.4 |
| geometric mean DT | 4.9 | 25.8 |  |

TABLE 11

No change of PSA DT in months during vacc but decline after

|  | 1$^{th}$ DT prior vaccine months | 2$^{th}$ DT during vaccine months |
|---|---|---|
| pat 5 | 3.2 | -20.2 |

TABLE 12

Interim PSA DT decline/stability in months followed by accelerated rise

|  | 1$^{th}$ DT prior vaccine months | 2$^{th}$ DT during vaccine months | 3$^{th}$ DT during vaccine months | 4$^{th}$ DT during vaccine months |
|---|---|---|---|---|
| pat 7 | 3.7 | 21.5 | 2.8 |  |
| pat 15 | 1.3 | 25.8 | −9.9 | 7.4 |
| pat 17 | 10.2 | −1.9 | 4.8 |  |

TABLE 13

Adjuvants and patient response. No PSA response (−), interim PSA fall and accelerated rise after (+/−), PSA DT increase (+)

| No adjuvants | Response | ALDARA ® | Response | Hyperthermia | Response | GmCSF | Response | RNA | Response |
|---|---|---|---|---|---|---|---|---|---|
| pat 1 | − | pat 3 | + | pat 13 | − | pat 4 | − | pat 16 | + |
| pat 2 | − | pat 7 | +/− | pat 10 | − | pat 6 | − | pat 17 | +/− |
| pat 5 | − | pat 8 | + |  |  | pat 12 | − | pat 18 | − |
| pat 9 | − | pat 11 | + |  |  | pat 14 | − | pat 19 | − |
|  |  |  |  |  |  | pat 15 | +/− |  |  |

Synthesis

The peptides were synthesized using a fully automatically in the EPS 221 peptide synthesizer manufactured by Abimed. The synthesis program follows the manufacturer's standard protocols. To the extent possible, the batch numbers of the reagent batches are registered for each peptide.

Processing to the Raw Peptide

The processing of the raw peptide was done by splitting off of the synthesis resin and release of the side-chain protective groups by TFA/phenol/ethane dithiol/thioanisole/water (90/3.75/1.25/2.5/2.5, volume percent, respectively) 1 h or 3 h (peptides with arginine). Precipitation of the raw peptide in methyl-tert-butylether, washing with methyl-tert-butylether and twice with diethylether, drying and dissolution of the peptide pellet in acetic acid. Another precipitation in diethylether, drying, resuspension in water, and freeze-drying.

Preparative HPLC

HPLC system Varian "Star," chromatography column 250×10 mm C18 5 μm (Manufacturer Ziemer). Mobile solvent A: water with 0.1% TFA, mobile solvent B: acetonitrile with 0.08% TFA. The gradient used for separation is oriented to the hydrophobicity of the peptide. The separated peptide fractions are freeze-dried.

Analysis

For each peptide, an HPLC chromatogram and a MALDI mass spectrum were recorded to prove the identity (via the molar mass in the mass spectrum) and purity (via the peak areas in the HPLC chromatogram).

Synthetic Peptides and Stimuli

Synthetic peptides used for the stimulation and for functional tests were the HIV-derived epitope (HIV gag 164-181: YVDRFYKTLRAEQASQEV (SEQ ID NO: 65), negative control), PSMA 459-473: NYTLRVDCTPLMYSL (SEQ ID NO: 64) and Survivin 97-111: TLGEFLKLDRERAKN (SEQ ID NO: 1). Staphylococcus enterotoxin B (SEB, Sigma-Aldrich, Taufkirchen, Germany) was used as a positive control stimulation for CD4+ T-cells in the Interferon-γ ELISPOT.

In Vitro Amplification of Specific T-Cells

Peripheral blood mononuclear cells from prostate carcinoma patients were obtained at different time-points during vaccination and cryopreserved in 90% fetal calf serum and 10% DMSO in liquid nitrogen. After thawing, approximately 5×10$^6$ cells were cultivated (24-well cell culture plate, Greiner Bio-One, Frickenhausen, Germany) in IMDM medium supplemented with 50 U/ml Penicillin, 50 μg/ml Streptomycin (all Biowhittaker, Verviers, Belgium), 10% heat-inactivated human serum (c.c. pro, Neustadt, Germany) and 50 μM beta—mercaptoethanol at 37° C. and 7.5% CO$_2$. Pooled synthetic HLA-class II binding peptides were added at day 1, each at 5 μg/ml and the culture was supplemented with recombinant human IL-2 (r-hIL2, R&D Systems GmbH, Wiesbaden, Germany) at days 2, 5, 7 and 9 of the T-cell stimulation.

Enzyme-Linked Immunosorbent Spot (ELISPOT) Assay

The functionality of expanded T-cells was tested in a standard Interferon-γ ELISPOT assay according to the recommendations of the CIMT Monitoring Panel. Briefly, cells were harvested after the 12 day culture, washed, counted and seeded in culture medium on an ELISPOT plate (Millipore, Schwalbach, Germany). Between 0.15 and 0.25×10$^6$ cells were tested in duplicates or triplicates, in the presence of the synthetic peptides at 2.5 μg/ml or SEB at 1 μg/ml. Production of IFN-γ was detected with a pair of specific monoclonal antibodies (1D1-k and 7-B6-1, both Mabtech, Nacka Strand, Sweden) after 26 hour incubation at 37° C. and 5% CO$_2$. ExtraAvidin-Alkaline Phosphatase and BCIP/NBT substrate (both Sigma-Aldrich) were added for 1 hour and 10 min respectively. ELISPOT analysis was performed using ImmunoSpot readers (Series 3A and 5, Cellular Technology Ltd, Aalen, Germany).

Intracellular Cytokine Staining

Cells recovered from the ELISPOT were further cultivated in the presence of 2 ng/ml r-hIL2 for nine additional days. After this re-stimulation period, effectors were harvested, washed and stimulated in a standard assay with the peptides at 5 μg/ml or PMA and Ionomycin (50 ng/ml and 1 μM, respectively) in the presence of Golgi-STOP (BD Biosciences, Heidelberg, Germany) following the manufacturers instructions. Following an incubation period of 6 hours, cells were washed in PBS 1% FCS 0.02% NaN$_3$ and stained with monoclonal antibodies (MoAb) CD4-APC-Cy7 (BD Biosciences) and CD8-PE-Cy7 (Beckman Coulter) for 20 min at 4° C. in the dark. After a washing step, cells were permeabilized 20 min with Cytofix/Cytoperm reagent (BD Biosciences) then stained for intracellular cytokines for 30 min. MoAb used were IFN-γ-FITC, IL-10-PE (both BD Biosciences), IL-5-APC (Miltenyi Biotec, Bergisch Gladbach, Germany) and TNF-α-Pacific Blue (Biolegend, San Diego, Calif.). Cell acquisition was performed on a Cytometer Canto II using the software Diva and analysis with FlowJo (BD Biosciences).

Example 5

Binding of BIR-11, BIR-12, and BIR-13 to HLA-A*0211

The objective of this analysis was to evaluate the affinity of BIR-004 (ELTLGEFLKLDRERAKN (SEQ ID No: 2)) C-terminal peptides to the MHC molecule coded by the HLA-A*0211 allele as this an allele with reported capacity to bind peptides with C-terminal asparagine residues. MHC ligands with c-terminal N are not very frequent and to date only 66 peptides with N in the C-terminus have been tested. The vast majority of these peptides are non-binders, however, there are a few exceptions: RLYNFSFLN (SEQ ID No: 66) binds strongly to A*0211 and also YADGGQWYN (SEQ ID No: 67) binds to A*021.

The tests clearly indicated that binding to HLA-A*0211 has been found for BIR-11 (C-terminal nonamer: KLDRERAKN (SEQ ID No: 68)) and BIR-13 (C-terminal decamer: LKLDRERAKN (SEQ ID No: 69)) at higher concentrations but not for BIR-12 (C-terminal octamer: LDRERAKN (SEQ ID No: 70)). The positive control peptide (Sequence: FLPSDYFPSV (SEQ ID No: 71)) showed clear binding properties.

Principle of Test

An assay was set up as follows: Stable HLA/peptide complexes consist of three molecules: HLA heavy chain, beta-2 microglobulin (b2m) and the peptidic ligand. The activity of denatured recombinant HLA-A*0211 heavy chain molecules alone can be preserved making them functional equivalents of "empty HLA-A*0211 molecules." When diluted into aqueous buffer containing b2m and an appropriate peptide, these molecules fold rapidly and efficiently in an entirely peptide-dependent manner. The availability of these molecules is used in an ELISA-based assay to measure the affinity of interaction between peptide and HLA class I molecule {Sylvester-Hvid, 2002 SYLVESTERHVID2002/id}.

Purified recombinant HLA-A*0211 molecules were incubated together with b2m and graded doses of the peptide of interest. The amount of de novo-folded HLA/peptide complexes was determined by a quantitative ELISA. Dissociation constants ($K_D$ values) were calculated using a standard curve recorded from dilutions of a calibrant HLA/peptide complex. The deviance in the measurements was too big to give reliable $K_D$ values, although it can be said that the $K_D$ value for BIR13 is in the range of the positive control whereas the $K_D$ value for BIR-11 is higher. A lower $K_D$ value reflects higher affinity to HLA-A*0211.

Binding-Scores of the nonamer BIR-11 and the nonamer BIR-11a against several alleles using SYFPEITHI.

| | Allele-id | Allele name | Rel score | score |
|---|---|---|---|---|
| KLDRERAKD (SEQ ID NO: 72) | | | | |
| KLDRERAKD | 74 | A*0301 | 0.45 | 20 |
| KLDRERAKD | 65 | A*0201 | 0.42 | 15 |
| KLDRERAKD | 99 | B*1501 (B62) | 0.36 | 10 |
| KLDRERAKD | 334 | A*0101 | 0.28 | 14 |
| KLDRERAKN (SEQ ID NO: 68) | | | | |
| KLDRERAKN | 74 | A*0301 | 0.45 | 20 |
| KLDRERAKN | 65 | A*0201 | 0.42 | 15 |
| KLDRERAKN | 99 | B*1501 (B62) | 0.36 | 10 |
| KLDRERAKN | 334 | A*0101 | 0.28 | 14 |

REFERENCE LIST

Al-Joudi F S, Iskandar Z A, Imran A K (2007). Survivin expression correlates with unfavourable prognoses in invasive ductal carcinoma of the breast. Med J Malaysia 62, 6-8.

al-Sheneber I F, Shibata H R, Sampalis J, Jothy S (1993). Prognostic significance of proliferating cell nuclear antigen expression in colorectal cancer. Cancer 71, 1954-1959.

Angileri F F, Aguennouz M, Conti A, La T D, Cardali S, Crupi R, Tomasello C, Germano A, Vita G, Tomasello F (2008). Nuclear factor-kappaB activation and differential expression of survivin and Bcl-2 in human grade 2-4 astrocytomas. Cancer.

Apostolopoulos V, McKenzie I F (1994). Cellular mucins: targets for immunotherapy. Crit. Rev. Immunol. 14, 293-309.

Appay V, Speiser D E, Rufer N, Reynard S, Barbey C, Cerottini J C, Leyvraz S, Pinilla C, Romero P (2006). Decreased specific CD8+ T cell cross-reactivity of antigen recognition following vaccination with Melan-A peptide. Eur. J. Immunol. 36, 1805-1814.

Asher R A, Morgenstern D A, Fidler P S, Adcock K H, Oohira A, Braistead J E, Levine J M, Margolis R U, Rogers J H, Fawcett J W (2000). Neurocan is upregulated in injured brain and in cytokine-treated astrocytes. J. Neurosci. 20, 2427-2438.

Bamias A, Chorti M, Deliveliotis C, Trakas N, Skolarikos A, Protogerou B, Legaki S, Tsakalou G, Tamvakis N, Dimopoulos M A (2003). Prognostic significance of CA 125, CD44, and epithelial membrane antigen in renal cell carcinoma. Urology 62, 368-373.

Barnd D L, Lan M S, Metzgar R S, Finn O J (1989). Specific, Major Histocompatibility Complex-Unrestricted Recognition of Tumor-Associated Mucins by Human Cytotoxic T Cells. PNAS 86, 7159-7163.

Bates S, Bonetta L, MacAllan D, Parry D, Holder A, Dickson C, Peters G (1994). CDK6 (PLSTIRE) and CDK4 (PSK-J3) are a distinct subset of the cyclin-dependent kinases that associate with cyclin D1. Oncogene 9, 71-79.

Beilmann M, Vande Woude G F, Dienes H P, Schirmacher P (2000). Hepatocyte growth factor-stimulated invasiveness of monocytes. Blood 95, 3964-3969.

Berger M, Bergers G, Arnold B, Hammerling G J, Ganss R (2005). Regulator of G-protein signaling-5 induction in pericytes coincides with active vessel remodeling during neovascularization. Blood 105, 1094-1101.

Bertoletti A, Chisari F V, Penna A, Guilhot S, Galati L, Missale G, Fowler P, Schlicht H J, Vitiello A, Chesnut R C., (1993). Definition of a minimal optimal cytotoxic T-cell epitope within the hepatitis B virus nucleocapsid protein. J. Virol. 67, 2376-2380.

Bladt F, Riethmacher D, Isenmann S, Aguzzi A, Birchmeier C (1995). Essential role for the c-met receptor in the migration of myogenic precursor cells into the limb bud. Nature 376, 768-771.

Blum R, Jacob-Hirsch J, Rechavi G, Kloog Y (2006). Suppression of survivin expression in glioblastoma cells by the Ras inhibitor farnesylthiosalicylic acid promotes caspase-dependent apoptosis. Mol. Cancer. Ther. 5, 2337-2347.

Borset M, Seidel C, Hjorth-Hansen H, Waage A, Sundan A (1999). The role of hepatocyte growth factor and its receptor c-Met in multiple myeloma and other blood malignancies. Leuk. Lymphoma 32, 249-256.

Bottaro D P, Rubin J S, Faletto D L, Chan A M, Kmiecik T E, Vande Woude G F, Aaronson S A (1991). Identification of the hepatocyte growth factor receptor as the c-met proto-oncogene product. Science 251, 802-804.

Bowen A R, Hanks A N, Murphy K J, Florell S R, Grossman D (2004). Proliferation, apoptosis, and survivin expression in keratinocytic neoplasms and hyperplasias. Am J. Dermatopathol. 26, 177-181.

Boyton R J, Lohmann T, Londei M, Kalbacher H, Halder T, Frater A J, Douek D C, Leslie D G, Flavell R A, Altmann D M (1998). Glutamic acid decarboxylase T lymphocyte responses associated with susceptibility or resistance to type I diabetes: analysis in disease discordant human twins, non-obese diabetic mice and HLA-DQ transgenic mice. Int. Immunol. 10, 1765-1776.

Bramhall S R, Neoptolemos J P, Stamp G W, Lemoine N R (1997). Imbalance of expression of matrix metalloproteinases (MMPs) and tissue inhibitors of the matrix metalloproteinases (TIMPs) in human pancreatic carcinoma. J. Pathol. 182, 347-355.

Brossart P, Heinrich K S, Stuhler G, Behnke L, Reichardt V L, Stevanovic S, Muhm A, Rammensee H G, Kanz L, Brugger W (1999a). Identification of HLA-A2-restricted T-cell epitopes derived from the MUC 1 tumor antigen for broadly applicable vaccine therapies. Blood 93, 4309-4317.

Brossart P, Heinrich K S, Stuhler G, Behnke L, Reichardt V L, Stevanovic S, Muhm A, Rammensee H G, Kanz L, Brugger W (1999b). Identification of HLA-A2-restricted T-cell epitopes derived from the MUC 1 tumor antigen for broadly applicable vaccine therapies. Blood 93, 4309-4317.

Brossart P, Wirths S, Stuhler G, Reichardt V L, Kanz L, Brugger W (2000). Induction of cytotoxic T-lymphocyte responses in vivo after vaccinations with peptide-pulsed dendritic cells. Blood 96, 3102-3108.

Browner M F, Smith W W, Castelhano A L (1995). Matrilysin-inhibitor complexes: common themes among metalloproteases. Biochemistry 34, 6602-6610.

Burton E C, Prados M D (2000). Malignant gliomas. Curr. Treat. Options. Oncol 1, 459-468.

Cao Y, Karsten U, Zerban H, Bannasch P (2000). Expression of MUC 1, Thomsen-Friedenreich-related antigens, and cytokeratin 19 in human renal cell carcinomas and tubular clear cell lesions. Virchows Arch. 436, 119-126.

Casati C, Dalerba P, Rivoltini L, Gallino G, Deho P, Rini F, Belli F, Mezzanzanica D, Costa A, Andreola S, Leo E, Parmiani G, Castelli C (2003). The apoptosis inhibitor protein survivin induces tumor-specific CD8+ and CD4+ T cells in colorectal cancer patients. Cancer Res. 63, 4507-4515.

Castellino F, Huang A Y tan-Bonnet G, Stoll S, Scheinecker C, Germain R N (2006). Chemokines enhance immunity by guiding naive CD8+ T cells to sites of CD4+ T cell-dendritic cell interaction. Nature 440, 890-895.

CBTRUS. Primary Brain Tumors in the United States, Statistical Report. 2006. Ref Type: Internet Communication Chakravarti A, Noll E, Black P M, Finkelstein D F, Finkelstein D M, Dyson N J, Loeffler J S (2002). Quantitatively determined survivin expression levels are of prognostic value in human gliomas. J Clin Oncol 20, 1063-1068.

Chanock S J, Foster C B, Miller F W O'Hanlon T P (2004). HLA-A, -B, -Cw, -DQA1 and -DRB1 Alleles in a Caucasian Population from Bethesda, USA. Hum. Immunol. 65, 1211-1223.

Cheever M A, Chen W, Disis M L, Takahashi M, Peace D J (1993). T-cell immunity to oncogenic proteins including mutated ras and chimeric bcr-abl. Ann N.Y. Acad. Sci. 690, 101-112.

Chen X, Higgins J, Cheung S T, Li R, Mason V, Montgomery K, Fan S T, van de R M, So S (2004). Novel endothelial cell markers in hepatocellular carcinoma. Mod. Pathol. 17, 1198-1210.

Colombetti S, Basso V, Mueller D L, Mondino A (2006). Prolonged TCR/CD28 engagement drives IL-2-independent T cell clonal expansion through signaling mediated by the mammalian target of rapamycin. J. Immunol. 176, 2730-2738.

Cresswell P (1994). Assembly, transport, and function of MHC class II molecules. Annu. Rev. Immunol. 12, 259-293.

Dazzi C, Cariello A, Giannini M, Del D M, Giovanis P, Fiorentini G, Leoni M, Rosti G, Turci D, Tienghi A, Vertogen B, Zumaglini F, De G U, Marangolo M (2000). A sequential chemo-radiotherapeutic treatment for patients with malignant gliomas: a phase II pilot study. Anticancer Res. 20, 515-518.

De V L, Zheng B, Fischer T, Elenko E, Farquhar M G (2000). The regulator of G protein signaling family. Annu. Rev. Pharmacol. Toxicol. 40, 235-271.

Delsol G, Al S T, Gatter K C, Gerdes J, Schwarting R, Caveriviere P, Rigal-Huguet F, Robert A, Stein H, Mason D Y (1988). Coexpression of epithelial membrane antigen (EMA), Ki-1, and interleukin-2 receptor by anaplastic large cell lymphomas. Diagnostic value in so-called malignant histiocytosis. Am. J. Pathol. 130, 59-70.

Dengjel J, Nastke M D, Gouttefangeas C, Gitsioudis G, Schoor O, Altenberend F, Muller M, Kramer B, Missiou A, Sauter M, Hennenlotter J, Wemet D, Stenzl A, Rammensee H G, Klingel K, Stevanovic S (2006). Unexpected Abundance of HLA Class II Presented Peptides in Primary Renal Cell Carcinomas. Clin Cancer Res. 12, 4163-4170.

Denys H, De W O, Nusgens B, Kong Y, Sciot R, Le A T, Van D K, Jadidizadeh A, Tejpar S, Marcel M, Alman B, Cassiman J J (2004). Invasion and MMP expression profile in desmoid tumours. Br. J. Cancer 90, 1443-1449.

Deshpande A, Sicinski P, Hinds P W (2005). Cyclins and cdks in development and cancer: a perspective. Oncogene 24, 2909-2915.

Di Renzo M F, Olivero M, Giacomini A, Porte H, Chastre E, Mirossay L, Nordlinger B, Bretti S, Bottardi S, Giordano S, (1995). Overexpression and amplification of the met/HGF receptor gene during the progression of colorectal cancer. Clin. Cancer Res. 1, 147-154.

Dix A R, Brooks W H, Roszman T L, Morford L A (1999). Immune defects observed in patients with primary malignant brain tumors. J. Neuroimmunol. 100, 216-232.

Dong G, Chen Z, Li Z Y, Yeh N T, Bancroft C C, Van W C (2001). Hepatocyte growth factor/scatter factor-induced activation of MEK and PI3K signal pathways contributes to expression of proangiogenic cytokines interleukin-8 and vascular endothelial growth factor in head and neck squamous cell carcinoma. Cancer Res. 61, 5911-5918.

Duchateau P N, Pullinger C R, Cho M H, Eng C, Kane J P (2001). Apolipoprotein L gene family: tissue-specific expression, splicing, promoter regions; discovery of a new gene. J. Lipid Res. 42, 620-630.

Duchateau P N, Pullinger C R, Orellana R E, Kunitake S T, Naya-Vigne J, O'Connor P M, Malloy M J, Kane J P (1997). Apolipoprotein L, a new human high density lipoprotein apolipoprotein expressed by the pancreas. Identification, cloning, characterization, and plasma distribution of apolipoprotein L. J. Biol. Chem. 272, 25576-25582.

Dudley M E, Wunderlich J R, Robbins P F, Yang J C, Hwu P, Schwartzentruber D J, Topalian S L, Sherry R, Restifo N P, Hubicki A M, Robinson M R, Raffeld M, Duray P, Seipp C A, Rogers-Freezer L, Morton K E, Mavroukakis S A, White D E, Rosenberg S A (2002). Cancer regression and autoimmunity in patients after clonal repopulation with antitumor lymphocytes. Science 298, 850-854.

Dudley M E, Wunderlich J R, Yang J C, Sherry R M, Topalian S L, Restifo N P, Royal R E, Kammula U, White D E, Mavroukakis S A, Rogers L J, Gracia G J, Jones S A, Mangiameli D P, Pelletier M M, Gea-Banacloche J, Robinson M R, Berman D M, Filie A C, Abati A, Rosenberg S A (2005). Adoptive cell transfer therapy following non-myeloablative but lymphodepleting chemotherapy for the treatment of patients with refractory metastatic melanoma. J. Clin. Oncol. 23, 2346-2357.

Duperray C, Klein B, Durie B G, Zhang X, Jourdan M, Poncelet P, Favier F, Vincent C, Brochier J, Lenoir G. (1989). Phenotypic analysis of human myeloma cell lines. Blood 73, 566-572.

Engel M, Maurel P, Margolis R U, Margolis R K (1996). Chondroitin sulfate proteoglycans in the developing central nervous system. I. cellular sites of synthesis of neurocan and phosphacan. J Comp Neurol. 366, 34-43.

Ferracini R, Di Renzo M F, Scotlandi K, Baldini N, Olivero M, Lollini P, Cremona O, Campanacci M, Comoglio P M (1995). The Met/HGF receptor is over-expressed in human osteosarcomas and is activated by either a paracrine or an autocrine circuit. Oncogene 10, 739-749.

Finn O J, Jerome K R, Henderson R A, Pecher G, Domenech N, Magarian-Blander J, Barratt-Boyes S M (1995). MUC-1 epithelial tumor mucin-based immunity and cancer vaccines. Immunol. Rev. 145, 61-89.

Fischer J, Palmedo G, von K R, Bugert P, Prayer-Galetti T, Pagano F, Kovacs G (1998). Duplication and overexpression of the mutant allele of the MET proto-oncogene in multiple hereditary papillary renal cell tumours. Oncogene 17, 733-739.

Fong L, Hou Y, Rivas A, Benike C, Yuen A, Fisher G A, Davis M M, Engleman E G (2001). Altered peptide ligand vaccination with Flt3 ligand expanded dendritic cells for tumor immunotherapy. Proc. Natl. Acad. Sci. U.S.A 98, 8809-8814.

Friedlander D R, Milev P, Karthikeyan L, Margolis R K, Margolis R U, Grumet M (1994). The neuronal chondroitin sulfate proteoglycan neurocan binds to the neural cell adhesion molecules Ng-CAM/L1/NILE and N-CAM, and inhibits neuronal adhesion and neurite outgrowth. J. Cell Biol. 125, 669-680.

Fujita K, Denda K, Yamamoto M, Matsumoto T, Fujime M, Irimura T (1999). Expression of MUC 1 mucins inversely correlated with post-surgical survival of renal cell carcinoma patients. Br. J. Cancer 80, 301-308.

Furge K A, Kiewlich D, Le P, Vo M N, Faure M, Howlett A R, Lipson K E, Woude G F, Webb C P (2001). Suppression of Ras-mediated tumorigenicity and metastasis through inhibition of the Met receptor tyrosine kinase. Proc. Natl. Acad. Sci. U.S.A 98, 10722-10727.

Furge K A, Zhang Y W, Vande Woude G F (2000). Met receptor tyrosine kinase: enhanced signaling through adapter proteins. Oncogene 19, 5582-5589.

Furuya M, Nishiyama M, Kimura S, Suyama T, Naya Y, Ito H, Nikaido T, Ishikura H (2004). Expression of regulator of G protein signalling protein 5 (RGS5) in the tumour vasculature of human renal cell carcinoma. J. Pathol. 203, 551-558.

Gaire M, Magbanua Z, McDonnell S, McNeil L, Lovett D H, Matrisian L M (1994). Structure and expression of the human gene for the matrix metalloproteinase matrilysin. J Biol. Chem. 269, 2032-2040.

Galon J, Costes A, Sanchez-Cabo F, Kirilovsky A, Mlecnik B, Lagorce-Pages C, Tosolini M, Camus M, Berger A, Wind P, Zinzindohoue F, Bruneval P, Cugnenc P H, Trajanoski Z, Fridman W H, Pages F (2006). Type, density, and location of immune cells within human colorectal tumors predict clinical outcome. Science 313, 1960-1964.

Gattinoni L, Powell D J, Jr., Rosenberg S A, Restifo N P (2006). Adoptive immunotherapy for cancer: building on success. Nat. Rev. Immunol. 6, 383-393.

Gendler S, Taylor-Papadimitriou J, Duhig T, Rothbard J, Burchell J (1988). A highly immunogenic region of a human polymorphic epithelial mucin expressed by carcinomas is made up of tandem repeats. J. Biol. Chem. 263, 12820-12823.

Gerner E W, Meyskens F L, Jr. (2004). Polyamines and cancer: old molecules, new understanding. Nat. Rev. Cancer 4, 781-792.

Gherardi E, Stoker M (1991). Hepatocyte growth factor—scatter factor: mitogen, motogen, and met. Cancer Cells 3, 227-232.

Ghosh J C, Dohi T, Kang B H, Altieri D C (2008). Hsp60 regulation of tumor cell apoptosis. J. Biol. Chem. 283, 5188-5194.

Girling A, Bartkova J, Burchell J, Gendler S, Gillett C, Taylor-Papadimitriou J (1989). A core protein epitope of the polymorphic epithelial mucin detected by the monoclonal antibody SM-3 is selectively exposed in a range of primary carcinomas. Int. J. Cancer 43, 1072-1076.

Gnjatic S, Atanackovic D, Jager E, Matsuo M, Selvakumar A, Altorki N K, Maki R G, Dupont B, Ritter G, Chen Y T, Knuth A, Old L J (2003). Survey of naturally occurring CD4+ T cell responses against NY-ESO-1 in cancer patients: correlation with antibody responses. Proc Natl. Acad. Sci. U.S.A 100, 8862-8867.

Gong L, Jiang C, Zhang B, Hu H, Wang W, Liu X (2006). Adenovirus-mediated Expression of Both Antisense Ornithine Decarboxylase and S-adenosylmethionine Decarboxylase Induces G(1) Arrest in HT-29 Cells. J. Biochem. Mol. Biol. 39, 730-736.

Grumet M, Friedlander D R, Sakurai T (1996). Functions of brain chondroitin sulfate proteoglycans during developments: interactions with adhesion molecules. Perspect. Dev. Neurobiol. 3, 319-330.

Grumet M, Milev P, Sakurai T, Karthikeyan L, Bourdon M, Margolis R K, Margolis R U (1994). Interactions with tenascin and differential effects on cell adhesion of neurocan and phosphacan, two major chondroitin sulfate proteoglycans of nervous tissue. J. Biol. Chem. 269, 12142-12146.

Grunda J M, Nabors L B, Palmer C A, Chhieng D C, Steg A, Mikkelsen T, Diasio R B, Zhang K, Allison D, Grizzle W E, Wang W, Gillespie G Y, Johnson M R (2006). Increased expression of thymidylate synthetase (TS), ubiquitin specific protease 10 (USP10) and survivin is associated with poor survival in glioblastoma multiforme (GBM). J. Neurooncol. 80, 261-274.

Gursky S, Olopade O I, Rowley J D (2001). Identification of a 1.2 Kb cDNA fragment from a region on 9p21 commonly deleted in multiple tumor types. Cancer Genet. Cytogenet. 129, 93-101.

Halaban R (1999). Melanoma cell autonomous growth: the Rb/E2F pathway. Cancer Metastasis Rev. 18, 333-343.

Hammer J, Gallazzi F, Bono E, Karr R W, Guenot J, Valsasnini P, Nagy Z A, Sinigaglia F (1995). Peptide binding specificity of HLA-DR4 molecules: correlation with rheumatoid arthritis association. J. Exp. Med. 181, 1847-1855.

Hanada K, Yewdell J W, Yang J C (2004). Immune recognition of a human renal cancer antigen through post-translational protein splicing. Nature 427, 252-256.

Hedberg Y, Davoodi E, Roos G, Ljungberg B, Landberg G (1999). Cyclin-D1 expression in human renal-cell carcinoma. Int. J. Cancer 84, 268-272.

Heid H W, Moll R, Schwetlick I, Rackwitz H R, Keenan T W (1998). Adipophilin is a specific marker of lipid accumulation in diverse cell types and diseases. Cell Tissue Res. 294, 309-321.

Heimberger A B, Hussain S F, Aldape K, Sawaya R, Archer G A, Friedman H, Reardon D, Friedman A, Bigner D D, Sampson J H. Tumor-specific peptide vaccination in newly-diagnosed patients with GBM. Journal of Clinical Oncology, 2006 ASCO Annual Meeting Proceedings Part I Vol 24, NO: 18S (June 20 Supplement), 2006: 2529. 20 Jun. 2006.

Herz C, Aumailley M, Schulte C, Schlotzer-Schrehardt U, Bruckner-Tuderman L, Has C (2006). Kindlin-1 is a phosphoprotein involved in regulation of polarity, proliferation, and motility of epidermal keratinocytes. J Biol. Chem. 281, 36082-36090.

Hwang M L, Lukens J R, Bullock T N (2007). Cognate memory CD4+ T cells generated with dendritic cell priming influence the expansion, trafficking, and differentiation of secondary CD8+ T cells and enhance tumor control. J. Immunol. 179, 5829-5838.

Jadeski L C, Chakraborty C, Lala P K (2003). Nitric oxide-mediated promotion of mammary tumour cell migration requires sequential activation of nitric oxide synthase, guanylate cyclase and mitogen-activated protein kinase. Int. J. Cancer 106, 496-504.

Janssen E M, Lemmens E E, Wolfe T, Christen U, von Herrath M G, Schoenberger S P (2003). CD4+ T cells are required for secondary expansion and memory in CD8+ T lymphocytes. Nature 421, 852-856.

Jarvinen T A, Liu E T (2006). Simultaneous amplification of HER-2 (ERBB2) and topoisomerase IIalpha (TOP2A) genes—molecular basis for combination chemotherapy in cancer. Curr. Cancer Drug Targets. 6, 579-602.

Jones L L, Margolis R U, Tuszynski M H (2003). The chondroitin sulfate proteoglycans neurocan, brevican, phosphacan, and versican are differentially regulated following spinal cord injury. Exp. Neurol. 182, 399-411.

Jucker M, Gunther A, Gradl G, Fonatsch C, Krueger G, Diehl V, Tesch H (1994). The Met/hepatocyte growth factor receptor (HGFR) gene is overexpressed in some cases of human leukemia and lymphoma. Leuk. Res. 18, 7-16.

Kajiwara Y, Yamasaki F, Hama S, Yahara K, Yoshioka H, Sugiyama K, Arita K, Kurisu K (2003). Expression of survivin in astrocytic tumors: correlation with malignant grade and prognosis. Cancer 97, 1077-1083.

Kellner U, Sehested M, Jensen P B, Gieseler F, Rudolph P (2002). Culprit and victim—DNA topoisomerase II. Lancet Oncol. 3, 235-243.

Kennedy R C, Shearer M H, Watts A M, Bright R K (2003). CD4+ T lymphocytes play a critical role in antibody production and tumor immunity against simian virus 40 large tumor antigen. Cancer Res. 63, 1040-1045.

Kloeker S, Major M B, Calderwood D A, Ginsberg M H, Jones D A, Beckerle M C (2004). The Kindler syndrome protein is regulated by transforming growth factor-beta and involved in integrin-mediated adhesion. J. Biol. Chem. 279, 6824-6833.

Kobayashi H, Omiya R, Ruiz M, Huarte E, Sarobe P, Lasarte J J, Herraiz M, Sangro B, Prieto J, Borras-Cuesta F, Celis E (2002). Identification of an antigenic epitope for helper T lymphocytes from carcinoembryonic antigen. Clin Cancer Res. 8, 3219-3225.

Koochekpour S, Jeffers M, Rulong S, Taylor G, Klineberg E, Hudson E A, Resau J H, Vande Woude G F (1997). Met and hepatocyte growth factor/scatter factor expression in human gliomas. Cancer Res. 57, 5391-5398.

Kosari F, Parker A S, Kube D M, Lohse C M, Leibovich B C, Blute M L, Cheville J C, Vasmatzis G (2005). Clear cell renal cell carcinoma: gene expression analyses identify a potential signature for tumor aggressiveness. Clin Cancer Res. 11, 5128-5139.

Kraus S, Abel P D, Nachtmann C, Linsenmann H J, Weidner W, Stamp G W, Chaudhary K S, Mitchell S E, Franke F E, Lalani e (2002). MUC1 mucin and trefoil factor 1 protein expression in renal cell carcinoma: correlation with prognosis. Hum. Pathol. 33, 60-67.

Kurokawa Y, Matoba R, Nakamori S, Takemasa I, Nagano H, Dono K, Umeshita K, Sakon M, Monden M, Kato K (2004). PCR-array gene expression profiling of hepatocellular carcinoma. J. Exp. Clin. Cancer Res. 23, 135-141.

Lemmel C, Weik S, Eberle U, Dengjel J, Kratt T, Becker H D, Rammensee H G, Stevanovic S (2004). Differential quantitative analysis of MHC ligands by mass spectrometry using stable isotope labeling. Nat. Biotechnol. 22, 450-454.

Leontiou C, Lightowlers R, Lakey J H, Austin C A (2003). Kinetic analysis of human topoisomerase IIalpha and beta DNA binding by surface plasmon resonance. FEBS Lett. 554, 206-210.

Leroy X, Copin M C, Devisme L, Buisine M P, Aubert J P, Gosselin B, Porchet N (2002). Expression of human mucin genes in normal kidney and renal cell carcinoma. Histopathology 40, 450-457.

Lew D J, Dulic V, Reed S I (1991). Isolation of three novel human cyclins by rescue of GI cyclin (Cln) function in yeast. Cell 66, 1197-1206.

Li G, Schaider H, Satyamoorthy K, Hanakawa Y, Hashimoto K, Herlyn M (2001). Downregulation of E-cadherin and Desmoglein 1 by autocrine hepatocyte growth factor during melanoma development. Oncogene 20, 8125-8135.

Li H, Leung T C, Hoffman S, Balsamo J, Lilien J (2000). Coordinate regulation of cadherin and integrin function by the chondroitin sulfate proteoglycan neurocan. J. Cell Biol. 149, 1275-1288.

Lin T S, Chiou S H, Wang L S, Huang H H, Chiang S F, Shih A Y, Chen Y L, Chen C Y, Hsu C P, Hsu N Y, Chou M C, Kuo S J, Chow K C (2004). Expression spectra of matrix metalloproteinases in metastatic non-small cell lung cancer. Oncol. Rep. 12, 717-723.

Littaua R A, Takeda A, Cruz J, Ennis F A (1992). Vaccinia virus-specific human CD4+ cytotoxic T-lymphocyte clones. J. Virol. 66, 2274-2280.

Liu X, Chen N, Wang X, He Y, Chen X, Huang Y, Yin W, Zhou Q (2006). Apoptosis and proliferation markers in diffusely infiltrating astrocytomas: profiling of 17 molecules. J. Neuropathol. Exp. Neurol. 65, 905-913.

Livingston B D, Crimi C, Grey H, Ishioka G, Chisari F V, Fikes J, Grey H, Chesnut R W, Sette A (1997). The hepatitis B virus-specific CTL responses induced in humans by lipopeptide vaccination are comparable to those elicited by acute viral infection. J. Immunol. 159, 1383-1392.

Lo M L, Staibano S, Pannone G, Mignogna M D, Mariggio A, Salvatore G, Chieffi P, Tramontano D, De R G, Altieri D C (2001). Expression of the apoptosis inhibitor survivin in aggressive squamous cell carcinoma. Exp. Mol. Pathol. 70, 249-254.

Loden M, Stighall M, Nielsen N H, Roos G, Emdin S O, Ostlund H, Landberg G (2002). The cyclin D1 high and cyclin E high subgroups of breast cancer: separate pathways in tumorogenesis based on pattern of genetic aberrations and inactivation of the pRb node. Oncogene 21, 4680-4690.

Louhelainen J, Wijkstrom H, Hemminki K (2000). Initiation-development modelling of allelic losses on chromosome 9 in multifocal bladder cancer. Eur. J. Cancer 36, 1441-1451.

Macdonald D R (2001). Temozolomide for recurrent high-grade glioma. Semin. Oncol 28, 3-12.

Mach B, Steimle V, Martinez-Soria E, Reith W (1996). Regulation of MHC class II genes: lessons from a disease. Annu. Rev. Immunol. 14, 301-331.

Mahlamaki E H, Barlund M, Tanner M, Gorunova L, Hoglund M, Karhu R, Kallioniemi A (2002). Frequent amplification of 8q24, 11q, 17q, and 20q-specific genes in pancreatic cancer. Genes Chromosomes. Cancer 35, 353-358.

Malcherek G, Gnau V, Stevanovic S, Rammensee H G, Jung G, Melms A (1994). Analysis of allele-specific contact sites of natural HLA-DR17 ligands. J. Immunol. 153, 1141-1149.

Manici S, Sturniolo T, Imro M A, Hammer J, Sinigaglia F, Noppen C, Spagnoli G, Mazzi B, Bellone M, Dellabona P, Protti M P (1999). Melanoma cells present a MAGE-3 epitope to CD4(+) cytotoxic T cells in association with histocompatibility leukocyte antigen DR11. J. Exp. Med. 189, 871-876.

Margolis R K, Rauch U, Maurel P, Margolis R U (1996). Neurocan and phosphacan: two major nervous tissue-specific chondroitin sulfate proteoglycans. Perspect. Dev. Neurobiol. 3, 273-290.

Mark A S, Mangkornkanok M (1989). B-cell lymphoma marking only with anti-epithelial membrane antigen. Cancer 63, 2152-2155.

Marzo A L, Kinnear B F, Lake R A, Frelinger J J, Collins E J, Robinson B W, Scott B (2000). Tumor-specific CD4+ T cells have a major "post-licensing" role in CTL mediated anti-tumor immunity. J. Immunol. 165, 6047-6055.

Maulik G, Kijima T, Ma P C, Ghosh S K, Lin J, Shapiro G I, Schaefer E, Tibaldi E, Johnson B E, Salgia R (2002). Modulation of the c-Met/hepatocyte growth factor pathway in small cell lung cancer. Clin. Cancer Res. 8, 620-627.

Mayer A, Takimoto M, Fritz E, Schellander G, Kofler K, Ludwig H (1993). The prognostic significance of proliferating cell nuclear antigen, epidermal growth factor receptor, and mdr gene expression in colorectal cancer. Cancer 71, 2454-2460.

McKeon R J, Jurynec M J, Buck C R (1999). The chondroitin sulfate proteoglycans neurocan and phosphacan are expressed by reactive astrocytes in the chronic CNS glial scar. J. Neurosci. 19, 10778-10788.

Mellai M, Caldera V, Patrucco A, Annovazzi L, Schiffer D (2008). Survivin expression in glioblastomas correlates with proliferation, but not with apoptosis. Anticancer Res. 28, 109-118.

Meyer-Puttlitz B, Junker E, Margolis R U, Margolis R K (1996). Chondroitin sulfate proteoglycans in the developing central nervous system. II. Immunocytochemical localization of neurocan and phosphacan. J Comp Neurol. 366, 44-54.

Miyazaki K, Hattori Y, Umenishi F, Yasumitsu H, Umeda M (1990). Purification and characterization of extracellular matrix-degrading metalloproteinase, matrin (pump-1), secreted from human rectal carcinoma cell line. Cancer Res. 50, 7758-7764.

Mizuno K, Higuchi O, Ihle J N, Nakamura T (1993). Hepatocyte growth factor stimulates growth of hematopoietic progenitor cells. Biochem. Biophys. Res. Commun. 194, 178-186.

Molenkamp B G, Vuylsteke R J, van Leeuwen P A, Meijer S, Vos W, Wijnands P G, Scheper R J, de Gruijl T D (2005). Matched skin and sentinel lymph node samples of melanoma patients reveal exclusive migration of mature dendritic cells. Am. J. Pathol. 167, 1301-1307.

Monajemi H, Fontijn R D, Pannekoek H, Horrevoets A J (2002). The apolipoprotein L gene cluster has emerged recently in evolution and is expressed in human vascular tissue. Genomics 79, 539-546.

Montesano R, Soriano J V, Malinda K M, Ponce M L, Bafico A, Kleinman H K, Bottaro D P, Aaronson S A (1998). Differential effects of hepatocyte growth factor isoforms on epithelial and endothelial tubulogenesis. Cell Growth Differ. 9, 355-365.

Morgan R A, Dudley M E, Wunderlich J R, Hughes M S, Yang J C, Sherry R M, Royal R E, Topalian S L, Kammula U S, Restifo N P, Zheng Z, Nahvi A, de Vries C R, Rogers-Freezer L J, Mavroukakis S A, Rosenberg S A (2006). Cancer Regression in Patients After Transfer of Genetically Engineered Lymphocytes. Science.

Morgenstern D A, Asher R A, Fawcett J W (2002). Chondroitin sulphate proteoglycans in the CNS injury response. Prog. Brain Res. 137, 313-332.

Mori M, Barnard G F, Mimori K, Ueo H, Akiyoshi T, Sugimachi K (1995). Overexpression of matrix metalloproteinase-7 mRNA in human colon carcinomas. Cancer 75, 1516-1519.

Mortara L, Castellani P, Meazza R, Tosi G, De Lerma B A, Procopio F A, Comes A, Zardi L, Ferrini S, Accolla R S (2006). CIITA-induced MHC class II expression in mammary adenocarcinoma leads to a Th1 polarization of the tumor microenvironment, tumor rejection, and specific antitumor memory. Clin Cancer Res. 12, 3435-3443.

Mott J D, Werb Z (2004). Regulation of matrix biology by matrix metalloproteinases. Curr. Opin. Cell Biol 16, 558-564.

Nakamura T, Tabuchi Y, Nakae S, Ohno M, Saitoh Y (1996). Serum carcinoembryonic antigen levels and proliferating cell nuclear antigen labeling index for patients with colorectal carcinoma. Correlation with tumor progression and survival. Cancer 77, 1741-1746.

Naldini L, Vigna E, Narsimhan R P, Gaudino G, Zarnegar R, Michalopoulos G K, Comoglio P M (1991). Hepatocyte growth factor (HGF) stimulates the tyrosine kinase activity of the receptor encoded by the proto-oncogene c-MET. Oncogene 6, 501-504.

Napolitano M, Keime-Guibert F, Monjour A, Lafitte C, Ameri A, Cornu P, Broet P, Delattre J Y (1999). Treatment of supratentorial glioblastoma multiforme with radiotherapy and a combination of BCNU and tamoxifen: a phase II study. J. Neurooncol. 45, 229-235.

Nieder C, Grosu A L, Molls M (2000). A comparison of treatment results for recurrent malignant gliomas. Cancer Treat. Rev. 26, 397-409.

Noto H, Takahashi T, Makiguchi Y, Hayashi T, Hinoda Y, Imai K (1997). Cytotoxic T lymphocytes derived from bone marrow mononuclear cells of multiple myeloma patients recognize an underglycosylated form of MUC1 mucin. Int. Immunol. 9, 791-798.

Novellino L, Castelli C, Parmiani G (2005). A listing of human tumor antigens recognized by T cells: March 2004 update. Cancer Immunol. Immunother. 54, 187-207.

O'Driscoll L, Linehan R, Clynes M (2003). Survivin: role in normal cells and in pathological conditions. Curr. Cancer Drug Targets. 3, 131-152.

Ohara O, Nagase T, Ishikawa K, Nakajima D, Ohira M, Seki N, Nomura N (1997). Construction and characterization of human brain cDNA libraries suitable for analysis of cDNA clones encoding relatively large proteins. DNA Res. 4, 53-59.

Oka Y, Tsuboi A, Taguchi T, Osaki T, Kyo T, Nakajima H, Elisseeva O A, Oji Y, Kawakami M, Ikegame K, Hosen N, Yoshihara S, Wu F, Fujiki F, Murakami M, Masuda T, Nishida S, Shirakata T, Nakatsuka S, Sasaki A, Udaka K, Dohy H, Aozasa K, Noguchi S, Kawase I, Sugiyama H (2004). Induction of WT1 (Wilms' tumor gene)-specific cytotoxic T lymphocytes by WT1 peptide vaccine and the resultant cancer regression. Proc Natl. Acad. Sci. U.S. A 101, 13885-13890.

Penna A, Fowler P, Bertoletti A, Guilhot S, Moss B, Margolskee R F, Cavalli A, Valli A, Fiaccadori F, Chisari F V. (1992). Hepatitis B virus (HBV)-specific cytotoxic T-cell (CTL) response in humans: characterization of HLA class II-restricted CTLs that recognize endogenously synthesized HBV envelope antigens. J. Virol. 66, 1193-1198.

Piesche M, Hildebrandt Y, Zettl F, Chapuy B, Schmitz M, Wulf G, Trumper L, Schroers R (2007). Identification of a promiscuous HLA DR-restricted T-cell epitope derived from the inhibitor of apoptosis protein survivin. Hum. Immunol. 68, 572-576.

Pons E, Uphoff C C, Drexler H G (1998). Expression of hepatocyte growth factor and its receptor c-met in human leukemia-lymphoma cell lines. Leuk. Res. 22, 797-804.

Ponzetto C, Bardelli A, Maina F, Longati P, Panayotou G, Dhand R, Waterfield M D, Comoglio P M (1993). A novel recognition motif for phosphatidylinositol 3-kinase binding mediates its association with the hepatocyte growth factor/scatter factor receptor. Mol. Cell. Biol. 13, 4600-4608.

Prados M D, Levin V (2000). Biology and treatment of malignant glioma. Semin. Oncol 27, 1-10.

Previsani N, Lavanchy D (2002). Hepatitis B. World Health Organization Department of Communicable Diseases Surveillance and Response. 2002 WHO/CDS/CSR/LYO/ 2002. 2:Hepatitis B.

Qian C N, Guo X, Cao B, Kort E J, Lee C C, Chen J, Wang L M, Mai W Y, Min H Q, Hong M H, Vande Woude G F, Resau J H, Teh B T (2002). Met protein expression level correlates with survival in patients with late-stage nasopharyngeal carcinoma. Cancer Res. 62, 589-596.

Qin Z, Blankenstein T (2000). CD4+ T cell—mediated tumor rejection involves inhibition of angiogenesis that is dependent on IFN gamma receptor expression by nonhematopoietic cells. Immunity. 12, 677-686.

Qin Z, Schwartzkopff J, Pradera F, Kammertoens T, Seliger B, Pircher H, Blankenstein T (2003). A critical requirement of interferon gamma-mediated angiostasis for tumor rejection by CD8+ T cells. Cancer Res. 63, 4095-4100.

Quantin B, Murphy G, Breathnach R (1989). Pump-1 cDNA codes for a protein with characteristics similar to those of classical collagenase family members. Biochemistry 28, 5327-5334.

Rae F K, Stephenson S A, Nicol D L, Clements J A (2000). Novel association of a diverse range of genes with renal cell carcinoma as identified by differential display. Int. J. Cancer 88, 726-732.

Ramirez R, Hsu D, Patel A, Fenton C, Dinauer C, Tuttle R M, Francis G L (2000). Over-expression of hepatocyte growth factor/scatter factor (HGF/SF) and the HGF/SF receptor (cMET) are associated with a high risk of metastasis and recurrence for children and young adults with papillary thyroid carcinoma. Clin Endocrinol. (Oxf) 53, 635-644.

Rammensee H G, Bachmann J, Emmerich N P, Bachor O A, Stevanovic S (1999). SYFPEITHI: database for MHC ligands and peptide motifs. Immunogenetics 50, 213-219.

Rammensee, H. G., Bachmann, J., and Stevanovic, S. (1997). MHC Ligands and Peptide Motifs. Springer-Verlag, Heidelberg, Germany).

Rammensee H G, Friede T, Stevanoviic S (1995). MHC ligands and peptide motifs: first listing. Immunogenetics 41, 178-228.

Rauch U, Feng K, Zhou X H (2001). Neurocan: a brain chondroitin sulfate proteoglycan. Cell Mol. Life. Sci. 58, 1842-1856.

Rehermann B, Nascimbeni M (2005). Immunology of hepatitis B virus and hepatitis C virus infection. Nat. Rev. Immunol. 5, 215-229.

Retzler C, Gohring W, Rauch U (1996). Analysis of neurocan structures interacting with the neural cell adhesion molecule N-CAM. J. Biol. Chem. 271, 27304-27310.

Rosenberg S A, Lotze M T, Muul L M, Chang A E, Avis F P, Leitman S, Linehan W M, Robertson C N, Lee R E, Rubin J T. (1987). A progress report on the treatment of 157 patients with advanced cancer using lymphokine-activated killer cells and interleukin-2 or high-dose interleukin-2 alone. N. Engl. J. Med. 316, 889-897.

Rosenberg S A, Packard B S, Aebersold P M, Solomon D, Topalian S L, Toy S T, Simon P, Lotze M T, Yang J C, Seipp C A. (1988). Use of tumor-infiltrating lymphocytes and interleukin-2 in the immunotherapy of patients with metastatic melanoma. A preliminary report. N. Engl. J Med 319, 1676-1680.

Roth W, Weller M (1999). Chemotherapy and immunotherapy of malignant glioma: molecular mechanisms and clinical perspectives. Cell Mol. Life. Sci. 56, 481-506.

Rubin J S, Bottaro D P, Aaronson S A (1993). Hepatocyte growth factor/scatter factor and its receptor, the c-met proto-oncogene product. Biochim. Biophys. Acta 1155, 357-371.

Ruiz M, Kobayashi H, Lasarte J J, Prieto J, Borras-Cuesta F, Celis E, Sarobe P (2004). Identification and characterization of a T-helper peptide from carcinoembryonic antigen. Clin Cancer Res. 10, 2860-2867.

Sablotzki A, Ebel H, Muhling J, Dehne M G, Nopens H, Giesselmann H, Hempelmann G (2000). Dysregulation of immune response following neurosurgical operations. Acta Anaesthesiol. Scand. 44, 82-87.

Sadler E, Klausegger A, Muss W, Deinsberger U, Pohla-Gubo G, Laimer M, Lanschuetzer C, Bauer J W, Hintner H (2006). Novel KIND1 gene mutation in Kindler syndrome with severe gastrointestinal tract involvement. Arch. Dermatol. 142, 1619-1624.

Saha S, Bardelli A, Buckhaults P, Velculescu V E, Rago C, St C B, Romans K E, Choti M A, Lengauer C, Kinzler K W, Vogelstein B (2001). A phosphatase associated with metastasis of colorectal cancer. Science 294, 1343-1346.

Saino M, Maruyama T, Sekiya T, Kayama T, Murakami Y (2004). Inhibition of angiogenesis in human glioma cell lines by antisense RNA from the soluble guanylate cyclase genes, GUCY1A3 and GUCY1B3. Oncol. Rep. 12, 47-52.

Saito T, Arifin M T, Hama S, Kajiwara Y, Sugiyama K, Yamasaki F, Hidaka T, Arita K, Kurisu K (2007). Survivin subcellular localization in high-grade astrocytomas: simultaneous expression in both nucleus and cytoplasm is negative prognostic marker. J. Neurooncol. 82, 193-198.

Sakaguchi A, Kikuchi A (2004). Functional compatibility between isoform alpha and beta of type II DNA topoisomerase. J Cell Sci. 117, 1047-1054.

Sasaki T, Lopes M B, Hankins G R, Helm G A (2002). Expression of survivin, an inhibitor of apoptosis protein, in tumors of the nervous system. Acta Neuropathol. 104, 105-109.

Sato F, Abraham J M, Yin J, Kan T, Ito T, Mori Y, Hamilton J P, Jin Z, Cheng Y, Paun B, Berki A T, Wang S, Shimada Y, Meltzer S J (2006). Polo-like kinase and survivin are esophageal tumor-specific promoters. Biochem. Biophys. Res. Commun. 342, 465-471.

Schmidt C, Bladt F, Goedecke S, Brinkmann V, Zschiesche W, Sharpe M, Gherardi E, Birchmeier C (1995). Scatter factor/hepatocyte growth factor is essential for liver development. Nature 373, 699-702.

Schmitz M, Diestelkoetter P, Weigle B, Schmachtenberg F, Stevanovic S, Ockert D, Rammensee H G, Rieber E P (2000). Generation of survivin-specific CD8+ T effector cells by dendritic cells pulsed with protein or selected peptides. Cancer Res. 60, 4845-4849.

Schoenberger S P, Toes R E, van d, V, Offring a R, Melief C J (1998). T-cell help for cytotoxic T lymphocytes is mediated by CD40-CD40L interactions. Nature 393, 480-483.

Schubert U, Anton L C, Gibbs J, Norbury C C, Yewdell J W, Bennink J R (2000). Rapid degradation of a large fraction of newly synthesized proteins by proteasomes. Nature 404, 770-774.

Shedlock D J, Shen H (2003). Requirement for CD4 T cell help in generating functional CD8 T cell memory. Science 300, 337-339.

Siddiqui J, Abe M, Hayes D, Shani E, Yunis E, Kufe D (1988). Isolation and Sequencing of a cDNA Coding for the Human DF3 Breast Carcinoma-Associated Antigen. PNAS 85, 2320-2323.

Singh-Jasuja H, Emmerich N P, Rammensee H G (2004). The Tubingen approach: identification, selection, and validation of tumor-associated HLA peptides for cancer therapy. Cancer Immunol. Immunother. 53, 187-195.

Smith G M, Strunz C (2005). Growth factor and cytokine regulation of chondroitin sulfate proteoglycans by astrocytes. Glia 52, 209-218.

Span P N, Sweep F C, Wiegerinck E T, Tjan-Heijnen V C, Manders P, Beex L V de Kok J B (2004). Survivin is an independent prognostic marker for risk stratification of breast cancer patients. Clin Chem. 50, 1986-1993.

Sun J C, Bevan M J (2003). Defective CD8 T cell memory following acute infection without CD4 T cell help. Science 300, 339-342.

Takahashi T, Makiguchi Y, Hinoda Y, Kakiuchi H, Nakagawa N, Imai K, Yachi A (1994). Expression of MUC1 on myeloma cells and induction of HLA-unrestricted CTL against MUC1 from a multiple myeloma patient. J. Immunol. 153, 2102-2109.

Takayama H, Larochelle W J, Sharp R, Otsuka T, Kriebel P, Anver M, Aaronson S A, Merlino G (1997). Diverse tumorigenesis associated with aberrant development in mice overexpressing hepatocyte growth factor/scatter factor. Proc. Natl. Acad. Sci. U.S. A 94, 701-706.

Takayama H, LaRochelle W J, Anver M, Bockman D E, Merlino G (1996). Scatter factor/hepatocyte growth factor as a regulator of skeletal muscle and neural crest development. PNAS 93, 5866-5871.

Tan H Y, Liu J, Wu S M, Luo H S (2005). Expression of a novel apoptosis inhibitor-survivin in colorectal carcinoma. World J. Gastroenterol. 11, 4689-4692.

Ten K M van der Wal J B, Sluiter W, Hofland L J, Jeekel J, Sonneveld P, van Eijck C H (2006). The role of superoxide anions in the development of distant tumour recurrence. Br. J. Cancer.

Teofili L, Di Febo A L, Pierconti F, Maggiano N, Bendandi M, Rutella S, Cingolani A, Di R N, Musto P, Pileri S, Leone G, Larocca L M (2001). Expression of the c-met proto-oncogene and its ligand, hepatocyte growth factor, in Hodgkin disease. Blood 97, 1063-1069.

Tompkins S M, Rota P A, Moore J C, Jensen P E (1993). A europium fluoroimmunoassay for measuring binding of antigen to class II MHC glycoproteins. J. Immunol. Methods 163, 209-216.

Tripathi A, Dasgupta S, Roy A, Sengupta A, Roy B, Roychowdhury S, Panda C K (2003). Sequential deletions in both arms of chromosome 9 are associated with the development of head and neck squamous cell carcinoma in Indian patients. J. Exp. Clin. Cancer Res. 22, 289-297.

Troussard X, vet-Loiseau H, Macro M, Mellerin M P, Malet M, Roussel M, Sola B (2000). Cyclin D1 expression in patients with multiple myeloma. Hematol. J. 1, 181-185.

Tuck A B, Park M, Sterns E E, Boag A, Elliott B E (1996). Coexpression of hepatocyte growth factor and receptor (Met) in human breast carcinoma. Am. J. Pathol. 148, 225-232.

Uehara Y, Minowa O, Mori C, Shiota K, Kuno J, Noda T, Kitamura N (1995). Placental defect and embryonic lethality in mice lacking hepatocyte growth factor/scatter factor. Nature 373, 702-705.

Uematsu M, Ohsawa I, Aokage T, Nishimaki K, Matsumoto K, Takahashi H, Asoh S, Teramoto A, Ohta S (2005). Prognostic significance of the immunohistochemical index of survivin in glioma: a comparative study with the MIB-1 index. J. Neurooncol. 72, 231-238.

van der Bruggen P, Traversari C, Chomez P, Lurquin C, De P E, Van den E B, Knuth A, Boon T (1991). A gene encoding an antigen recognized by cytolytic T lymphocytes on a human melanoma. Science 254, 1643-1647.

van d, V, Taher T E, Keehnen R M, Smit L, Groenink M, Pals S T (1997). Paracrine regulation of germinal center B cell adhesion through the c-met-hepatocyte growth factor/scatter factor pathway. J. Exp. Med. 185, 2121-2131.

Vasef M A, Brynes R K, Sturm M, Bromley C, Robinson R A (1999). Expression of cyclin D1 in parathyroid carcinomas, adenomas, and hyperplasias: a paraffin immunohistochemical study. Mod. Pathol. 12, 412-416.

Vigneron N, Stroobant V, Chapiro J, Ooms A, Degiovanni G, Morel S, van der B P, Boon T, Van Den Eynde B J (2004). An antigenic peptide produced by peptide splicing in the proteasome. Science 304, 587-590.

Vogt A B, Kropshofer H, Kalbacher H, Kalbus M, Rammensee H G, Coligan J E, Martin R (1994). Ligand motifs of HLA-DRB5*0101 and DRB1*1501 molecules delineated from self-peptides. J. Immunol. 153, 1665-1673.

Walter S, Herrgen L, Schoor O, Jung G, Wernet D, Buhring H J, Rammensee H G, Stevanovic S (2003). Cutting edge: predetermined avidity of human CD8 T cells expanded on calibrated MHC/anti-CD28-coated microspheres. J. Immunol. 171, 4974-4978.

Wang F Q, So J, Reierstad S, Fishman D A (2005). Matrilysin (MMP-7) promotes invasion of ovarian cancer cells by activation of progelatinase. Int. J. Cancer 114, 19-31.

Wang J C, Livingstone A M (2003). Cutting edge: CD4+ T cell help can be essential for primary CD8+ T cell responses in vivo. J. Immunol. 171, 6339-6343.

Wang R, Ferrell L D, Faouzi S, Maher J J, Bishop J M (2001). Activation of the Met receptor by cell attachment induces and sustains hepatocellular carcinomas in transgenic mice. J. Cell Biol. 153, 1023-1034.

Weber R G, Rieger J, Naumann U, Lichter P, Weller M (2001). Chromosomal imbalances associated with response to chemotherapy and cytotoxic cytokines in human malignant glioma cell lines. Int. J. Cancer 91, 213-218.

Weinschenk T, Gouttefangeas C, Schirle M, Obermayr F, Walter S, Schoor O, Kurek R, Loeser W, Bichler K H, Wernet D, Stevanovic S, Rammensee H G (2002). Integrated functional genomics approach for the design of patient-individual antitumor vaccines. Cancer Res. 62, 5818-5827.

Weinstein E J, Bourner M, Head R, Zakeri H, Bauer C, Mazzarella R (2003). URP1: a member of a novel family of PH and FERM domain-containing membrane-associated proteins is significantly over-expressed in lung and colon carcinomas. Biochim. Biophys. Acta 1637, 207-216.

Wierecky J, Muller M R, Horger M S, Brugger W, Kanz L, Brossart P (2005). Induction of clinical and immunological responses in patients with metastatic renal cell carcinoma after vaccinations with peptide pulsed dendritic cells. J Clin Oncol (Meeting Abstracts) 23, 2507.

Xie D, Zeng Y X, Wang H J, Wen J M, Tao Y, Sham J S, Guan X Y (2006). Expression of cytoplasmic and nuclear Survivin in primary and secondary human glioblastoma. Br. J. Cancer 94, 108-114.

Xiong Y, Connolly T, Futcher B, Beach D (1991). Human D-type cyclin. Cell 65, 691-699.

Yamashita S, Masuda Y, Kurizaki T, Haga Y, Murayama T, Ikei S, Kamei M, Takeno S, Kawahara K (2007). Survivin expression predicts early recurrence in early-stage breast cancer. Anticancer Res. 27, 2803-2808.

Yee C, Thompson J A, Byrd D, Riddell S R, Roche P, Celis E, Greenberg P D (2002). Adoptive T cell therapy using antigen-specific CD8+ T cell clones for the treatment of patients with metastatic melanoma: in vivo persistence, migration, and antitumor effect of transferred T cells. Proc. Natl. Acad. Sci. U.S. A 99, 16168-16173.

Young A N, Amin M B, Moreno C S, Lim S D, Cohen C, Petros J A, Marshall F F, Neish A S (2001). Expression profiling of renal epithelial neoplasms: a method for tumor classification and discovery of diagnostic molecular markers. Am. J. Pathol. 158, 1639-1651.

Zacharias U, Rauch U (2006). Competition and cooperation between tenascin-R, lecticans and contactin 1 regulate neurite growth and morphology. J Cell Sci. 119, 3456-3466.

Zaremba S, Barzaga E, Zhu M, Soares N, Tsang K Y, Schlom J (1997). Identification of an enhancer agonist cytotoxic T lymphocyte peptide from human carcinoembryonic antigen. Cancer Res. 57, 4570-4577.

Zamegar R, Michalopoulos G K (1995). The many faces of hepatocyte growth factor: from hepatopoiesis to hematopoiesis. J. Cell Biol. 129, 1177-1180.

Zeh H J III, Perry-Lalley D, Dudley M E, Rosenberg S A, Yang J C (1999). High avidity CTLs for two self-antigens demonstrate superior in vitro and in vivo antitumor efficacy. J. Immunol. 162, 989-994.

Zhang B, Liu X X, Zhang Y, Jiang C Y, Hu H Y, Gong L, Liu M, Teng Q S (2006). Polyamine depletion by ODC-AdoMetDC antisense adenovirus impairs human colorectal cancer growth and invasion in vitro and in vivo. J Gene Med 8, 980-989.

Zhen H N, Zhang X, Hu P Z, Yang T T, Fei Z, Zhang J N, Fu L A, He X S, Ma F C, Wang X L (2005). Survivin expression and its relation with proliferation, apoptosis, and angiogenesis in brain gliomas. Cancer 104, 2775-2783.

Zhou Y T, Guy G R, Low B C (2005). BNIP-2 induces cell elongation and membrane protrusions by interacting with Cdc42 via a unique Cdc42-binding motif within its BNIP-2 and Cdc42GAP homology domain. Exp. Cell Res. 303, 263-274.

The invention claimed is:

1. A fusion protein comprising N-terminal amino acids 1-80 of the HLA-DR antigen-associated invariant chain (Ii) and a peptide selected from the group consisting of SEQ ID NO: 1, SEQ ID NO: 2, and SEQ ID NO: 3.

2. A peptide consisting of a sequence selected from the group consisting of SEQ ID NO: 1 and SEQ ID NO: 2, or a pharmaceutically acceptable salt thereof.

3. A kit, comprising:
   (a) a container that contains a pharmaceutical composition containing a peptide or pharmaceutically acceptable salt according to claim 2 in solution or in lyophilized form;
   (b) optionally, a second container containing a diluent or reconstituting solution for the lyophilized formulation;
   (c) optionally, at least one peptide selected from the group consisting of the peptides according to SEQ ID NOS: 4 to 24; and
   (d) optionally, instructions for the use of the solution and/or the reconstitution and/or use of the lyophilized formulation.

4. A pharmaceutical composition comprising a peptide according to claim 2 or a pharmaceutically acceptable salt thereof.

5. The pharmaceutical composition according to claim 4, further comprising at least one peptide comprising a sequence selected from the group consisting of SEQ ID NO: 4 to SEQ ID NO: 13 and SEQ ID NO: 24.

6. The pharmaceutical composition according to claim 4, further comprising at least one peptide comprising a sequence selected from the group consisting of SEQ ID NOS: 4, 8, 11, 12, 15 and 24.

7. The pharmaceutical composition according to claim 4 further comprising a pharmaceutically acceptable liquid.

8. A method of producing a peptide according to claim 2, the method comprising culturing a host cell comprising an expression vector encoding the peptide, and isolating the peptide from the host cell or its culture medium.

* * * * *